(12) United States Patent
Abercrombie, II et al.

(10) Patent No.: US 12,213,791 B2
(45) Date of Patent: Feb. 4, 2025

(54) WEARABLE DEVICE

(71) Applicant: iRhythm Technologies, Inc., San Francisco, CA (US)

(72) Inventors: Jeffrey Joseph Abercrombie, II, Oakland, CA (US); Genaro Sebastian Sepulveda, Oakland, CA (US); Shena Hae Park, San Francisco, CA (US); Ryan James Wensley, San Francisco, CA (US); James Kihyun Lee, San Francisco, CA (US); Thomas Burnell Reeve, III, San Francisco, CA (US)

(73) Assignee: iRhythm Technologies, Inc., San Francisco, CA (US)

( * ) Notice: Subject to any disclaimer, the term of this patent is extended or adjusted under 35 U.S.C. 154(b) by 0 days.

(21) Appl. No.: 18/363,356

(22) Filed: Aug. 1, 2023

(65) Prior Publication Data
US 2023/0371873 A1 Nov. 23, 2023

Related U.S. Application Data

(63) Continuation of application No. 18/175,315, filed on Feb. 27, 2023, now Pat. No. 11,806,150, which is a (Continued)

(51) Int. Cl.
*H05K 7/00* (2006.01)
*A61B 5/00* (2006.01)
(Continued)

(52) U.S. Cl.
CPC .............. *A61B 5/257* (2021.01); *A61B 5/282* (2021.01); *A61B 5/6833* (2013.01);
(Continued)

(58) Field of Classification Search
CPC .. H05K 5/0026; H05K 5/0086; H05K 5/0226; H05K 5/0017
(Continued)

(56) References Cited

U.S. PATENT DOCUMENTS 1,497,079 A 6/1924 Gullborg
2,179,922 A 11/1939 Dana
(Continued)

FOREIGN PATENT DOCUMENTS

AU 2011252998 8/2015
AU 2014209376 6/2017
(Continued)

OTHER PUBLICATIONS

US 8,750,980 B2, 06/2014, Katra et al. (withdrawn)
(Continued)

*Primary Examiner* — Hung S. Bui
(74) *Attorney, Agent, or Firm* — Knobbe, Martens, Olson & Bear, LLP

(57) ABSTRACT

The present disclosure relates to a wearable device and systems/methods relating to the device. Certain embodiments may include two flexible wings and a bridge connecting the two wings. In some embodiments, the upper surface of the bridge can be non-adhesive and uncoupled to the flexible wing such that the flexible wing can be decoupled from the bridge when the adhesive is adhered to the surface of a user.

20 Claims, 35 Drawing Sheets

Related U.S. Application Data continuation of application No. 17/805,622, filed on Jun. 6, 2022, now Pat. No. 11,589,792, which is a continuation of application No. 17/396,130, filed on Aug. 6, 2021, now Pat. No. 11,350,865.

(60) Provisional application No. 63/062,293, filed on Aug. 6, 2020.

(51) Int. Cl.
| | | |
|---|---|---|
| *A61B 5/257* | (2021.01) | |
| *A61B 5/282* | (2021.01) | |
| *H05K 5/00* | (2006.01) | |
| *H05K 5/02* | (2006.01) | |
| *H05K 7/14* | (2006.01) | |

(52) U.S. Cl.
CPC ......... *H05K 5/0026* (2013.01); *H05K 5/0086* (2013.01); *H05K 5/0226* (2013.01); *H05K 7/1427* (2013.01); *A61B 2562/0215* (2017.08); *A61B 2562/0217* (2017.08); *A61B 2562/166* (2013.01); *A61B 2562/227* (2013.01)

(58) Field of Classification Search
USPC .......................................... 361/728; 600/391
See application file for complete search history.

(56) References Cited

U.S. PATENT DOCUMENTS

| | | | |
|---|---|---|---|
| 2,201,645 | A | 5/1940 | Epner |
| 2,311,060 | A | 2/1943 | Lurrain |
| 2,444,552 | A | 7/1948 | Brantingson |
| 2,500,840 | A | 3/1950 | Lyons |
| 3,215,136 | A | 11/1965 | Holter et al. |
| 3,547,107 | A | 12/1970 | Chapman et al. |
| 3,697,706 | A | 10/1972 | Huggard |
| 3,870,034 | A | 3/1975 | James |
| 3,882,853 | A | 5/1975 | Gofman |
| 3,911,906 | A | 10/1975 | Reinhold |
| 4,023,312 | A | 5/1977 | Stickney |
| 4,027,664 | A | 6/1977 | Heavner, Jr. et al. |
| 4,082,087 | A | 4/1978 | Howson |
| 4,121,573 | A | 10/1978 | Crovella et al. |
| 4,123,785 | A | 10/1978 | Cherry et al. |
| 4,126,126 | A | 11/1978 | Bare |
| 4,202,139 | A | 5/1980 | Hong et al. |
| 4,274,419 | A | 6/1981 | Tam et al. |
| 4,274,420 | A | 6/1981 | Hymes |
| 4,286,610 | A | 9/1981 | Jones |
| 4,333,475 | A | 6/1982 | Moreno et al. |
| 4,361,990 | A | 12/1982 | Link |
| 4,381,792 | A | 5/1983 | Busch |
| 4,438,767 | A | 3/1984 | Nelson |
| 4,459,987 | A | 7/1984 | Pangburn |
| 4,535,783 | A | 8/1985 | Marangoni |
| 4,537,207 | A | 8/1985 | Gilhaus |
| 4,572,187 | A | 2/1986 | Schetrumpf |
| 4,621,465 | A | 11/1986 | Pangburn |
| 4,622,979 | A | 11/1986 | Katchis et al. |
| 4,658,826 | A | 4/1987 | Weaver |
| 4,712,552 | A | 12/1987 | Pangburn |
| 4,736,752 | A | 4/1988 | Munck et al. |
| 4,855,294 | A | 8/1989 | Patel |
| 4,925,453 | A | 5/1990 | Kannankeril |
| 4,938,228 | A | 7/1990 | Righter et al. |
| 4,981,141 | A | 1/1991 | Segalowitz |
| 5,003,987 | A | 4/1991 | Grinwald |
| 5,027,824 | A | 7/1991 | Dougherty et al. |
| 5,082,851 | A | 1/1992 | Appelbaum et al. |
| 5,086,778 | A | 2/1992 | Mueller et al. |
| 5,191,891 | A | 3/1993 | Righter |
| 5,205,295 | A | 4/1993 | Del Mar et al. |
| 5,226,425 | A | 7/1993 | Righter |
| 5,228,450 | A | 7/1993 | Sellers |
| 5,230,119 | A | 7/1993 | Woods et al. |
| 5,289,824 | A | 3/1994 | Mills et al. |
| 5,305,746 | A | 4/1994 | Fendrock |
| 5,309,909 | A | 5/1994 | Gadsby |
| 5,328,935 | A | 7/1994 | Van Phan |
| 5,365,935 | A | 11/1994 | Righter et al. |
| 5,458,141 | A | 10/1995 | Neil |
| 5,483,967 | A | 1/1996 | Ohtake |
| 5,489,624 | A | 2/1996 | Kantner et al. |
| 5,511,548 | A | 4/1996 | Riazzi et al. |
| 5,511,553 | A | 4/1996 | Segalowitz |
| 5,515,858 | A | 5/1996 | Myllymaki |
| 5,536,768 | A | 7/1996 | Kantner et al. |
| 5,581,369 | A | 12/1996 | Righter et al. |
| 5,626,140 | A | 5/1997 | Feldman et al. |
| 5,634,468 | A | 6/1997 | Platt et al. |
| 5,645,063 | A | 7/1997 | Straka |
| 5,645,068 | A | 7/1997 | Mezack et al. |
| 5,730,143 | A | 3/1998 | Schwarzberg |
| 5,749,365 | A | 5/1998 | Magill |
| 5,749,367 | A | 5/1998 | Gamlyn et al. |
| 5,771,524 | A | 6/1998 | Woods et al. |
| 5,772,604 | A | 6/1998 | Langberg et al. |
| 5,776,072 | A | 7/1998 | Hsu et al. |
| 5,881,743 | A | 3/1999 | Nadel |
| D408,541 | S | 4/1999 | Dunshee et al. |
| 5,916,239 | A | 6/1999 | Geddes et al. |
| 5,931,791 | A | 8/1999 | Saltzstein et al. |
| 5,941,829 | A | 8/1999 | Saltzstein et al. |
| 5,957,854 | A | 9/1999 | Besson et al. |
| 5,959,529 | A | 9/1999 | Kail |
| 6,013,007 | A | 1/2000 | Root et al. |
| 6,032,060 | A | 2/2000 | Carim |
| 6,038,464 | A | 3/2000 | Axelgaard et al. |
| 6,038,469 | A | 3/2000 | Karlsson et al. |
| 6,044,515 | A | 4/2000 | Zygmont |
| 6,093,146 | A | 7/2000 | Filangeri |
| D429,336 | S | 8/2000 | Francis et al. |
| 6,102,856 | A | 8/2000 | Groff et al. |
| 6,117,077 | A | 9/2000 | Del Mar et al. |
| 6,121,508 | A | 9/2000 | Bischof |
| 6,132,371 | A | 10/2000 | Dempsey et al. |
| 6,134,480 | A | 10/2000 | Minogue |
| 6,136,008 | A | 10/2000 | Becker et al. |
| 6,161,036 | A | 12/2000 | Matsumura et al. |
| 6,169,915 | B1 | 1/2001 | Krumbiegel et al. |
| 6,178,357 | B1 | 1/2001 | Gliner et al. |
| 6,200,265 | B1 | 3/2001 | Walsh et al. |
| 6,225,901 | B1 | 5/2001 | Kail |
| 6,232,366 | B1 | 5/2001 | Wang et al. |
| 6,238,338 | B1 | 5/2001 | DeLuca et al. |
| 6,248,115 | B1 | 6/2001 | Halk |
| 6,287,252 | B1 | 9/2001 | Lugo |
| 6,290,707 | B1 | 9/2001 | Street |
| 6,315,719 | B1 | 11/2001 | Rode et al. |
| 6,379,237 | B1 | 4/2002 | Gordon |
| 6,385,473 | B1 | 5/2002 | Haines et al. |
| 6,389,308 | B1 | 5/2002 | Shusterman |
| 6,416,471 | B1 | 7/2002 | Kumar et al. |
| 6,453,186 | B1 | 7/2002 | Lovejoy et al. |
| 6,434,410 | B1 | 8/2002 | Cordero et al. |
| 6,441,747 | B1 | 8/2002 | Khair et al. |
| 6,454,708 | B1 | 9/2002 | Ferguson et al. |
| 6,456,871 | B1 | 9/2002 | Hsu et al. |
| 6,456,872 | B1 | 9/2002 | Faisandier |
| 6,464,815 | B1 | 10/2002 | Beaudry |
| 6,493,898 | B1 | 12/2002 | Woods et al. |
| 6,496,705 | B1 | 12/2002 | Ng et al. |
| 6,510,339 | B2 | 1/2003 | Kovtun et al. |
| 6,546,285 | B1 | 4/2003 | Owen et al. |
| 6,564,090 | B2 | 5/2003 | Taha et al. |
| 6,569,095 | B2 | 5/2003 | Eggers |
| 6,577,893 | B1 | 6/2003 | Besson et al. |
| 6,580,942 | B1 | 6/2003 | Willshire |
| 6,585,707 | B2 | 7/2003 | Cabiri et al. |
| 6,589,170 | B1 | 7/2003 | Flach et al. |
| 6,589,187 | B1 | 7/2003 | Dimberger et al. |
| 6,605,046 | B1 | 8/2003 | Del Mar et al. |
| 6,615,083 | B2 | 9/2003 | Kupper |

(56) References Cited

U.S. PATENT DOCUMENTS

| | | |
|---|---|---|
| 6,622,035 B1 | 9/2003 | Merilainen |
| 6,626,865 B1 | 9/2003 | Prisell |
| 6,656,125 B2 | 12/2003 | Misczynski et al. |
| 6,664,893 B1 | 12/2003 | Eveland et al. |
| 6,665,385 B2 | 12/2003 | Rogers et al. |
| 6,690,959 B2 | 2/2004 | Thompson |
| 6,694,177 B2 | 2/2004 | Eggers et al. |
| 6,701,184 B2 | 3/2004 | Henkin |
| 6,711,427 B1 | 3/2004 | Ketelhohn |
| 6,730,028 B2 | 5/2004 | Eppstein |
| D492,607 S | 7/2004 | Curkovic et al. |
| 6,773,396 B2 | 8/2004 | Flach et al. |
| 6,775,566 B2 | 8/2004 | Nissila |
| 6,801,137 B2 | 10/2004 | Eggers |
| 6,801,802 B2 | 10/2004 | Sitzman et al. |
| 6,871,089 B2 | 3/2005 | Korzinov et al. |
| 6,871,211 B2 | 3/2005 | Labounty et al. |
| 6,875,174 B2 | 4/2005 | Braun et al. |
| 6,881,191 B2 | 4/2005 | Oakley et al. |
| 6,893,396 B2 | 5/2005 | Schulze et al. |
| 6,897,788 B2 | 5/2005 | Khair et al. |
| 6,904,312 B2 | 6/2005 | Bardy |
| 6,925,324 B2 | 8/2005 | Shusterman |
| 6,940,403 B2 | 9/2005 | Kail |
| 6,954,163 B2 | 10/2005 | Toumazou et al. |
| 6,957,107 B2 | 10/2005 | Rogers et al. |
| 6,987,965 B2 | 1/2006 | Ng et al. |
| 7,002,468 B2 | 2/2006 | Eveland et al. |
| 7,020,508 B2 | 3/2006 | Stivoric et al. |
| 7,024,248 B2 | 4/2006 | Penner et al. |
| 7,031,770 B2 | 4/2006 | Collins et al. |
| 7,072,708 B1 | 7/2006 | Andresen et al. |
| 7,072,709 B2 | 7/2006 | Xue |
| 7,076,283 B2 | 7/2006 | Cho et al. |
| 7,076,287 B2 | 7/2006 | Rowlandson |
| 7,076,288 B2 | 7/2006 | Skinner |
| 7,076,289 B2 | 7/2006 | Sarkar et al. |
| 7,079,977 B2 | 7/2006 | Osorio et al. |
| 7,082,327 B2 | 7/2006 | Houben |
| 7,089,048 B2 | 8/2006 | Matsumura et al. |
| 7,099,715 B2 | 8/2006 | Korzinov et al. |
| 7,117,031 B2 | 10/2006 | Lohman et al. |
| 7,120,485 B2 | 10/2006 | Glass et al. |
| 7,130,396 B2 | 10/2006 | Rogers et al. |
| 7,161,484 B2 | 1/2007 | Tsoukalis |
| 7,171,166 B2 | 1/2007 | Ng et al. |
| 7,179,152 B1 | 2/2007 | Rhoades |
| 7,186,264 B2 | 3/2007 | Liddicoat et al. |
| 7,193,264 B2 | 3/2007 | Lande |
| 7,194,300 B2 | 3/2007 | Korzinov |
| 7,206,630 B1 | 4/2007 | Tarler |
| 7,212,850 B2 | 5/2007 | Prystowsky et al. |
| 7,222,054 B2 | 5/2007 | Geva |
| 7,242,318 B2 | 7/2007 | Harris |
| 7,266,361 B2 | 9/2007 | Burdett |
| 7,316,671 B2 | 1/2008 | Lastovich et al. |
| 7,349,947 B1 | 3/2008 | Slage et al. |
| D567,949 S | 4/2008 | Lash et al. |
| 7,354,423 B2 | 4/2008 | Zelickson et al. |
| 7,387,607 B2 | 6/2008 | Holt et al. |
| 7,444,177 B2 | 10/2008 | Nazeri |
| D584,414 S | 1/2009 | Lash et al. |
| 7,477,933 B2 | 1/2009 | Ueyama |
| 7,478,108 B2 | 1/2009 | Townsend et al. |
| 7,481,772 B2 | 1/2009 | Banet |
| 7,482,314 B2 | 1/2009 | Grimes et al. |
| 7,502,643 B2 | 3/2009 | Farringdon et al. |
| 7,539,533 B2 | 5/2009 | Tran |
| 7,542,878 B2 | 6/2009 | Nanikashvili |
| D600,351 S | 9/2009 | Phillips et al. |
| 7,587,237 B2 | 9/2009 | Korzinov et al. |
| 7,630,756 B2 | 12/2009 | Linker |
| 7,632,174 B2 | 12/2009 | Gringer et al. |
| D607,570 S | 1/2010 | Phillips et al. |
| 7,672,714 B2 | 3/2010 | Kuo et al. |
| 7,715,905 B2 | 5/2010 | Kurzweil et al. |
| D618,357 S | 6/2010 | Navies |
| 7,729,753 B2 | 6/2010 | Kremliovsky et al. |
| 7,733,224 B2 | 6/2010 | Tran |
| D621,048 S | 8/2010 | Severe et al. |
| 7,815,494 B2 | 10/2010 | Gringer et al. |
| 7,841,039 B1 | 11/2010 | Squire |
| 7,889,070 B2 | 2/2011 | Reeves et al. |
| 7,894,888 B2 | 2/2011 | Chan et al. |
| D634,431 S | 3/2011 | Severe et al. |
| 7,904,133 B2 | 3/2011 | Gehman et al. |
| 7,907,956 B2 | 3/2011 | Uhlik |
| 7,907,996 B2 | 3/2011 | Prystowsky et al. |
| 7,941,207 B2 | 5/2011 | Korzinov |
| D639,437 S | 6/2011 | Bishay et al. |
| 7,970,450 B2 | 6/2011 | Kroecker et al. |
| 7,979,111 B2 | 7/2011 | Acquista |
| 7,996,075 B2 | 8/2011 | Korzinov et al. |
| 7,996,187 B2 | 8/2011 | Nanikashvili et al. |
| 8,002,701 B2 | 8/2011 | John et al. |
| D645,968 S | 9/2011 | Kasabach et al. |
| D650,911 S | 12/2011 | Odeh |
| 8,077,042 B2 | 12/2011 | Peeters |
| 8,103,333 B2 | 1/2012 | Tran |
| 8,108,036 B2 | 1/2012 | Tran |
| 8,170,639 B2 | 1/2012 | Hauge |
| 8,116,841 B2 | 2/2012 | Bly et al. |
| 8,150,502 B2 | 4/2012 | Kumar et al. |
| 8,156,945 B2 | 4/2012 | Hart |
| 8,160,682 B2 | 4/2012 | Kumar et al. |
| D659,836 S | 5/2012 | Bensch et al. |
| 8,200,319 B2 | 6/2012 | Pu et al. |
| D663,432 S | 7/2012 | Nichols |
| 8,214,007 B2 | 7/2012 | Baker et al. |
| 8,244,335 B2 | 8/2012 | Kumar et al. |
| 8,249,686 B2 | 8/2012 | Libbus et al. |
| 8,261,754 B2 | 9/2012 | Pitstick |
| 8,265,907 B2 | 9/2012 | Nanikashvili et al. |
| RE43,767 E | 10/2012 | Eggers et al. |
| 8,280,749 B2 | 10/2012 | Hsieh et al. |
| 8,285,356 B2 | 10/2012 | Bly et al. |
| 8,290,129 B2 | 10/2012 | Rogers et al. |
| 8,290,574 B2 | 10/2012 | Field et al. |
| 8,301,219 B2 | 10/2012 | Chen et al. |
| 8,301,236 B2 | 10/2012 | Baumann et al. |
| 8,311,604 B2 | 11/2012 | Rowlandson et al. |
| 8,315,687 B2 | 11/2012 | Cross et al. |
| 8,315,695 B2 | 11/2012 | Sebelius et al. |
| 8,323,188 B2 | 12/2012 | Tran |
| 8,326,394 B2 | 12/2012 | Rowlandson et al. |
| 8,326,407 B2 | 12/2012 | Linker |
| 8,328,718 B2 | 12/2012 | Tran |
| D674,009 S | 1/2013 | Nichols |
| 8,343,116 B2 | 1/2013 | Ignon |
| 8,369,936 B2 | 2/2013 | Farringdon et al. |
| 8,374,688 B2 | 2/2013 | Libbus et al. |
| 8,386,009 B2 | 2/2013 | Lindberg et al. |
| 8,388,543 B2 | 3/2013 | Chon et al. |
| 8,406,843 B2 | 3/2013 | Tiegs et al. |
| 8,412,317 B2 | 4/2013 | Mazar |
| 8,417,326 B2 | 4/2013 | Chon et al. |
| 8,425,414 B2 | 4/2013 | Eveland |
| D682,437 S | 5/2013 | Olson et al. |
| 8,449,471 B2 | 5/2013 | Tran |
| 8,452,356 B2 | 5/2013 | Vestel et al. |
| 8,460,189 B2 | 6/2013 | Libbus et al. |
| 8,473,039 B2 | 6/2013 | Michelson et al. |
| 8,473,047 B2 | 6/2013 | Chakravarthy et al. |
| 8,478,418 B2 | 7/2013 | Fahey |
| 8,483,809 B2 | 7/2013 | Kim et al. |
| 8,500,636 B2 | 8/2013 | Tran |
| 8,515,529 B2 | 8/2013 | Pu et al. |
| 8,525,673 B2 | 9/2013 | Tran |
| 8,535,223 B2 | 9/2013 | Corroy et al. |
| 8,538,503 B2 | 9/2013 | Kumar et al. |
| 8,540,731 B2 | 9/2013 | Kay |
| 8,560,046 B2 | 10/2013 | Kumar et al. |
| 8,562,527 B2 | 10/2013 | Braun et al. |
| 8,571,645 B2 | 10/2013 | Wu et al. |

(56) References Cited

U.S. PATENT DOCUMENTS

| | | |
|---|---|---|
| 8,588,908 B2 | 11/2013 | Moorman et al. |
| 8,591,430 B2 | 11/2013 | Amurthur et al. |
| 8,591,599 B1 | 11/2013 | Kaliki |
| 8,594,763 B1 | 11/2013 | Bibian |
| 8,626,262 B2 | 1/2014 | McGusty et al. |
| 8,639,319 B2 | 1/2014 | Hugh et al. |
| 8,668,643 B2 | 3/2014 | Kinast |
| 8,684,900 B2 | 4/2014 | Tran |
| 8,684,925 B2 | 4/2014 | Amurthur et al. |
| 8,688,189 B2 | 4/2014 | Shennib |
| 8,688,190 B2 | 4/2014 | Libbus et al. |
| 8,688,202 B2 | 4/2014 | Brockway et al. |
| 8,718,742 B2 | 5/2014 | Beck et al. |
| 8,718,752 B2 | 5/2014 | Libbus et al. |
| 8,718,753 B2 | 5/2014 | Chon et al. |
| 8,731,632 B1 | 5/2014 | Sereboff et al. |
| 8,738,118 B2 | 5/2014 | Moon et al. |
| 8,744,561 B2 | 6/2014 | Fahey |
| 8,755,876 B2 | 6/2014 | Chon et al. |
| 8,782,308 B2 | 7/2014 | Vlach |
| 8,789,727 B2 | 7/2014 | Mortazavi |
| 8,790,257 B2 | 7/2014 | Libbus et al. |
| 8,795,174 B2 | 8/2014 | Manicka et al. |
| 8,818,481 B2 | 8/2014 | Bly et al. |
| 8,823,490 B2 | 9/2014 | Libbus et al. |
| 8,838,218 B2 | 9/2014 | Khair |
| 8,858,450 B2 | 10/2014 | Chon et al. |
| 8,874,185 B2 | 10/2014 | Sonnenborg |
| D719,267 S | 12/2014 | Vaccarella |
| 8,903,477 B2 | 12/2014 | Berkner |
| 8,903,484 B2 | 12/2014 | Mazar |
| 8,909,328 B2 | 12/2014 | Chon |
| 8,909,330 B2 | 12/2014 | McCombie et al. |
| 8,909,332 B2 | 12/2014 | Vitali et al. |
| 8,909,333 B2 | 12/2014 | Rossi |
| 8,909,832 B2 | 12/2014 | Vlach et al. |
| 8,926,509 B2 | 1/2015 | Magar et al. |
| 8,945,019 B2 | 2/2015 | Prystowsky et al. |
| 8,948,854 B2 | 2/2015 | Friedman et al. |
| 8,954,129 B1 | 2/2015 | Schlegel et al. |
| 8,956,293 B2 | 2/2015 | McCombie et al. |
| 8,968,195 B2 | 3/2015 | Tran |
| 8,972,000 B2 | 3/2015 | Manera |
| 8,979,755 B2 | 3/2015 | Szydlo-Moore et al. |
| 9,014,777 B2 | 4/2015 | Woo |
| 9,015,008 B2 | 4/2015 | Geva et al. |
| 9,017,255 B2 | 4/2015 | Raptis et al. |
| 9,017,256 B2 | 4/2015 | Gottesman |
| 9,021,161 B2 | 4/2015 | Vlach et al. |
| 9,021,165 B2 | 4/2015 | Vlach |
| 9,026,190 B2 | 5/2015 | Shenasa et al. |
| 9,037,223 B2 | 5/2015 | Oral et al. |
| 9,044,148 B2 | 6/2015 | Michelson et al. |
| 9,084,548 B2 | 7/2015 | Bouguerra |
| 9,095,274 B2 | 8/2015 | Fein et al. |
| 9,101,264 B2 | 8/2015 | Acquista |
| 9,138,144 B2 | 9/2015 | Geva |
| 9,149,228 B2 | 10/2015 | Kinast |
| 9,173,670 B2 | 11/2015 | Sepulveda et al. |
| 9,179,851 B2 | 11/2015 | Baumann et al. |
| D744,659 S | 12/2015 | Bishay et al. |
| 9,211,076 B2 | 12/2015 | Kim |
| 9,226,679 B2 | 1/2016 | Balda |
| 9,241,649 B2 | 1/2016 | Kumar et al. |
| 9,241,650 B2 | 1/2016 | Amirim |
| 9,277,864 B2 | 3/2016 | Yang et al. |
| 9,282,894 B2 | 3/2016 | Banet et al. |
| 9,307,921 B2 | 4/2016 | Friedman et al. |
| 9,345,414 B1 | 5/2016 | Bardy et al. |
| 9,355,215 B2 | 5/2016 | Vlach |
| D759,653 S | 6/2016 | Toth et al. |
| 9,357,939 B1 | 6/2016 | Nosrati |
| 9,364,150 B2 | 6/2016 | Sebelius et al. |
| 9,364,155 B2 | 6/2016 | Bardy et al. |
| 9,398,853 B2 | 7/2016 | Nanikashvili |
| 9,408,545 B2 | 8/2016 | Felix et al. |
| 9,408,551 B2 | 8/2016 | Bardy et al. |
| 9,408,576 B2 | 8/2016 | Chon et al. |
| 9,414,753 B2 | 8/2016 | Chon et al. |
| 9,414,786 B1 | 8/2016 | Brockway et al. |
| D766,447 S | 9/2016 | Bishay et al. |
| 9,433,367 B2 | 9/2016 | Felix et al. |
| 9,433,380 B1 | 9/2016 | Bishay et al. |
| 9,451,890 B2 | 9/2016 | Gitlin et al. |
| 9,451,975 B2 | 9/2016 | Sepulveda et al. |
| 9,474,445 B2 | 10/2016 | Eveland |
| 9,474,461 B2 | 10/2016 | Fisher et al. |
| 9,478,998 B1 | 10/2016 | Lapetina et al. |
| D773,056 S | 11/2016 | Vlach |
| 9,492,084 B2 | 11/2016 | Behar et al. |
| 9,504,423 B1 | 11/2016 | Bardy et al. |
| D775,361 S | 12/2016 | Vosch et al. |
| 9,510,764 B2 | 12/2016 | Li et al. |
| 9,510,768 B2 | 12/2016 | Rossi |
| 9,526,433 B2 | 12/2016 | Lapetina et al. |
| 9,545,204 B2 | 1/2017 | Bishay et al. |
| 9,545,228 B2 | 1/2017 | Bardy et al. |
| 9,554,715 B2 | 1/2017 | Bardy et al. |
| 9,579,020 B2 | 2/2017 | Libbus et al. |
| D780,914 S | 3/2017 | Kyvik et al. |
| 9,585,584 B2 | 3/2017 | Marek et al. |
| 9,597,004 B2 | 3/2017 | Hughes et al. |
| 9,615,763 B2 | 4/2017 | Felix et al. |
| 9,615,793 B2 | 4/2017 | Solosko et al. |
| 9,619,660 B1 | 4/2017 | Felix et al. |
| 9,642,537 B2 | 5/2017 | Felix et al. |
| 9,655,518 B2 | 5/2017 | Lin |
| 9,655,537 B2 | 5/2017 | Bardy et al. |
| 9,655,538 B2 | 5/2017 | Felix |
| 9,662,030 B2 | 5/2017 | Thng et al. |
| 9,675,264 B2 | 6/2017 | Acquista et al. |
| 9,700,227 B2 | 6/2017 | Bishay et al. |
| 9,706,938 B2 | 7/2017 | Chakravarthy et al. |
| 9,706,956 B2 | 7/2017 | Brockway et al. |
| 9,713,428 B2 | 7/2017 | Chon et al. |
| D793,566 S | 8/2017 | Bishay et al. |
| D794,812 S | 8/2017 | Matsushita |
| 9,717,432 B2 | 8/2017 | Bardy et al. |
| 9,717,433 B2 | 8/2017 | Felix et al. |
| 9,730,593 B2 | 8/2017 | Bardy et al. |
| 9,730,604 B2 | 8/2017 | Li et al. |
| 9,730,641 B2 | 8/2017 | Felix et al. |
| 9,736,625 B1 | 8/2017 | Landgraf et al. |
| 9,737,211 B2 | 8/2017 | Bardy et al. |
| 9,737,224 B2 | 8/2017 | Bardy et al. |
| D797,301 S | 9/2017 | Chen |
| D797,943 S | 9/2017 | Long |
| D798,170 S | 9/2017 | Toth et al. |
| D798,294 S | 9/2017 | Toth et al. |
| 9,775,534 B2 | 10/2017 | Korzinov et al. |
| 9,775,536 B2 | 10/2017 | Felix et al. |
| 9,782,095 B2 | 10/2017 | Ylostalo et al. |
| 9,782,132 B2 | 10/2017 | Golda et al. |
| 9,788,722 B2 | 10/2017 | Bardy et al. |
| 9,801,562 B1 | 10/2017 | Host-Madsen |
| 9,820,665 B2 | 11/2017 | Felix et al. |
| 9,839,363 B2 | 12/2017 | Albert |
| D810,308 S | 2/2018 | Lind et al. |
| D811,610 S | 2/2018 | Abel et al. |
| D811,611 S | 2/2018 | Lind et al. |
| D811,615 S | 2/2018 | Lind et al. |
| 9,888,866 B2 | 2/2018 | Chon et al. |
| 9,901,274 B2 | 2/2018 | Bishay et al. |
| 9,907,478 B2 | 3/2018 | Friedman et al. |
| 9,936,875 B2 | 4/2018 | Bardy et al. |
| 9,955,885 B2 | 5/2018 | Felix et al. |
| 9,955,887 B2 | 5/2018 | Hughes et al. |
| 9,955,888 B2 | 5/2018 | Felix et al. |
| 9,955,911 B2 | 5/2018 | Bardy et al. |
| 9,968,274 B2 | 5/2018 | Korzinov et al. |
| 9,986,921 B2 | 6/2018 | Chon et al. |
| 10,004,415 B2 | 6/2018 | Bishay et al. |
| D823,466 S | 7/2018 | Marogil |
| D824,526 S | 7/2018 | Ramjit et al. |

(56) References Cited

U.S. PATENT DOCUMENTS

| | | |
|---|---|---|
| 10,045,709 B2 | 8/2018 | Bardy et al. |
| 10,052,022 B2 | 8/2018 | Bardy et al. |
| 10,076,257 B2 | 9/2018 | Lin et al. |
| 10,095,841 B2 | 10/2018 | Dettinger et al. |
| 10,098,559 B2 | 10/2018 | Hughes et al. |
| 10,111,601 B2 | 10/2018 | Bishay et al. |
| 10,123,703 B2 | 11/2018 | Bardy et al. |
| 10,154,793 B2 | 12/2018 | Felix et al. |
| 10,165,946 B2 | 1/2019 | Bardy et al. |
| 10,172,534 B2 | 1/2019 | Felix et al. |
| 10,176,575 B2 | 1/2019 | Isgum et al. |
| 10,251,575 B2 | 4/2019 | Bardy et al. |
| 10,251,576 B2 | 4/2019 | Bardy et al. |
| 10,264,992 B2 | 4/2019 | Felix et al. |
| 10,265,015 B2 | 4/2019 | Bardy et al. |
| 10,270,898 B2 | 4/2019 | Soli et al. |
| 10,271,754 B2 | 4/2019 | Bahney et al. |
| 10,271,755 B2 | 4/2019 | Felix et al. |
| 10,271,756 B2 | 4/2019 | Felix et al. |
| 10,278,603 B2 | 5/2019 | Felix et al. |
| 10,278,606 B2 | 5/2019 | Bishay et al. |
| 10,278,607 B2 | 5/2019 | Prystowsky et al. |
| 10,299,691 B2 | 5/2019 | Hughes et al. |
| 10,321,823 B2 | 6/2019 | Chakravarthy et al. |
| 10,327,657 B2 | 6/2019 | Spencer et al. |
| D852,965 S | 7/2019 | Bahney et al. |
| D854,167 S | 7/2019 | Bahney et al. |
| 10,362,467 B2 | 7/2019 | Landgraf et al. |
| 10,368,808 B2 | 8/2019 | Lee et al. |
| 10,376,172 B2 | 8/2019 | Kuppuraj et al. |
| 10,390,700 B2 | 8/2019 | Bardy et al. |
| 10,398,344 B2 | 9/2019 | Felix et al. |
| 10,405,799 B2 | 9/2019 | Kumar et al. |
| 10,413,205 B2 | 9/2019 | Bardy et al. |
| 10,426,634 B1 | 10/2019 | Al-Jazaeri et al. |
| 10,433,743 B1 | 10/2019 | Felix et al. |
| 10,433,748 B2 | 10/2019 | Bishay et al. |
| 10,433,751 B2 | 10/2019 | Bardy et al. |
| 10,441,184 B2 | 10/2019 | Baumann et al. |
| 10,463,269 B2 | 11/2019 | Boleyn et al. |
| 10,478,083 B2 | 11/2019 | Felix et al. |
| 10,499,812 B2 | 12/2019 | Bardy et al. |
| 10,517,500 B2 | 12/2019 | Kumar et al. |
| 10,555,683 B2 | 2/2020 | Bahney et al. |
| 10,561,326 B2 | 2/2020 | Felix et al. |
| 10,561,328 B2 | 2/2020 | Bishay |
| 10,568,533 B2 | 2/2020 | Soli et al. |
| 10,588,527 B2 | 3/2020 | McNamara et al. |
| 10,595,371 B2 | 3/2020 | Gopalakrishnan et al. |
| 10,602,942 B2 | 3/2020 | Shakur et al. |
| 10,602,977 B2 | 3/2020 | Bardy et al. |
| 10,624,551 B2 | 4/2020 | Bardy et al. |
| 10,660,520 B2 | 5/2020 | Lin |
| 10,667,712 B2 | 6/2020 | Park et al. |
| 10,729,361 B2 | 8/2020 | Hoppe et al. |
| 10,758,139 B2 | 9/2020 | Rapin et al. |
| 10,772,521 B2 | 9/2020 | Korzinov et al. |
| 10,779,744 B2 | 9/2020 | Rapin et al. |
| 10,813,565 B2 | 10/2020 | Park et al. |
| 10,827,938 B2 | 11/2020 | Fontanarava et al. |
| 10,866,619 B1 | 12/2020 | Bushnell et al. |
| 10,869,610 B2 | 12/2020 | Lu et al. |
| 10,987,018 B2 | 4/2021 | Aga et al. |
| 11,004,198 B2 | 5/2021 | Isgum et al. |
| 11,017,887 B2 | 5/2021 | Finkelmeier et al. |
| 11,026,632 B2 | 6/2021 | Narasimhan et al. |
| 11,051,738 B2 | 7/2021 | Bahney et al. |
| 11,051,743 B2 | 7/2021 | Felix et al. |
| 11,062,804 B2 | 7/2021 | Selvaraj et al. |
| 11,083,371 B1 | 8/2021 | Szabados et al. |
| 11,141,091 B2 | 10/2021 | Uday et al. |
| 11,172,882 B2 | 11/2021 | Upadhya et al. |
| 11,246,523 B1 | 2/2022 | Abercrombie, II et al. |
| 11,246,524 B2 | 2/2022 | Szabados et al. |
| 11,253,185 B2 | 2/2022 | Szabados et al. |
| 11,253,186 B2 | 2/2022 | Szabados et al. |
| 11,276,491 B2 | 3/2022 | Petterson et al. |
| 11,289,197 B1 | 3/2022 | Park et al. |
| 11,324,420 B2 | 5/2022 | Selvaraj et al. |
| 11,324,441 B2 | 5/2022 | Bardy et al. |
| 11,331,034 B2 | 5/2022 | Rapin et al. |
| 11,337,632 B2 | 5/2022 | Abercrombie, II et al. |
| 11,350,864 B2 | 7/2022 | Abercrombie, II et al. |
| 11,350,865 B2 | 7/2022 | Abercrombie, II et al. |
| 11,375,941 B2 | 7/2022 | Szabados et al. |
| 11,382,555 B2 | 7/2022 | Szabados et al. |
| 11,399,760 B2 | 8/2022 | Abercrombie, II et al. |
| 11,445,967 B2 | 9/2022 | Felix et al. |
| 11,497,432 B2 | 11/2022 | Szabados et al. |
| 11,504,041 B2 | 11/2022 | Abercrombie, II et al. |
| 11,589,792 B1 | 2/2023 | Abercrombie, II et al. |
| 11,605,458 B2 | 3/2023 | Park et al. |
| 11,627,902 B2 | 4/2023 | Bahney et al. |
| 11,660,037 B2 | 5/2023 | Felix et al. |
| D988,518 S | 6/2023 | Levy et al. |
| 11,678,832 B2 | 6/2023 | Boleyn et al. |
| 11,751,789 B2 | 9/2023 | Abercrombie, II et al. |
| 11,756,684 B2 | 9/2023 | Park et al. |
| 11,806,150 B2 | 11/2023 | Abercrombie, II et al. |
| D1,012,295 S | 1/2024 | Peremen et al. |
| 11,925,469 B2 | 3/2024 | Szabados et al. |
| 2001/0056262 A1 | 12/2001 | Cabiri et al. |
| 2002/0007126 A1 | 1/2002 | Nissila |
| 2002/0026112 A1 | 2/2002 | Nissila et al. |
| 2002/0067256 A1 | 6/2002 | Kail |
| 2002/0082491 A1 | 6/2002 | Nissila |
| 2002/0087167 A1 | 7/2002 | Winitsky |
| 2002/0180605 A1 | 12/2002 | Ozguz et al. |
| 2003/0069510 A1 | 4/2003 | Semler |
| 2003/0083559 A1 | 5/2003 | Thompson |
| 2003/0125786 A1 | 7/2003 | Gliner |
| 2003/0149349 A1 | 8/2003 | Jensen |
| 2003/0176795 A1 | 9/2003 | Harris et al. |
| 2003/0195408 A1 | 10/2003 | Hastings |
| 2003/0199811 A1 | 10/2003 | Sage, Jr. et al. |
| 2003/0212319 A1 | 11/2003 | Magill |
| 2004/0032957 A1 | 2/2004 | Mansy et al. |
| 2004/0068195 A1 | 4/2004 | Massicotte et al. |
| 2004/0077954 A1 | 4/2004 | Oakley et al. |
| 2004/0082843 A1 | 4/2004 | Menon |
| 2004/0187297 A1 | 9/2004 | Su |
| 2004/0199063 A1 | 10/2004 | O'Neil |
| 2004/0215091 A1 | 10/2004 | Lohman et al. |
| 2004/0236202 A1 | 11/2004 | Burton |
| 2004/0254587 A1 | 12/2004 | Park |
| 2004/0260189 A1 | 12/2004 | Eggers et al. |
| 2005/0096513 A1 | 5/2005 | Ozguz et al. |
| 2005/0101875 A1 | 5/2005 | Semler et al. |
| 2005/0118246 A1 | 6/2005 | Wong et al. |
| 2005/0119580 A1 | 6/2005 | Eveland |
| 2005/0165323 A1 | 7/2005 | Montgomery et al. |
| 2005/0204636 A1 | 9/2005 | Azar et al. |
| 2005/0277841 A1 | 12/2005 | Shennib |
| 2005/0280531 A1 | 12/2005 | Fadem et al. |
| 2006/0030781 A1 | 2/2006 | Shennib |
| 2006/0030782 A1 | 2/2006 | Shennib |
| 2006/0047215 A1 | 3/2006 | Newman et al. |
| 2006/0084883 A1 | 4/2006 | Linker |
| 2006/0142648 A1 | 6/2006 | Banet et al. |
| 2006/0142654 A1 | 6/2006 | Rytky |
| 2006/0149156 A1 | 7/2006 | Cochran et al. |
| 2006/0155173 A1 | 7/2006 | Anttila et al. |
| 2006/0155183 A1 | 7/2006 | Kroecker et al. |
| 2006/0155199 A1 | 7/2006 | Logier et al. |
| 2006/0155200 A1 | 7/2006 | Ng et al. |
| 2006/0161064 A1 | 7/2006 | Watrous et al. |
| 2006/0161065 A1 | 7/2006 | Elion |
| 2006/0161066 A1 | 7/2006 | Elion |
| 2006/0161067 A1 | 7/2006 | Elion |
| 2006/0161068 A1 | 7/2006 | Hastings et al. |
| 2006/0167353 A1 | 7/2006 | Nazeri |
| 2006/0224072 A1 | 10/2006 | Shennib |
| 2006/0264767 A1 | 11/2006 | Shennib |
| 2007/0003695 A1 | 1/2007 | Tregub et al. |

(56) References Cited

U.S. PATENT DOCUMENTS

| | | |
|---|---|---|
| 2007/0010729 A1 | 1/2007 | Virtanen |
| 2007/0027388 A1 | 2/2007 | Chou |
| 2007/0088419 A1 | 4/2007 | Florina et al. |
| 2007/0156054 A1 | 7/2007 | Korzinov et al. |
| 2007/0208266 A1 | 9/2007 | Hadley |
| 2007/0225611 A1 | 9/2007 | Kumar et al. |
| 2007/0249946 A1 | 10/2007 | Kumar et al. |
| 2007/0255153 A1 | 11/2007 | Kumar et al. |
| 2007/0270678 A1 | 11/2007 | Fadem et al. |
| 2007/0285868 A1 | 12/2007 | Lindberg et al. |
| 2007/0293776 A1 | 12/2007 | Korzinov et al. |
| 2008/0039730 A1 | 2/2008 | Pu et al. |
| 2008/0091089 A1 | 4/2008 | Guillory et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0167567 A1 | 7/2008 | Bashour et al. |
| 2008/0214901 A1 | 9/2008 | Gehman et al. |
| 2008/0275327 A1 | 11/2008 | Faarbaek et al. |
| 2008/0281215 A1 | 11/2008 | Alhussiny |
| 2008/0288026 A1 | 11/2008 | Cross et al. |
| 2008/0309287 A1 | 12/2008 | Reed |
| 2009/0048556 A1 | 2/2009 | Durano |
| 2009/0062670 A1 | 3/2009 | Sterling et al. |
| 2009/0062671 A1 | 3/2009 | Brockway |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0182204 A1 | 7/2009 | Semler et al. |
| 2009/0253975 A1 | 10/2009 | Tiegs |
| 2009/0283300 A1 | 11/2009 | Grunthaner |
| 2009/0292193 A1 | 11/2009 | Wijesiriwardana |
| 2009/0292194 A1 | 11/2009 | Libbus et al. |
| 2009/0306485 A1 | 12/2009 | Bell |
| 2010/0001541 A1 | 1/2010 | Sugiyama |
| 2010/0022864 A1 | 1/2010 | Cordero |
| 2010/0042113 A1 | 2/2010 | Mah |
| 2010/0049006 A1 | 2/2010 | Magar et al. |
| 2010/0051039 A1 | 3/2010 | Ferrara |
| 2010/0056881 A1 | 3/2010 | Libbus et al. |
| 2010/0057056 A1 | 3/2010 | Gurtner |
| 2010/0076533 A1 | 3/2010 | Dar et al. |
| 2010/0081913 A1 | 4/2010 | Cross et al. |
| 2010/0145359 A1 | 6/2010 | Keller |
| 2010/0191310 A1 | 7/2010 | Bly |
| 2010/0234716 A1 | 9/2010 | Engel |
| 2010/0249625 A1 | 9/2010 | Lin |
| 2010/0268103 A1 | 10/2010 | McNamara et al. |
| 2010/0312131 A1 | 12/2010 | Naware et al. |
| 2010/0331711 A1 | 12/2010 | Krauss et al. |
| 2011/0021937 A1 | 1/2011 | Hugh et al. |
| 2011/0087083 A1 | 4/2011 | Poeze et al. |
| 2011/0098583 A1 | 4/2011 | Pandia et al. |
| 2011/0119212 A1 | 5/2011 | De Bruin et al. |
| 2011/0144470 A1 | 6/2011 | Mazar et al. |
| 2011/0160601 A1 | 6/2011 | Wang et al. |
| 2011/0166468 A1 | 7/2011 | Prystowsky et al. |
| 2011/0190650 A1 | 8/2011 | McNair |
| 2011/0218415 A1 | 9/2011 | Chen |
| 2011/0237922 A1 | 9/2011 | Parker, III et al. |
| 2011/0237924 A1 | 9/2011 | McGusty et al. |
| 2011/0251504 A1 | 10/2011 | Tereshchenko et al. |
| 2011/0279963 A1 | 11/2011 | Kumar et al. |
| 2011/0306862 A1 | 12/2011 | Hayes-Gill |
| 2012/0029307 A1 | 2/2012 | Paquet et al. |
| 2012/0071730 A1 | 3/2012 | Romero |
| 2012/0071731 A1 | 3/2012 | Gottesman |
| 2012/0071743 A1 | 3/2012 | Todorov et al. |
| 2012/0083670 A1 | 4/2012 | Rotondo et al. |
| 2012/0088999 A1 | 4/2012 | Bishay et al. |
| 2012/0101396 A1 | 4/2012 | Solosko et al. |
| 2012/0108917 A1 | 5/2012 | Libbus et al. |
| 2012/0108920 A1 | 5/2012 | Bly et al. |
| 2012/0110226 A1 | 5/2012 | Vlach et al. |
| 2012/0110228 A1 | 5/2012 | Vlach et al. |
| 2012/0133162 A1 | 5/2012 | Sgobero |
| 2012/0172676 A1 | 7/2012 | Penders et al. |
| 2012/0197150 A1 | 8/2012 | Cao et al. |
| 2012/0209102 A1 | 8/2012 | Ylotalo et al. |
| 2012/0209126 A1 | 8/2012 | Amos et al. |
| 2012/0215123 A1 | 8/2012 | Kumar et al. |
| 2012/0220835 A1 | 8/2012 | Chung |
| 2012/0259233 A1 | 10/2012 | Chan et al. |
| 2012/0271141 A1 | 10/2012 | Davies |
| 2012/0310070 A1 | 12/2012 | Kumar et al. |
| 2012/0316532 A1* | 12/2012 | McCormick ...... A61F 13/51104 604/385.01 |
| 2012/0323257 A1 | 12/2012 | Sutton |
| 2012/0330126 A1 | 12/2012 | Hoppe et al. |
| 2013/0023816 A1 | 1/2013 | Bachinski et al. |
| 2013/0041273 A1 | 2/2013 | Houben et al. |
| 2013/0046151 A1 | 2/2013 | Bsoul et al. |
| 2013/0085347 A1 | 4/2013 | Manicka et al. |
| 2013/0096395 A1 | 4/2013 | Katra et al. |
| 2013/0116533 A1 | 5/2013 | Lian et al. |
| 2013/0116585 A1 | 5/2013 | Bouguerra |
| 2013/0144146 A1 | 6/2013 | Linker |
| 2013/0150698 A1 | 6/2013 | Hsu et al. |
| 2013/0158494 A1 | 6/2013 | Ong |
| 2013/0172763 A1 | 7/2013 | Wheeler |
| 2013/0184662 A1 | 7/2013 | Aali et al. |
| 2013/0191035 A1 | 7/2013 | Chon et al. |
| 2013/0225938 A1 | 8/2013 | Vlach |
| 2013/0225967 A1 | 8/2013 | Esposito |
| 2013/0226018 A1 | 8/2013 | Kumar et al. |
| 2013/0245415 A1 | 9/2013 | Kumar et al. |
| 2013/0245472 A1 | 9/2013 | Eveland |
| 2013/0253285 A1 | 9/2013 | Bly et al. |
| 2013/0274584 A1 | 10/2013 | Finlay et al. |
| 2013/0296680 A1 | 11/2013 | Linker |
| 2013/0300575 A1 | 11/2013 | Kurzweil et al. |
| 2013/0324868 A1 | 12/2013 | Kaib et al. |
| 2013/0331663 A1 | 12/2013 | Albert et al. |
| 2013/0331665 A1 | 12/2013 | Bly et al. |
| 2013/0338448 A1 | 12/2013 | Libbus et al. |
| 2014/0012154 A1 | 1/2014 | Mazar |
| 2014/0058280 A1 | 2/2014 | Chefles et al. |
| 2014/0088394 A1 | 3/2014 | Sunderland |
| 2014/0094676 A1 | 4/2014 | Gani et al. |
| 2014/0094709 A1 | 4/2014 | Korzinov et al. |
| 2014/0100432 A1 | 4/2014 | Golda et al. |
| 2014/0171751 A1 | 6/2014 | Sankman et al. |
| 2014/0116825 A1 | 7/2014 | Kurzweil et al. |
| 2014/0206976 A1 | 7/2014 | Thompson et al. |
| 2014/0206977 A1 | 7/2014 | Bahney et al. |
| 2014/0243621 A1 | 8/2014 | Weng et al. |
| 2014/0275827 A1 | 9/2014 | Gill et al. |
| 2014/0275840 A1 | 9/2014 | Osorio |
| 2014/0275928 A1 | 9/2014 | Acquista et al. |
| 2014/0303647 A1 | 10/2014 | Sepulveda et al. |
| 2014/0330136 A1 | 11/2014 | Manicka et al. |
| 2015/0005854 A1 | 1/2015 | Said |
| 2015/0022372 A1 | 1/2015 | Vosch |
| 2015/0057512 A1 | 2/2015 | Kapoor |
| 2015/0073252 A1 | 3/2015 | Mazar |
| 2015/0081959 A1 | 3/2015 | Vlach et al. |
| 2015/0082623 A1 | 3/2015 | Felix et al. |
| 2015/0087921 A1 | 3/2015 | Felix et al. |
| 2015/0087922 A1 | 3/2015 | Bardy et al. |
| 2015/0087923 A1 | 3/2015 | Bardy et al. |
| 2015/0087933 A1 | 3/2015 | Gibson et al. |
| 2015/0087948 A1 | 3/2015 | Bishay et al. |

(56) References Cited

U.S. PATENT DOCUMENTS

| | | |
|---|---|---|
| 2015/0087949 A1 | 3/2015 | Felix et al. |
| 2015/0087950 A1 | 3/2015 | Felix et al. |
| 2015/0087951 A1 | 3/2015 | Felix et al. |
| 2015/0088007 A1 | 3/2015 | Bardy et al. |
| 2015/0088020 A1 | 3/2015 | Dreisbach et al. |
| 2015/0094556 A1 | 4/2015 | Geva et al. |
| 2015/0148637 A1 | 5/2015 | Golda et al. |
| 2015/0157273 A1 | 6/2015 | An et al. |
| 2015/0173671 A1 | 6/2015 | Paalasmaa et al. |
| 2015/0193595 A1 | 7/2015 | McNamara et al. |
| 2015/0223711 A1 | 8/2015 | Raeder et al. |
| 2015/0238107 A1 | 8/2015 | Acquista et al. |
| 2015/0289814 A1 | 10/2015 | Magar et al. |
| 2015/0297134 A1 | 10/2015 | Albert et al. |
| 2015/0327781 A1 | 11/2015 | Hernandez-Silverira et al. |
| 2015/0351689 A1 | 12/2015 | Adams |
| 2015/0351799 A1 | 12/2015 | Sepulveda et al. |
| 2015/0374244 A1 | 12/2015 | Yoo et al. |
| 2016/0022161 A1 | 1/2016 | Khair |
| 2016/0029906 A1 | 2/2016 | Tompkins et al. |
| 2016/0066808 A1 | 3/2016 | Hijazi |
| 2016/0085927 A1 | 3/2016 | Dettinger et al. |
| 2016/0085937 A1 | 3/2016 | Dettinger et al. |
| 2016/0086297 A1 | 3/2016 | Dettinger et al. |
| 2016/0098536 A1 | 4/2016 | Dettinger et al. |
| 2016/0098537 A1 | 4/2016 | Dettinger et al. |
| 2016/0113520 A1 | 4/2016 | Manera |
| 2016/0120433 A1 | 5/2016 | Hughes et al. |
| 2016/0120434 A1 | 5/2016 | Park et al. |
| 2016/0128597 A1 | 5/2016 | Lin et al. |
| 2016/0135746 A1 | 5/2016 | Kumar et al. |
| 2016/0149292 A1 | 5/2016 | Ganton |
| 2016/0157744 A1 | 6/2016 | Wu et al. |
| 2016/0166155 A1 | 6/2016 | Banet et al. |
| 2016/0192852 A1 | 7/2016 | Bozza et al. |
| 2016/0192855 A1 | 7/2016 | Geva et al. |
| 2016/0192856 A1 | 7/2016 | Lee |
| 2016/0198972 A1 | 7/2016 | Lee et al. |
| 2016/0232807 A1 | 8/2016 | Ghaffari et al. |
| 2016/0262619 A1 | 9/2016 | Marcus et al. |
| 2016/0278658 A1 | 9/2016 | Bardy et al. |
| 2016/0287177 A1 | 10/2016 | Huppert et al. |
| 2016/0287207 A1 | 10/2016 | Xue |
| 2016/0296132 A1 | 10/2016 | Bojovic et al. |
| 2016/0302725 A1 | 10/2016 | Schultz et al. |
| 2016/0302726 A1 | 10/2016 | Chang |
| 2016/0317048 A1 | 11/2016 | Chan et al. |
| 2016/0317057 A1 | 11/2016 | Li et al. |
| 2016/0359150 A1 | 12/2016 | de Francisco Martin et al. |
| 2016/0361015 A1 | 12/2016 | Wang et al. |
| 2016/0367164 A1 | 12/2016 | Felix et al. |
| 2016/0374583 A1 | 12/2016 | Cerruti et al. |
| 2017/0042447 A1 | 2/2017 | Rossi |
| 2017/0055896 A1 | 3/2017 | Al-Ali et al. |
| 2017/0056682 A1 | 3/2017 | Kumar |
| 2017/0065823 A1 | 3/2017 | Kaib et al. |
| 2017/0076641 A1 | 3/2017 | Senanayake |
| 2017/0188872 A1 | 7/2017 | Hughes et al. |
| 2017/0188971 A1 | 7/2017 | Hughes et al. |
| 2018/0049698 A1 | 2/2018 | Berg |
| 2018/0049716 A1 | 2/2018 | Rajagopal et al. |
| 2018/0064388 A1 | 3/2018 | Heneghan et al. |
| 2018/0110266 A1 | 4/2018 | Lee et al. |
| 2018/0125387 A1 | 5/2018 | Hadley et al. |
| 2018/0144241 A1 | 5/2018 | Liu et al. |
| 2018/0146875 A1 | 5/2018 | Friedman et al. |
| 2018/0161211 A1 | 6/2018 | Beckey |
| 2018/0242876 A1 | 8/2018 | Hughes et al. |
| 2018/0257346 A1 | 9/2018 | Austin |
| 2018/0260706 A1 | 9/2018 | Galloway et al. |
| 2018/0289274 A1 | 10/2018 | Bahney et al. |
| 2018/0374576 A1 | 12/2018 | Dettinger et al. |
| 2019/0021671 A1 | 1/2019 | Kumar et al. |
| 2019/0038148 A1 | 2/2019 | Valys |
| 2019/0046066 A1 | 2/2019 | Hughes et al. |
| 2019/0069788 A1 | 3/2019 | Coleman et al. |
| 2019/0090769 A1 | 3/2019 | Boleyn et al. |
| 2019/0097339 A1 | 3/2019 | Lim et al. |
| 2019/0098758 A1 | 3/2019 | Hassemer et al. |
| 2019/0099132 A1 | 4/2019 | Mulinti et al. |
| 2019/0167143 A1 | 6/2019 | Li et al. |
| 2019/0209022 A1 | 7/2019 | Sobol |
| 2019/0246928 A1 | 8/2019 | Bahney et al. |
| 2019/0274574 A1 | 9/2019 | Hughes et al. |
| 2019/0282178 A1 | 9/2019 | Volosin et al. |
| 2019/0290147 A1 | 9/2019 | Persen et al. |
| 2019/0298201 A1 | 10/2019 | Persen et al. |
| 2019/0298209 A1 | 10/2019 | Persen et al. |
| 2019/0298272 A1 | 10/2019 | Persen |
| 2019/0374163 A1 | 12/2019 | Faabaek et al. |
| 2019/0378617 A1 | 12/2019 | Charles et al. |
| 2020/0060563 A1 | 2/2020 | Boleyn |
| 2020/0093388 A1 | 3/2020 | Bouguerra et al. |
| 2020/0100693 A1 | 4/2020 | Velo |
| 2020/0108260 A1 | 4/2020 | Haddad et al. |
| 2020/0121209 A1 | 4/2020 | Kumar et al. |
| 2020/0170529 A1 | 6/2020 | Bahney et al. |
| 2020/0178825 A1 | 6/2020 | Lu |
| 2020/0178828 A1 | 6/2020 | Bahney et al. |
| 2020/0193597 A1 | 6/2020 | Fan |
| 2020/0196897 A1 | 6/2020 | Biswas et al. |
| 2020/0214563 A1 | 7/2020 | Lin |
| 2020/0214584 A1 | 7/2020 | McNamara et al. |
| 2020/0237309 A1 | 7/2020 | Golda et al. |
| 2020/0289014 A1 | 9/2020 | Park et al. |
| 2020/0337608 A1 | 10/2020 | Garai et al. |
| 2020/0352489 A1 | 11/2020 | Hoppe et al. |
| 2020/0367779 A1 | 11/2020 | Korzinov et al. |
| 2020/0397313 A1 | 12/2020 | Attia et al. |
| 2021/0038102 A1 | 2/2021 | Boleyn et al. |
| 2021/0059612 A1 | 3/2021 | Krebs et al. |
| 2021/0085215 A1 | 3/2021 | Auerbach et al. |
| 2021/0085255 A1 | 3/2021 | Vule et al. |
| 2021/0125722 A1 | 4/2021 | Sherkat et al. |
| 2021/0153761 A1 | 5/2021 | Jung et al. |
| 2021/0217519 A1 | 7/2021 | Park et al. |
| 2021/0244279 A1 | 8/2021 | Szabados et al. |
| 2021/0269046 A1 | 9/2021 | Hashimoto et al. |
| 2021/0298688 A1 | 9/2021 | Banerjee et al. |
| 2021/0304855 A1 | 9/2021 | Ansari et al. |
| 2021/0315470 A1 | 10/2021 | Wu et al. |
| 2021/0315504 A1 | 10/2021 | Kumar et al. |
| 2021/0361218 A1 | 11/2021 | Szabados et al. |
| 2021/0369178 A1 | 12/2021 | Szabados et al. |
| 2021/0374502 A1 | 12/2021 | Roth et al. |
| 2021/0378579 A1 | 12/2021 | Doron et al. |
| 2021/0393187 A1 | 12/2021 | Amos et al. |
| 2022/0022798 A1 | 1/2022 | Soon-Shiong et al. |
| 2022/0031223 A1 | 2/2022 | Li et al. |
| 2022/0039719 A1 | 2/2022 | Abercrombie, II et al. |
| 2022/0039720 A1 | 2/2022 | Abercrombie, II et al. |
| 2022/0039721 A1 | 2/2022 | Abercrombie, II et al. |
| 2022/0039722 A1 | 2/2022 | Abercrombie, II et al. |
| 2022/0079497 A1 | 3/2022 | Bardy et al. |
| 2022/0093247 A1 | 3/2022 | Park et al. |
| 2022/0095982 A1 | 3/2022 | de Saint Victor et al. |
| 2022/0142493 A1 | 5/2022 | Albert |
| 2022/0142495 A1 | 5/2022 | De Marco et al. |
| 2022/0160279 A1 | 5/2022 | Abercrombie, II et al. |
| 2022/0160285 A1 | 5/2022 | Szabados et al. |
| 2022/0167905 A1 | 6/2022 | Szabados et al. |
| 2022/0280093 A1 | 9/2022 | Abercrombie, II et al. |
| 2022/0296144 A1 | 9/2022 | Abercrombie, II et al. |
| 2022/0330874 A1 | 10/2022 | Szabados et al. |
| 2022/0330875 A1 | 10/2022 | Szabados et al. |
| 2022/0361793 A1 | 11/2022 | Abercrombie, II et al. |
| 2023/0056777 A1 | 2/2023 | Abercrombie, II et al. |
| 2023/0172511 A1 | 6/2023 | Abercrombie, II et al. |
| 2023/0172518 A1 | 6/2023 | Szabados et al. |
| 2023/0200702 A1 | 6/2023 | Sepulveda et al. |
| 2023/0207122 A1 | 6/2023 | Park et al. |
| 2023/0248288 A1 | 8/2023 | Bahney et al. |

(56) References Cited

U.S. PATENT DOCUMENTS

| | | | |
|---|---|---|---|
| 2023/0371874 A1 | 11/2023 | Abercrombie, II et al. | |
| 2024/0145080 A1 | 5/2024 | Park et al. | |

FOREIGN PATENT DOCUMENTS

| | | |
|---|---|---|
| AU | 2021218704 | 2/2024 |
| CA | 2 752 154 | 8/2010 |
| CA | 2 898 626 | 7/2014 |
| CA | 2 797 980 | 8/2015 |
| CA | 2 651 203 | 9/2017 |
| CA | 2 966 182 | 6/2020 |
| CA | 3 171 482 | 3/2024 |
| CN | 102038497 | 7/2012 |
| CN | 102883775 | 12/2014 |
| CN | 103997955 | 11/2016 |
| CN | 303936805 | 11/2016 |
| CN | 107205679 | 9/2017 |
| CN | 108113647 | 6/2018 |
| CN | 109363659 | 2/2019 |
| CN | 110491500 | 11/2019 |
| CN | 110766691 | 2/2020 |
| CN | 110890155 | 3/2020 |
| CN | 110974217 | 4/2020 |
| CN | 115426940 | 12/2022 |
| CN | 116322498 | 6/2023 |
| CN | 116530951 | 8/2023 |
| EM | 001857966-0001 | 5/2011 |
| EM | 003611714-0001 | 1/2017 |
| EM | 003611714-0002 | 1/2017 |
| EM | 003611714-0003 | 1/2017 |
| EM | 003611714-0004 | 1/2017 |
| EM | 003611714-0005 | 1/2017 |
| EP | 0509689 | 4/1992 |
| EP | 1738686 | 6/2006 |
| EP | 1782729 | 5/2007 |
| EP | 1981402 | 10/2008 |
| EP | 2262419 | 12/2010 |
| EP | 2395911 | 12/2011 |
| EP | 2568878 | 3/2013 |
| EP | 2635179 | 9/2013 |
| EP | 2635180 | 9/2013 |
| EP | 2948050 | 12/2015 |
| EP | 2983593 | 2/2016 |
| EP | 3165161 | 5/2017 |
| EP | 3212061 | 9/2017 |
| EP | 3753483 | 12/2020 |
| EP | 3387991 | 6/2022 |
| EP | 4103051 | 12/2022 |
| GB | 2 299 038 | 9/1996 |
| GB | 2 348 707 | 10/2000 |
| IN | 002592907-0001 | 12/2014 |
| JP | S61-137539 | 6/1986 |
| JP | H05-329123 | 12/1993 |
| JP | H08-317913 | 3/1996 |
| JP | H08-322952 | 12/1996 |
| JP | 2000-126145 | 5/2000 |
| JP | 2001-057967 | 3/2001 |
| JP | 2003-275186 | 9/2003 |
| JP | 2004-121360 | 4/2004 |
| JP | 2006-110180 | 4/2006 |
| JP | 2006-136405 | 6/2006 |
| JP | 2006-520657 | 9/2006 |
| JP | 2007-045967 | 2/2007 |
| JP | 2007-503910 | 3/2007 |
| JP | 2007-504917 | 3/2007 |
| JP | 2007-097822 | 4/2007 |
| JP | 2007-296266 | 11/2007 |
| JP | 2008-532596 | 8/2008 |
| JP | 2008-200120 | 9/2008 |
| JP | 2009-518099 | 5/2009 |
| JP | 2009-525816 | 7/2009 |
| JP | 2011-516110 | 5/2011 |
| JP | 2011-519583 | 7/2011 |
| JP | 2013-521966 | 6/2013 |
| JP | 5203973 | 6/2013 |
| JP | 1483906 S | 10/2013 |
| JP | 2014-008166 | 1/2014 |
| JP | 5559425 | 7/2014 |
| JP | 2014-150826 | 8/2014 |
| JP | 2014-236982 | 12/2014 |
| JP | 2015-530225 | 10/2015 |
| JP | 2015-531954 | 11/2015 |
| JP | 2016-504159 | 2/2016 |
| JP | 2013-517053 | 5/2016 |
| JP | 2016-523139 | 8/2016 |
| JP | 2017-136380 | 8/2017 |
| JP | 6198849 | 9/2017 |
| JP | 2017-209482 | 11/2017 |
| JP | 2018-504148 | 2/2018 |
| JP | 2018-508325 | 3/2018 |
| JP | 2018-513702 | 5/2018 |
| JP | 6336640 | 5/2018 |
| JP | D1596476 | 8/2018 |
| JP | 2018-153651 | 10/2018 |
| JP | 2018-174995 | 11/2018 |
| JP | 2019-503761 | 2/2019 |
| JP | 6491826 | 3/2019 |
| JP | 6495228 | 3/2019 |
| JP | 2020-058819 | 4/2020 |
| JP | 2020-509840 | 4/2020 |
| JP | 6766199 | 9/2020 |
| JP | 2021-003591 | 1/2021 |
| JP | 6901543 | 6/2021 |
| JP | 2021-525616 | 9/2021 |
| JP | 2021-166726 | 10/2021 |
| JP | 2022-501123 | 1/2022 |
| JP | 2022-037153 | 3/2022 |
| JP | 2022-038858 | 3/2022 |
| JP | 2023-508235 | 3/2023 |
| JP | 2023-074267 | 5/2023 |
| JP | 2023-100210 | 7/2023 |
| JP | 2023-536981 | 8/2023 |
| JP | 2023-536982 | 8/2023 |
| JP | 7406001 | 12/2023 |
| JP | 2024-009608 | 1/2024 |
| JP | 2024-502335 | 1/2024 |
| JP | 2024-021061 | 2/2024 |
| JP | 2024-026058 | 2/2024 |
| JP | 7431777 | 2/2024 |
| JP | 2024-050777 | 4/2024 |
| JP | 2024-521799 | 6/2024 |
| JP | 2024-087811 | 7/2024 |
| JP | 2024-104034 | 8/2024 |
| KR | 3003784570000 | 3/2005 |
| KR | 1020050055072 | 6/2005 |
| KR | 1020140050374 | 4/2014 |
| KR | 10-1513288 | 4/2015 |
| KR | 3008476060000 | 3/2016 |
| KR | 3008476090000 | 3/2016 |
| KR | 3008482960000 | 3/2016 |
| KR | 3008584120000 | 6/2016 |
| KR | 3008953750000 | 2/2017 |
| KR | 3008953760000 | 2/2017 |
| KR | 3008987790000 | 3/2017 |
| KR | 1020170133527 | 12/2017 |
| KR | 3009445870000 | 2/2018 |
| KR | 3009547690000 | 4/2018 |
| KR | 3009547710000 | 4/2018 |
| KR | 10-2563372 | 7/2023 |
| KR | 10-2023-0119036 | 8/2023 |
| WO | WO 99/023943 | 5/1999 |
| WO | WO 01/016607 | 3/2001 |
| WO | WO 2003/043494 | 5/2003 |
| WO | WO 2004/100785 | 11/2004 |
| WO | WO 2005/025668 | 3/2005 |
| WO | WO 2005/037946 | 4/2005 |
| WO | WO 2005/084533 | 9/2005 |
| WO | WO 2006/094513 | 9/2006 |
| WO | WO 2007/049080 | 3/2007 |
| WO | WO 2007/036748 | 4/2007 |
| WO | WO 2007/063436 | 6/2007 |
| WO | WO 2007/066270 | 6/2007 |
| WO | WO 2007/071180 | 6/2007 |
| WO | WO 2007/072069 | 6/2007 |

(56) References Cited

FOREIGN PATENT DOCUMENTS

| | | |
|---|---|---|
| WO | WO 2007/092543 | 8/2007 |
| WO | WO 2008/005015 | 1/2008 |
| WO | WO 2008/005016 | 1/2008 |
| WO | WO 2008/057884 | 5/2008 |
| WO | WO 2008/120154 | 10/2008 |
| WO | WO 2009/055397 | 4/2009 |
| WO | WO 2009/074928 | 6/2009 |
| WO | WO 2009/112972 | 9/2009 |
| WO | WO 2009/112976 | 9/2009 |
| WO | WO 2009/112979 | 9/2009 |
| WO | WO 2009/134826 | 11/2009 |
| WO | WO 2010/014490 | 2/2010 |
| WO | WO 2010/104952 | 9/2010 |
| WO | WO 2010/105203 | 9/2010 |
| WO | WO 2010/107913 | 9/2010 |
| WO | WO 2010/093900 | 10/2010 |
| WO | WO 2011/077097 | 6/2011 |
| WO | WO 2011/084636 | 7/2011 |
| WO | WO 2011/112420 | 9/2011 |
| WO | WO 2011/143490 | 11/2011 |
| WO | WO 2011/149755 | 12/2011 |
| WO | WO 2012/003840 | 1/2012 |
| WO | WO 2012/009453 | 1/2012 |
| WO | WO 2012/061509 | 5/2012 |
| WO | WO 2012/061518 | 5/2012 |
| WO | WO 2012/125425 | 9/2012 |
| WO | WO 2012/140559 | 10/2012 |
| WO | WO 2012/160550 | 11/2012 |
| WO | WO 2013/065147 | 5/2013 |
| WO | WO 2013/179368 | 12/2013 |
| WO | WO 2014/047032 | 3/2014 |
| WO | WO 2014/047205 | 3/2014 |
| WO | WO 2014/051563 | 4/2014 |
| WO | WO 2014/055994 | 4/2014 |
| WO | WO 2014/116825 | 7/2014 |
| WO | WO 2014/168841 | 10/2014 |
| WO | WO 2014/197822 | 12/2014 |
| WO | WO 2015/089484 | 6/2015 |
| WO | WO 2016/044514 | 3/2016 |
| WO | WO 2016/044515 | 3/2016 |
| WO | WO 2016/044519 | 3/2016 |
| WO | WO 2016/057728 | 4/2016 |
| WO | WO 2016/070128 | 5/2016 |
| WO | WO 2016/130545 | 8/2016 |
| WO | WO 2016/172201 | 10/2016 |
| WO | WO 2016/181321 | 11/2016 |
| WO | WO 2017/039518 | 3/2017 |
| WO | WO 2017/041014 | 3/2017 |
| WO | WO 2017/043597 | 3/2017 |
| WO | WO 2017/043603 | 3/2017 |
| WO | WO 2017/108215 | 6/2017 |
| WO | WO 2017/159635 | 9/2017 |
| WO | WO 2018/164840 | 9/2018 |
| WO | WO 2018/218310 | 12/2018 |
| WO | WO 2019/071201 | 4/2019 |
| WO | WO 2019/188311 | 10/2019 |
| WO | WO 2019/191487 | 10/2019 |
| WO | WO 2019/233807 | 12/2019 |
| WO | WO 2020/008864 | 1/2020 |
| WO | WO 2020/013895 | 1/2020 |
| WO | WO 2020/041363 | 2/2020 |
| WO | WO 2020/058314 | 3/2020 |
| WO | WO 2020/224041 | 11/2020 |
| WO | WO 2020/0226852 | 11/2020 |
| WO | WO 2020/262403 | 12/2020 |
| WO | WO 2021/150122 | 7/2021 |
| WO | WO 2021/163331 | 8/2021 |
| WO | WO 2021/200245 | 10/2021 |
| WO | WO 2021/200764 | 10/2021 |
| WO | WO 2021/205788 | 10/2021 |
| WO | WO 2021/210592 | 10/2021 |
| WO | WO 2021/241308 | 12/2021 |
| WO | WO 2021245203 | 12/2021 |
| WO | WO 2022/093709 | 5/2022 |
| WO | WO 2022/147520 | 7/2022 |
| WO | WO 2022/251636 | 12/2022 |
| WO | WO 2023/114742 | 6/2023 |
| WO | WO 2024/102663 A2 | 5/2024 |

OTHER PUBLICATIONS

3M Corporation, "3M Surgical Tapes—Choose the Correct Tape" quicksheet (2004).
Altini, et al., An ECG Patch Combining a Customized Ultra-Low-Power ECG SOC Withbluetooth Low Energy for Long Term Ambulatory Monitoring, Conference: Proceddings of Wireless Health 2011, WH 2011, Oct. 10-13, 2011.
British-Made Early Warning Monitor a "Game Changer", healthcare-in-europe.com, Mar. 31, 2014.
Comstock, Proteus Digital Health Quietly Launches Consumer-Facing Wearable for Athletes, Mobile Health News, Oct. 29, 2014.
Coxworth, Small Adhesive Partch Outperforms Traditional Tech for Detecting Arrhythmia, Scripps, iRhythm Technologies, Jan. 3, 2014.
Del Mar et al.; The history of clinical holter monitoring; A.N.E.; vol. 10; No. 2; pp. 226-230; Apr. 2005.
Enseleit et al.; Long-term continuous external electrocardiogramg: a review; Eurospace; vol. 8; pp. 255-266; 2006.
Feng-Tso Sun et al., "PEAR: Power efficiency through activity recognition (for ECG-based sensing)",Pervasive Computing Technologies for Healthcare (Pervasivehealth) 2011 5th International Conference on, IEEE, May 23, 2011. pp. 115-122.
Hoefman et al.; Optimal duration of event recording for diagnosis of arrhythmias in patients with palpitations and light-headedness in the general practice; Family Practice; Dec. 7, 2006.
Huyett "Keystock & Shim Stock Catalog" p. 9 Feb. 2014. found at https://issuu.com/glhuyett/docs/gl-huyett-keystock-catalog/20 (Year: 2014).
Ikeda Y. et al., "A Method for Transmission Data Reduction for Automated Monitoring System via CNN Distribution Process", Proceedings of the Symposium of Multi-media, Distribution, Coordination, and Mobile (DOCOMO2019), Jul. 2019.
International Search Report and Written Opinion for International Application No. PCT/US2021/044976 mailed Jan. 24, 2022 in 24 pages.
Kennedy et al.; The history, science, and innovation of holter technology; A.N.E.; vol. 11; No. 1; pp. 85-94; 2006.
"Mayo Alumni", Mayo Clinic, Rochester, MN, Spring 2011, in 24 pages.
Medtronic Launches Seeq Wearable Cardiac Monitoring System in United States, Diagnostic and Interventional Cardiology, Oct. 7, 2014.
Mundt et al. "A Multiparameter Wearable Physiologic Monitoring System for Space and Terrestrial Applications" IEEE Transactions on Information Technology in Biomedicine, vol. 9, No. 3, pp. 382-384, Sep. 2005.
Prakash, New Patch-Based Wearable Sensor Combines Advanced Skin Adhesives and Sensor Technologies, Advantage Business Marketing, Jul. 17, 2012.
Redjem Bouhenguel et al, "A risk and Incidence Based Atrial Fibrillation Detection Scheme for Wearable Healthcare Computing Devices," Pervasive Computer Technologies for Healthcare, 2012 6th International Conference On, IEEE, pp. 97-104, May 21, 2012.
Reiffel et al.; Comparison of autotriggered memory loop recorders versus standard loop recorders versus 24-hour holter monitors for arrhythmia detection; Am. J. Cardiology; vol. 95; pp. 1055-1059; May 1, 2005.
Request for Reexamination of U.S. Pat. No. 7,020,508 under 35 U.S.C. §§ 311-318 and 37 C.F.R. § 1.913 as submitted Sep. 14, 2012 in 78 pages.
Scapa Medical product listing and descriptions (2008) available at http://www.caapana.com/productlist.jsp and http://www.metplus.co.rs/pdf/prospekti/Samolepljivemedicinsketrake.pdf; retrieved via WayBack Machine Sep. 24, 2012.
Strong, Wearable Technologies Conference 2013 Europe—Notes and Roundup, Wearable Technologies Conference, Feb. 8, 2013.
Sumner, Stanford Engineers Monitor Heart Health Using Paper-Thin Flexible 'Skin', Stanford Report, May 14, 2013.

(56) References Cited

OTHER PUBLICATIONS

Ward et al.; Assessment of the diagnostic value of 24-hour ambulatory electrocardiograma monitoring; Biotelemetry Patient monitoring; vol. 7; 1980.
Ziegler et al.; Comparison of continuous versus intermittent monitoring of atrial arrhythmias; Heart Rhythm; vol. 3; No. 12; pp. 1445-1452; Dec. 2006.
Zimetbaum et al.; The evolving role of ambulatory arrhythmia monitoring in general clinic practice; Ann. Intern. Med.; vol. 130; pp. 846-8556; 1999.
Zimetbaum et al.; Utility of patient-activated cardiac event recorders in general clinical practice; The Amer. J. of Cardiology; vol. 79; Feb. 1, 1997.
Akram, Muhammad Usman, "Application of Prototype Based Fuzzy Classifiers for ECG based Cardiac Arrhythmia Recognition", Jan. 1, 2008 retrieved from faculty.pieas.edu.pk/Fayyaz/_static/pubfiles/student/usman_thesis.pdf [retrieved on Feb. 17, 2015] in 93 pages.
Behind the Design: How iRhythm Built Its New Zio Monitor. Online, published date Oct. 4, 2023. Retrieved on Jun. 18, 2024 from URL: https://www.mddionline.com/cardiovascular/behind-the-design-how-irhythm-built-its-new-zio-monitor.
Rajpurkar et al, "Cardiologist-Level Arrhythmia Detection with Convolutinal Neural Networks," ARXIV.org, https://arxiv.org/abs/1707.01836, Jul. 6, 2017 in 9 pages.

\* cited by examiner

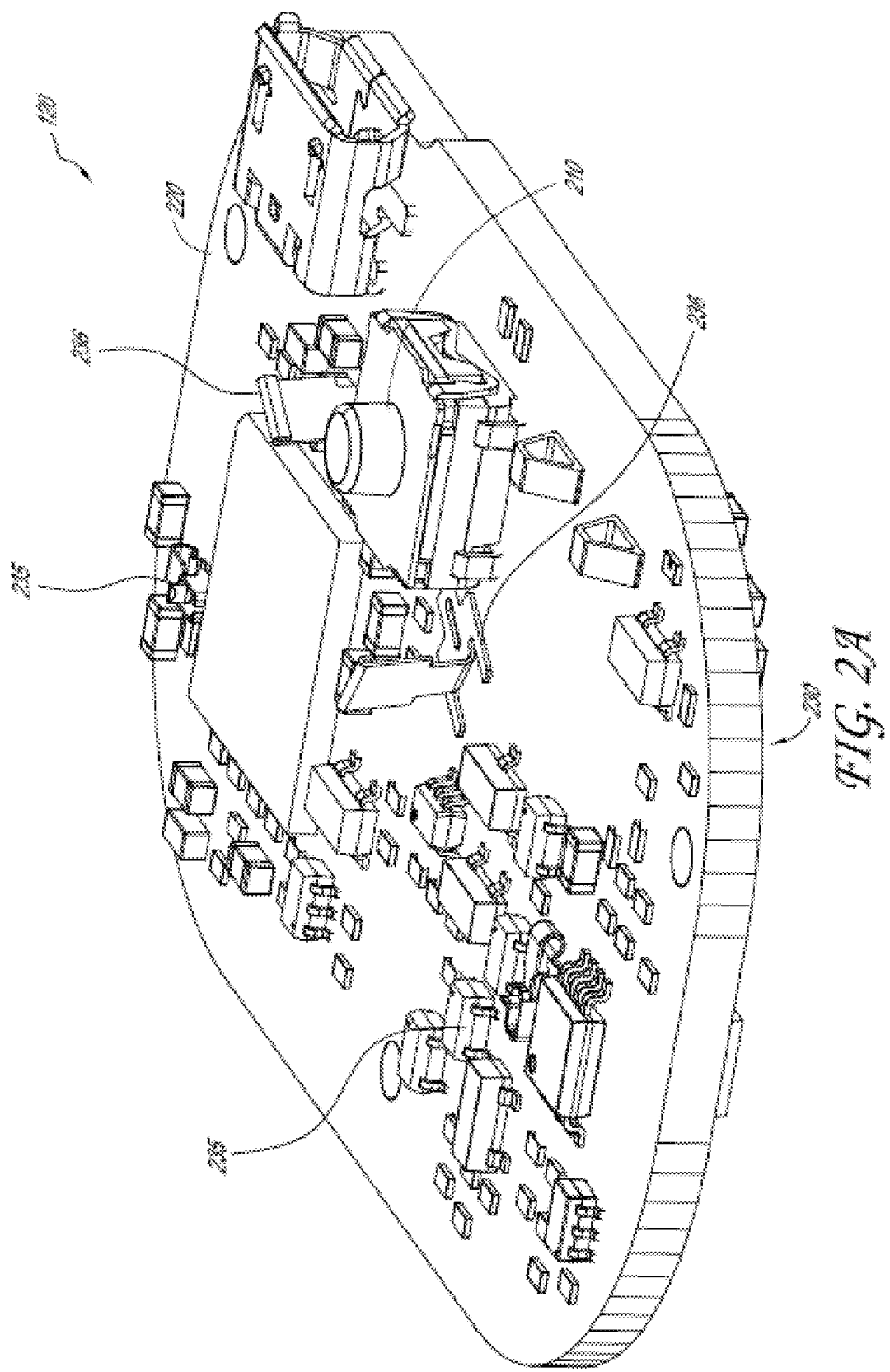

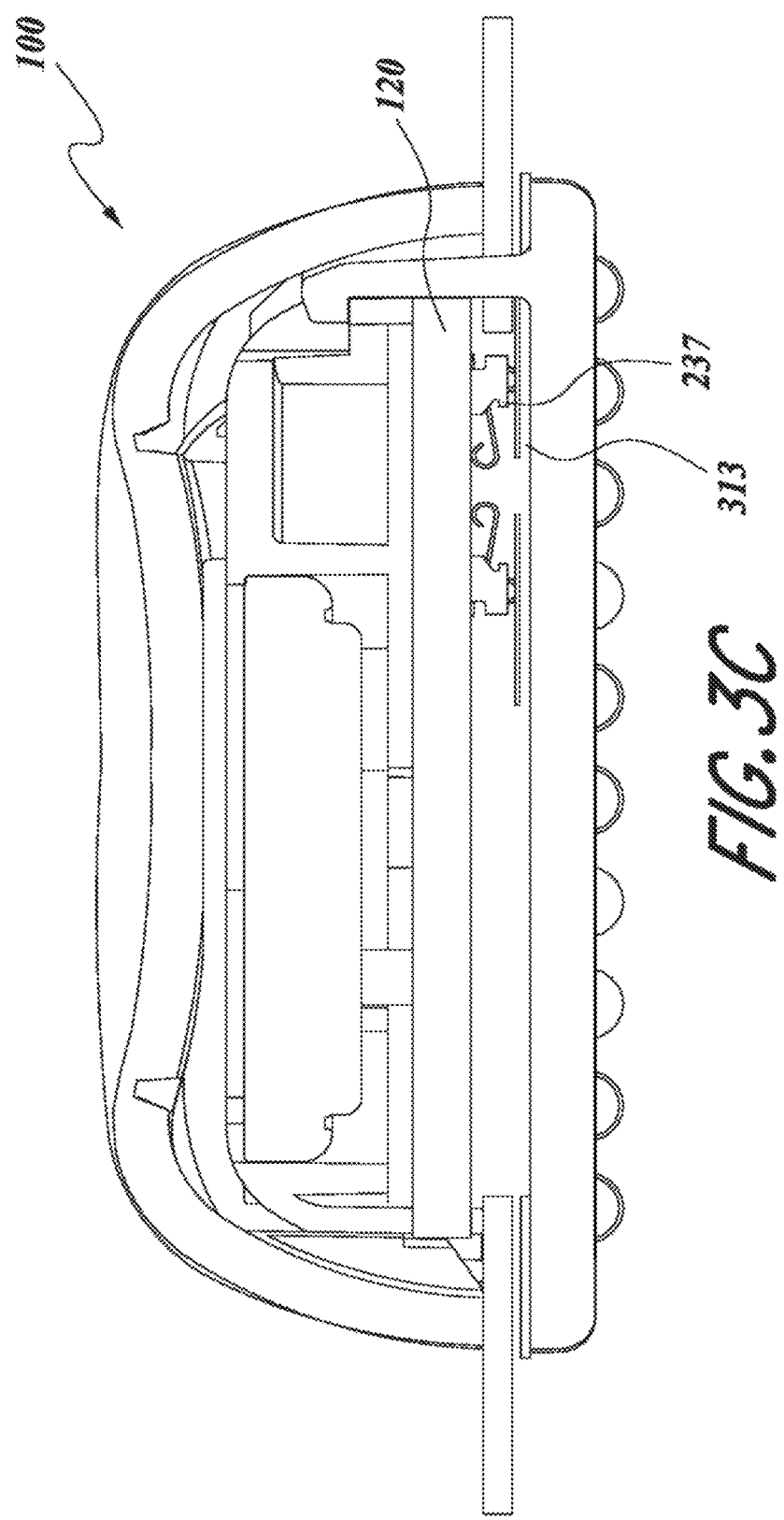

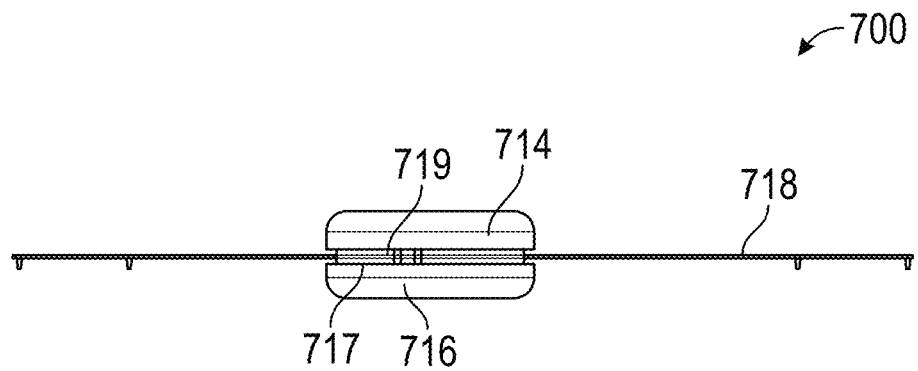
FIG. 6D1
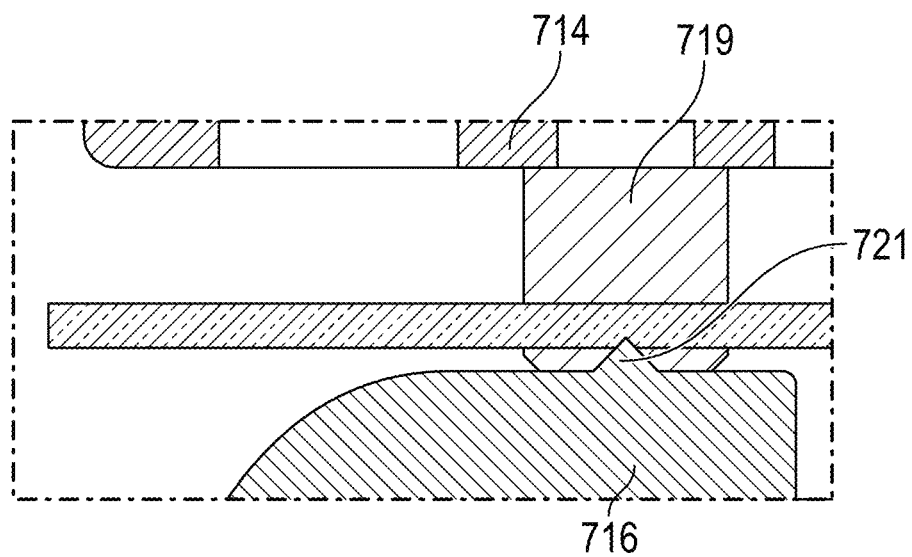
FIG. 6D2

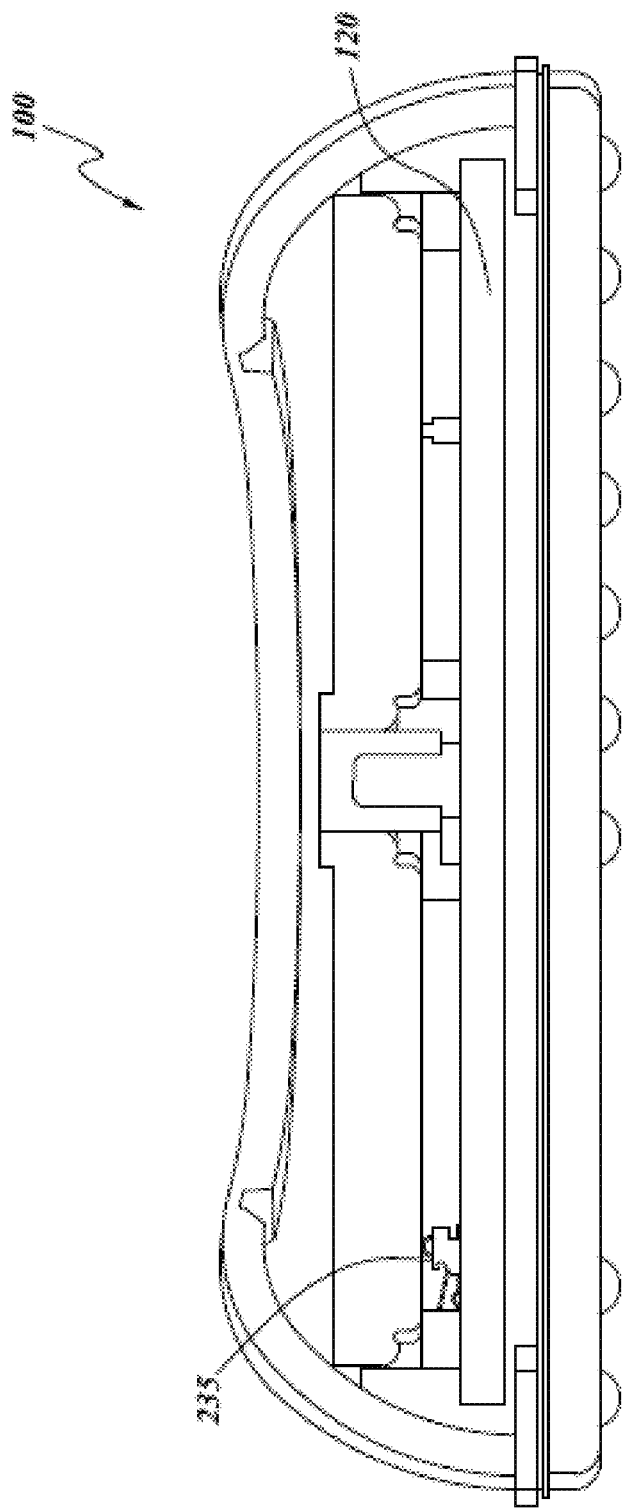

WEARABLE DEVICE

CROSS-REFERENCE TO RELATED APPLICATIONS

This application is a continuation of U.S. patent application Ser. No. 18/175,315, filed on Feb. 27, 2023, which is a continuation of U.S. patent application Ser. No. 17/805,622, filed on Jun. 6, 2022, which is a continuation of U.S. patent application Ser. No. 17/396,130, filed on Aug. 6, 2021, which claims priority from provisional U.S. Pat. App. No. 63/062,293, filed on Aug. 6, 2020, which is hereby incorporated by reference in its entirety.

BACKGROUND

For purposes of this disclosure, certain aspects, advantages, and novel features of various embodiments are described herein. It is to be understood that not necessarily all such advantages may be achieved in accordance with any particular embodiment. Thus, various embodiments may be or carried out in a manner that achieves one advantage or group of advantages as taught herein without necessarily achieving other advantages as may be taught or suggested herein.

FIELD OF THE INVENTION

Disclosed herein are materials, devices, methods, and systems for monitoring physiological signals. For example, such physiological signals may include heart signals, such as an electrocardiogram signal.

DESCRIPTION OF THE RELATED ART

Abnormal heart rhythms, or arrhythmias, may cause various types of symptoms, such as loss of-consciousness, palpitations, dizziness, or even death. An arrhythmia that causes such symptoms is often an indicator of significant underlying heart disease. It is important to identify when such symptoms are due to an abnormal heart rhythm, since treatment with various procedures, such as pacemaker implantation or percutaneous catheter ablation, can successfully ameliorate these problems and prevent significant symptoms and death. For example, monitors such as Holter monitors and similar devices are currently in use to monitor heart rhythms.

BRIEF SUMMARY OF EMBODIMENTS

Embodiments described herein are directed to a physiological monitoring device that may be worn continuously and comfortably by a human or animal subject for at least one week or more and more typically two to three weeks or more. In one embodiment, the device is specifically designed to sense and record cardiac rhythm (for example, electrocardiogram, ECG) data, although in various alternative embodiments one or more additional physiological parameters may be sensed and recorded. Such physiological monitoring devices may include a number of features to facilitate and/or enhance the patient experience and to make diagnosis of cardiac arrhythmias more accurate and timely.

In some embodiments, an electronic device for monitoring physiological signals in a mammal comprises: at least two flexible wings extending laterally from a housing, wherein the flexible wings comprise a first set of materials which enable the wings to conform to a surface of the mammal and the housing comprises a second set of materials; a printed circuit board assembly housed within the housing, wherein the housing is configured to prevent deformation of the printed circuit board in response to movement of the mammal; at least two electrodes embedded within the flexible wings, the electrodes configured to provide conformal contact with the surface of the mammal and to detect the physiological signals of the mammal; at least two electrode traces embedded within the wings and mechanically decoupled from the housing, the electrode traces configured to provide conformal contact with the surface of the mammal and transmit electrical signals from the electrodes to the printed circuit board assembly; and, at least one hinge portion connecting the wings to the housing, the hinge portions configured to flex freely at the area where it is joined to the housing.

In certain embodiments, each wing may comprise an adhesive. In embodiments, the electrodes can be in the same plane as the adhesive. In certain embodiments, each wing comprises at least one rim, wherein the rim is thinner than an adjacent portion of each wing. The housing may further comprise dimples or grooves configured to allow for airflow between the housing and the surface of the mammal. In certain embodiments, the rim is configured to prevent the release of a portion of the wing from the surface of the mammal. In some embodiments, an electronic device for monitoring physiological systems may comprise a measuring instrument configured to detect motion signals in at least one axis. This measuring instrument may be an accelerometer that can be configured to detect motion signals in three axes.

In embodiments, the motion signals can be collected in time with the physiological signals. In certain embodiments, a motion artifact is identified when the physiological signals and the motion signals match. Further embodiments may call for an event trigger coupled to the printed circuit board assembly. In some embodiments, the event trigger input is supported by the housing so as to prevent mechanical stress on the printed circuit board when the trigger is activated which, in turn, can reduce a source of artifact in the recorded signal. The event trigger may be concave or convex and larger than a human finger such that the event trigger is easily located. In certain embodiments, the electrode traces are configured to minimize signal distortion during movement of the mammal. In particular embodiments, gaskets may be used as a means for sealable attachment to the housing.

In certain embodiments, a method for monitoring physiological signals in a mammal may comprise: attaching an electronic device to the mammal, wherein the device comprises: at least two electrodes configured to detect physiological signals from the mammal, at least one measuring instrument configured to detect secondary signals, and at least two electrode traces connected to the electrodes and a housing; and, comparing the physiological signals to the secondary signals to identify an artifact.

In certain embodiments, identification of artifacts comprises a comparison between the frequency spectrum of the physiological signals and the frequency spectrum of the secondary signals. In embodiments, the secondary signals comprise motion signals that may be used to derive the activity and position of the mammal. In certain embodiments, the secondary signals are collected in three axes. In some embodiments, a tertiary signal may also be collected. In certain embodiments, the secondary signals comprise information about the connection between the electronic device and the mammal. In some embodiments, the secondary signals may be used to detect when the mammal is sleeping.

In some embodiments, a method of removing and replacing portions of a modular physiological monitoring device may comprise: applying the device described above to a mammal for a period of time greater than 7 days and collecting physiological data; using the device to detect a first set of physiological signals; removing the device from the surface of the mammal; removing a first component from the device; and, incorporating the first component into a second physiological monitoring device, the second physiological monitoring device configured to detect a second set of physiological signals.

In some embodiments, the first component is electrically connected to other device components without the use of a permanent connection. In some embodiments, the device may further comprise spring connections. In certain embodiments, the first component may be preserved for a second use by a housing to prevent damage. In particular embodiments, the first component is secured within a device by a mechanism that is capable of re-securing a second component once the first component is removed.

Certain embodiments may concern a system for inferring cardiac rhythm information from time-series data of heart beat intervals, as obtained from either consumer wearable or medical device products. A further aspect concerns improvements to the system to enable cardiac rhythm information to be inferred in a more robust and/or timely manner through the use of additional sources of data. This additional data may include summary statistics or specific signal features derived from an ECG, user activity time series data derived from an accelerometer, information related to user state, or information related to the day/time of the recording.

In certain embodiments, a system for selective transmission of electrocardiographic signal data from a wearable medical sensor, where QRS refers to the three fiducial points of an ECG recording at the time of ventricle depolarization, may comprise:
  a. A wearable medical sensor incorporating a QRS detector that produces a real-time estimate of each R peak location in the ECG
  b. Transmission of an R-R interval time series together with an onset time stamp from the sensor to a smartphone or internet-connected gateway device, according to a pre-defined schedule
  c. Transmission of the R-R interval time series and the onset time stamp from the smartphone or internet-connected gateway device to a server
  d. Server-side algorithmic inference of the most probable rhythms and their onset/offset times from the R-R interval time series data
  e. Filtering the list of inferred heart rhythms according to specific filter criteria, such that only inferred rhythms matching the given criteria are retained after filtering
  f. Transmission of the onset/offset time for each rhythm remaining after filtering, from the server to the smartphone or internet-connected gateway device
  g. Transmission of the onset/offset time for each rhythm remaining after filtering, from the smartphone or internet-connected gateway device to the wearable sensor
  h. Transmission of the section of recorded ECG corresponding to each onset-offset time pair from the sensor to the smartphone or internet-connected gateway device
  i. Transmission of the section of recorded ECG corresponding to each onset-offset time pair from the smartphone or internet-connected gateway device to the server The rhythm filter criteria may be specified by a physician or other medical professional prior to the use of the wearable sensor by a patient. In other embodiments, the rhythm filter criteria are dynamic and can be updated during the use of the system according to predefined rules. In some embodiments, these predefined rules may describe an adjustment to the filter criteria based on previous findings during use of the system. In some embodiments, the onset and offset time for each inferred rhythm may be adjusted such that the resulting duration for each rhythm is less than a given maximum permissible duration. Computed confidence measures may be an input to the rhythm filter criteria. In some embodiments, the system comprises inferring cardiac rhythm information from R-R interval time series data. In certain embodiments, the cardiac rhythm inference system is implemented as a cloud service accessible via an API.

In certain embodiments, the cardiac rhythm inference system is provided through a software library that can be incorporated into a standalone application. The R-R interval values may be are estimated from a photoplethysmography signal.

In certain embodiments of a method for inferring cardiac rhythm information, the cardiac rhythm inference system computes a confidence score for each type of cardiac rhythm, the method comprising:
  a. Computing the frequency and duration of each cardiac rhythm type inferred from the collection of R-R interval time series data for the given user
  b. Estimating a confidence statistic for each rhythm type based on the inferred frequency and duration of the rhythm across the collection of R-R interval time series for the given user
  c. Evaluating if the confidence statistic for each inferred rhythm exceeds a pre-determined threshold value
  d. Providing rhythm information back to the calling software only for those inferred rhythms for which the confidence statistic exceeds the threshold value In certain embodiments, the cardiac rhythm inference system accepts additional sources of data, comprising one or more of:
  e. User activity time series data measured by an accelerometer
  f. Information on the specific day and time of each R-R interval time series recording
  g. Information on user age, gender, clinical indication for monitoring, pre-existing medical conditions, medication information, and medical history
  h. ECG signal features and summary statistics, such as the mean, median, standard deviation or sum of the ECG signal sample values within a given time period
  i. A confidence rating provided by the measurement device to indicate the quality of heart beat estimation, for example, for each beat or for sequential time periods.
  j. Intra-beat interval measurements In embodiments, a system for monitoring cardiac signal data, comprises:
  wearable medical sensor, the wearable medical sensor configured to detect cardiac signals from a mammal and estimate the R-peak location within the cardiac signal;
  wherein the wearable medical sensor is configured to transmit an R-R interval time series and a time stamp to an intermediary device, the intermediary device configured to further transmit the R-R interval time series and time stamp to a server;
  wherein the server is configured to infer the most probable rhythms and their onset/offset times from the R-R interval time series and time stamp, the server configured to filter the most probable rhythms according to a first criteria into a filtered data set;

wherein the server is configured to transmit the filtered data set back to the wearable sensor via the intermediary device; and wherein the sensor transmits the full resolution cardiac signal to the server for a time period surrounding each of the filtered events.

In certain embodiments, a system for monitoring cardiac signal data comprises:

a server configured to communicate with a wearable sensor, the wearable sensor configured to detect cardiac signals from a mammal and estimate the R peak location within the cardiac signal;

wherein the wearable sensor is configured to transmit an R-R interval time series and a time stamp to the server;

wherein the server is configured to infer the most probable rhythms and their onset/offset times from the R-R interval time series and time stamp, the server configured to filter the most probable rhythms according to a first criteria into a filtered data set; and wherein the server is configured to transmit a summary of the filtered data.

In particular embodiments, a server for monitoring cardiac signal data, comprises:

a portal configured to communicate with a wearable sensor, the wearable sensor configured to detect cardiac signals from a mammal and estimate the R peak location within the cardiac signal, wherein the wearable sensor is configured to transmit an R-R interval time series and a time stamp to an intermediary device, the intermediary device configured to further transmit the R-R interval time series and time stamp to a server;

a processor configured to infer the most probable rhythms and their onset/offset times from the R-R interval time series and time stamp, the processor configured to filter the most probable rhythms according to a first criteria into a filtered data set; and wherein the server is configured to transmit a summary of the filtered data set.

In embodiments, a non-transitory storage medium having computer-executable instructions stored thereon, the computer-executable instructions readable by a computing system comprising one or more computing devices, wherein the computer-executable instructions are executable on the computing system in order to cause the computing system to perform operations comprises: receiving, by a computing system through a communication link, physiological sensor data generated by a patient monitoring device, the physiological sensor data associated with a first patient; analyzing, by the computing system, the physiological sensor data to determine whether one or more points in the physiological data that are likely indicative of one or more predetermined set of conditions; and after determining that at least one of the one or more points in the physiological data is likely indicative of at least one of the one or more predetermined set of conditions, generating, by the computing system, an electronic data package for transmission to the patient monitoring device, the electronic data package including location data regarding the at least one of the one or more points in the physiological sensor data that are likely indicative of the at least one of the one or more predetermined set of conditions.

In certain embodiments, the physiological sensor data may comprise a sampling of interval data measured from the recorded signal data, the sampling of interval data of a data size less than the recorded signal data.

In particular embodiments, a system for monitoring physiological signals in a mammal may comprise: a wearable adhesive monitor configured to detect and record cardiac rhythm data from a mammal, the wearable adhesive monitor configured to extract a feature from the cardiac rhythm data; and wherein the wearable adhesive monitor is configured to transmit the feature to a processing device, the processing device configured to analyze the feature, identify locations of interest, and transmit the locations of interest back to the wearable adhesive monitor.

In certain embodiments, a system for assessing physiological sensor data from a patient monitoring device comprises: a computer processor and non-transitory computer-readable media combined with the computer processor configured to provide a program that includes a set of instructions stored on a first server, the set of instructions being executable by the computer processor, and further configured to execute a sensor data inference module of the program; the sensor data inference module of the program storing instructions to: receive physiological sensor data generated by a patient monitoring device, the physiological sensor data associated with a first patient; analyze the physiological sensor data to determine whether one or more points in the physiological data that are likely indicative of one or more predetermined set of conditions; and after determining that at least one of the one or more points in the physiological data is likely indicative of at least one of the one or more predetermined set of conditions, generating an electronic data package for transmission to the patient monitoring device, the electronic data package including location data regarding the at least one of the one or more points in the physiological sensor data that are likely indicative of the at least one of the one or more predetermined set of conditions.

In certain embodiments, a computerized method may comprise: accessing computer-executable instructions from at least one computer-readable storage medium; and executing the computer-executable instructions, thereby causing computer hardware comprising at least one computer processor to perform operations comprising: receiving, by a server computer through a communication link, physiological sensor data generated by a patient monitoring device, the physiological sensor data associated with a first patient; analyzing, by the server computer, the physiological sensor data to determine whether one or more points in the physiological data that are likely indicative of one or more predetermined set of conditions; and after determining that at least one of the one or more points in the physiological data is likely indicative of at least one of the one or more predetermined set of conditions, generating, by the server computer, an electronic data package for transmission to the patient monitoring device, the electronic data package including location data regarding the at least one of the one or more points in the physiological sensor data that are likely indicative of the at least one of the one or more predetermined set of conditions.

These and other aspects and embodiments of the invention are described in greater detail below, with reference to the drawing figures.

BRIEF DESCRIPTION OF THE DRAWINGS

FIGS. 2A and 2B are top perspective and bottom perspective views, respectively, of a printed circuit board assembly of the physiological monitoring device, according to one embodiment.

FIGS. 3A, 3B, 3C, 3D, and 3E are perspective and exploded views of a flexible body and gasket of the physiological monitoring device, according to one embodiment.

FIG. 4A schematically illustrates a top view of a portion of adhesive layer comprising vertical channels. FIG. 4B schematically illustrates an adhesive layer comprising column channels. FIGS. 4C and 4D schematically illustrate examples of an adhesive layer comprising lattice networks of channels. FIG. 4E schematically illustrates an adhesive layer comprising radially spiraling channels.

FIG. 5A schematically depicts a bottom view the physiological monitoring device, including the horizontal disposition of various constituent layers. FIG. 5B illustrates a support layer forming the main structure of the flexible body. FIG. 5C illustrates a close-up of the inset A depicted in FIG. 5B. FIG. 5D illustrates a central portion of the support layer configured to float over the skin of the subject between hinge lines of the flexible body. FIG. 5E illustrates perforated layers (e.g., perforated PET layers) comprising apertures for providing structural support to the wings while permitting moisture transmission according to some embodiments. FIG. 5F illustrates a close-up view of the inset A depicted in FIG. 5E. FIG. 5G depicts two adhesive layers. FIG. 5H depicts a perspective view of the physiological monitoring device.

FIGS. 6A-6H illustrate various views of embodiments of a physiological monitoring device. FIG. 6A depicts a perspective view, FIG. 6B shows a top view, FIG. 6C shows a bottom view, and FIG. 6D1 depicts a side view. FIG. 6D2 depicts a side view of a ridge configured for sealing the top and bottom portions of the housing. FIGS. 6E and 6F show a bottom and a top view of the physiological monitoring device with the layers illustrated transparently, to provide visualization through the device. FIGS. 6G and 6H illustrate exploded views of the various components of the physiological monitoring device.

FIGS. 8A-8J illustrate the various steps of assembling the physiological monitoring device and/or replacing the flexible body, including the adhesive layer, of the physiological monitoring device.

FIGS. 10A and 10B provide a perspective view of a battery holder of the physiological monitoring device, according to one embodiment.

DETAILED DESCRIPTION OF EMBODIMENTS

Figure 1A:
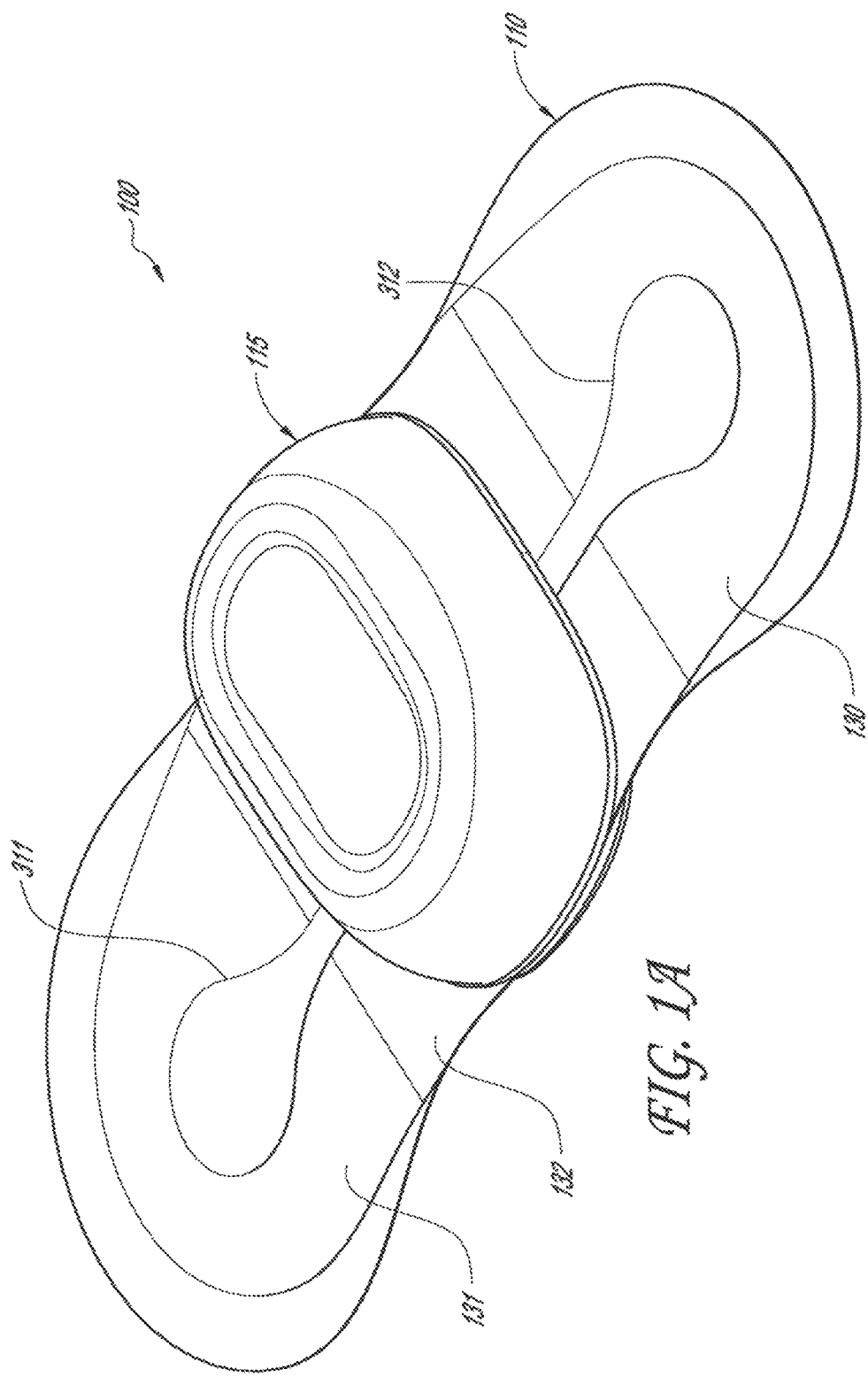
FIGS. 1A and 1B are perspective and exploded profile views, respectively, of a physiological monitoring device, according to one embodiment.

The following description is directed to a number of various embodiments. The described embodiments, however, may be implemented and/or varied in many different ways. For example, the described embodiments may be implemented in any suitable device, apparatus, or system to monitor any of a number of physiological parameters. For example, the following discussion focuses primarily on long-term, patch-based cardiac rhythm monitoring devices. In one alternative embodiment, a physiological monitoring device may be used, for example, for pulse oximetry and diagnosis of obstructive sleep apnea. The method of using a physiological monitoring device may also vary. In some cases, a device may be worn for one week or less, while in other cases, a device may be worn for at least seven days and/or for more than seven days, for example between fourteen days and twenty-one days or even longer. Many other alternative embodiments and applications of the described technology are possible. Thus, the following description is provided for exemplary purposes only. Throughout the specification, reference may be made to the term "conformal." It will be understood by one of skill in the art that the term "conformal" as used herein refers to a relationship between surfaces or structures where a first surface or structure adapts to the contours of a second surface or structure.

Since abnormal heart rhythms or arrhythmias can often be due to other, less serious causes, a key challenge is to determine when any of these symptoms are due to an arrhythmia. Oftentimes, arrhythmias occur infrequently and/or episodically, making rapid and reliable diagnosis difficult. As mentioned above, currently, cardiac rhythm monitoring is primarily accomplished through the use of devices, such as Holter monitors, that use short-duration (less than 1 day) electrodes affixed to the chest. Wires connect the electrodes to a recording device, usually worn on a belt. The electrodes need daily changing and the wires are cumbersome. The devices also have limited memory and recording time. Wearing the device interferes with patient movement and often precludes performing certain activities while being monitored, such as bathing. Further, Holter monitors are capital equipment with limited availability, a situation that often leads to supply constraints and corresponding testing delays. These limitations severely hinder the diagnostic usefulness of the device, the compliance of patients using the device, and the likelihood of capturing all important information. Lack of compliance and the shortcomings of the devices often lead to the need for additional devices, follow-on monitoring, or other tests to make a correct diagnosis.

Current methods to correlate symptoms with the occurrence of arrhythmias, including the use of cardiac rhythm monitoring devices, such as Holter monitors and cardiac event recorders, are often not sufficient to allow an accurate diagnosis to be made. In fact, Holter monitors have been shown to not lead to a diagnosis up to 90% of the time ("Assessment of the Diagnostic Value of 24-Hour Ambulatory Electrocardiographic Monitoring", by DE Ward et al. Biotelemetry Patient Monitoring, vol. 7, published in 1980).

Additionally, the medical treatment process to actually obtain a cardiac rhythm monitoring device and initiate monitoring is typically very complicated. There are usually numerous steps involved in ordering, tracking, monitoring, retrieving, and analyzing the data from such a monitoring device. In most cases, cardiac monitoring devices used today are ordered by a cardiologist or a cardiac electrophysiologist (EP), rather than the patient's primary care physician (PCP). This is of significance since the PCP is often the first physician to see the patient and determine that the patient's symptoms could be due to an arrhythmia. After the patient sees the PCP, the PCP will make an appointment for the patient to see a cardiologist or an EP. This appointment is usually several weeks from the initial visit with the PCP, which in itself leads to a delay in making a potential diagnosis as well as increases the likelihood that an arrhythmia episode will occur and go undiagnosed. When the patient finally sees the cardiologist or EP, a cardiac rhythm monitoring device will usually be ordered. The monitoring period can last 24 to 48 hours (Holter monitor) or up to a month (cardiac event monitor or mobile telemetry device). Once the monitoring has been completed, the patient typically must return the device to the clinic, which itself can be an inconvenience. After the data has been processed by the monitoring company or by a technician on-site at a hospital or office, a report will finally be sent to the cardiologist or EP for analysis. This complex process results in fewer patients receiving cardiac rhythm monitoring than would ideally receive it.

To address some of these issues with cardiac monitoring, the assignee of the present application developed various embodiments of a small, long-term, wearable, physiological monitoring device. One embodiment of the device is the Zio® Patch. Various embodiments are also described, for example, in U.S. Pat. Nos. 8,150,502, 8,160,682 8,244,335, 8,560,046, 8,538,503, 9,173,670, and 9,597,004, and U.S. Pat. Pub. No. 2018/0289274 A1, the full disclosures of which are hereby incorporated herein by reference. Generally, the physiological patch-based monitors described in the above references fit comfortably on a patient's chest and are designed to be worn for at least one week and typically two to three weeks. The monitors detect and record cardiac rhythm signal data continuously while the device is worn, and this cardiac rhythm data is then available for processing and analysis.

These smaller, long-term, patch-based physiological monitoring devices provide many advantages over prior art devices. At the same time, further improvements are desired. One of the most meaningful areas for improvement is to offer more timely notice of critical arrhythmias to managing clinicians. The hallmark of these initial embodiments was that—for reasons of performance, compliance and cost—the device only recorded information during the extended wear period, with analysis and reporting occurring after the recording completed. Thus, a desirable improvement would be to add the capability of either real-time or timely analysis of the collected rhythm information. While diagnostic monitors with such timely reporting capabilities currently exist, they require one or more electrical components of the system to be either regularly recharged or replaced. These actions are associated with reduced patient compliance and, in turn, reduced diagnostic yield. As such, a key area of improvement is to develop a physiologic monitor that can combine long-term recording with timely reporting without requiring battery recharging or replacement.

Patient compliance and device adhesion performance are two factors that govern the duration of the ECG record and consequently the diagnostic yield. Compliance can be increased by improving the patient's wear experience, which is affected by wear comfort, device appearance, and the extent to which the device impedes the normal activities of daily living. Given that longer ECG records provide greater diagnostic yield and hence value, improvements to device adhesion and patient compliance are desirable.

Signal quality is important throughout the duration of wear, but may be more important where the patient marks the record, indicating an area of symptomatic clinical significance. Marking the record is most easily enabled through a trigger located on the external surface of the device. However, since the trigger may be part of a skin-contacting platform with integrated electrodes, the patient can introduce significant motion artifacts when feeling for the trigger. A desirable device improvement would be a symptom trigger that can be activated with minimal addition of motion artifact.

Further, it is desirable for the device to be simple and cost effective to manufacture, enabling scalability at manufacturing as well as higher quality due to repeatability in process. Simplicity of manufacture can also lead to ease of disassembly, which enables the efficient recovery of the printed circuit board for quality-controlled reuse in another device. Efficient reuse of this expensive component can be important for decreasing the cost of the diagnostic monitor.

There remain clinical scenarios where still longer-duration and lower-cost solutions may be a valuable addition to a portfolio of cardiac ambulatory monitoring options. Inspiration for a potential solution to these needs can be found in the continuous heart rate sensing functionality that is increasingly being incorporated in a variety of consumer health and fitness products, including smart watches and wearable fitness bands. Although continuous heart rate data can be used to provide the user with information about their general fitness levels, it is more both more challenging and valuable to use this data to provide meaningful information related to their health and wellness. For example, the ability to detect potential arrhythmias from continuous heart rate data would enable consumer devices incorporating heart rate sensing functionality to serve as potential screening tools for the early detection of cardiac abnormalities. Such an approach could be clinically valuable in providing a long-term, cost-effective screening method for at-risk populations, for example, heart failure patients at risk for Atrial Fibrillation. Alternatively, this monitoring approach could be helpful in the long-term titration of therapeutic drug dosages to ensure efficaciousness while reducing side effects, for example, in the management of Paroxysmal Atrial Fibrillation. Beyond cardiac arrhythmia detection, the appropriate analysis of heart rate information could also yield insight into sleep and stress applications.

Long-term ambulatory monitoring with a physiologic device, such as an adhesive patch, has a number of clinical applications, particularly when timely information about the occurrence and duration of observed arrhythmias can be provided during the monitoring period. In terms of prevalence, particularly as driven by an aging population, efficiently detecting Atrial Fibrillation (AF) remains the most significant monitoring need. This need is not just evident for patients presenting with symptoms, but also given the increased risk of stroke associated with this arrhythmia for broader, population-based monitoring of asymptomatic AF in individuals at risk due to one or more factors of advanced age, the presence of chronic illnesses like Heart Disease, or even the occurrence of surgical procedures. For the latter group, both perioperative and post-procedure monitoring can be clinically valuable, and not just for procedures targeted at arrhythmia prevention (for example, the MAZE ablation procedure, or hybrid endo and epicardial procedures, both for treatment of AF), but also for general surgeries involving anesthesia. For some applications, the goal of ambulatory monitoring for Atrial Fibrillation will sometimes be focused on the simple binary question of whether AF did occur in a given time period. For example, monitoring a patient following an ablation procedure will typically seek to confirm success, typically defined as the complete lack of AF occurrence. Likewise, monitoring a patient post-stroke will be primarily concerned with evaluating the presence of Atrial Fibrillation.

However, even in those scenarios, if AF occurs, it may be clinically meaningful to evaluate additional aspects to better characterize the occurrence, such as daily burden (% of time in AF each day), and duration of episodes (expressed, for example, as a histogram of episode duration, or as the percentage of episodes that extend beyond a specified limit, say six minutes), both either in absolute terms or in comparison to prior benchmarks (for example, from a baseline, pre-procedure monitoring result). Indeed, measuring daily AF burden, evaluating AF episode duration, and reviewing AF occurrence during sleep and waking periods, and evaluating the presence of AF in response to the degree of a patient's physical movement can be important in a variety of clinical scenarios, including evaluating the effectiveness of drug-based treatment for this arrhythmia.

Making this information available in a timely manner during the monitoring period could allow the managing physician to iteratively titrate treatment, for example, by adjusting the dosage and frequency of a novel oral anticoagulant drug (NOAC) until management was optimized. A further example of this management paradigm is for the patient to be notified of asymptomatic AF—either directly by the device through audible or vibration-based alert, through notification from an application connected to the device, or via phone, email or text-message communication from the managing clinician—for the timely application of a "pill in the pocket" for AF management.

The theme of timely management and/or intervention is certainly evident in situations where clinically significant arrhythmias are observed, for example, asymptomatic second-degree and complete Heart Block, extended pauses, high-rate supraventricular tachycardias, prolonged ventricular tachycaridas, and ventricular fibrillation. For example, the clinical scenario where an extended pause or complete heart block causes Syncope is a particularly significant case where the availability of a timely and dependable monitoring method could reduce or even eliminate the need for in-hospital monitoring of at-risk patients. The theme can also extend to more subtle changes in morphology, for example, QT prolongation in response to medications, which has been shown to have significant cardiac safety implications. Timely awareness of such prolongation could lead, for example, to early termination of clinical studies evaluating drug safety and effectiveness or, alternatively, to adjusting the dosage or frequency as a means to eliminate observed prolongation.

Physiological Monitoring Devices

Figure 1B:
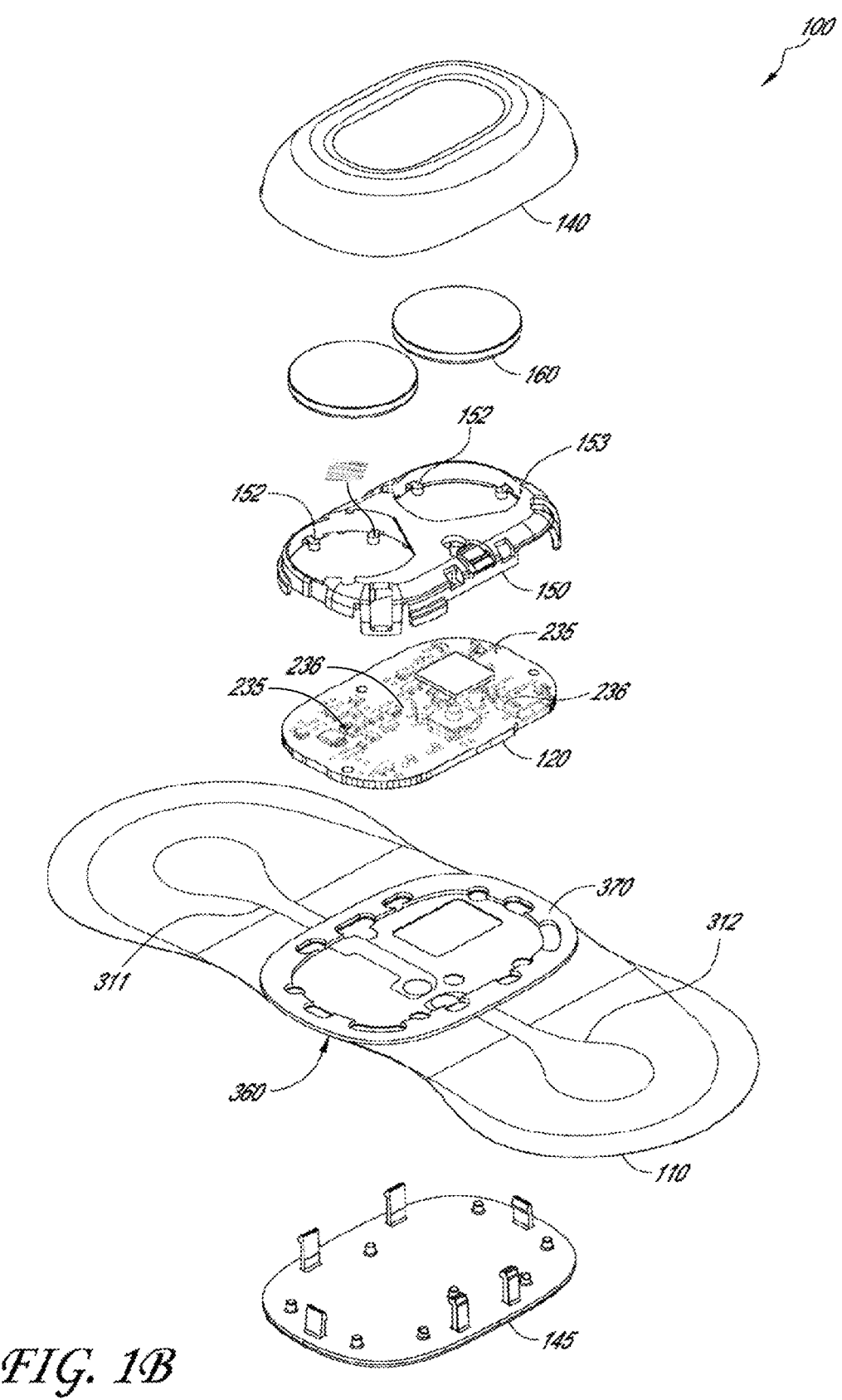

Referring to FIGS. 1A and 1B, perspective and exploded profile views of one embodiment of a physiological monitoring device 100 are provided. As seen in FIG. 1A, physiological monitoring device 100 may include a flexible body 110 coupled with a watertight, housing 115. As will be understood by one of skill in the art, the housing as described herein and throughout this specification, may be constructed from rigid or flexible materials, thereby rendering the housing rigid, such as to resist deformation or soft such as to flex and/or deform with force. Flexible body 110 (which may be referred to as "flexible substrate" or "flexible construct") typically includes two wings 130, 131, which extend laterally from housing 115, and two flexible electrode traces 311, 312, each of which is embedded in one of wings 130, 131. Each electrode trace 311, 312 is coupled, on the bottom surface of flexible body 110, with a flexible electrode (not visible in FIG. 1A). The electrodes are configured to sense heart rhythm signals from a patient to which monitoring device 100 is attached. Electrode traces 311, 312 then transmit those signals to electronics (not visible in FIG. 1A) housed in housing 115. Housing 115 also typically contains a power source, such as one or more batteries.

The combination of a highly flexible body 110, including flexible electrodes and electrode traces 311, 312, with a very housing 115 may provide a number of advantages. A key advantage is high fidelity signal capture. The highly conformal and flexible wings 130, 131, electrodes and traces 311, 312 limit the transmission of external energy to the electrode-skin interface. If motion is imparted to the housing 115, for example, the system of conformal adhesion to the skin limits the extent to which that motion affects the monitored signal. Flexible electrode traces 311, 312 generally may help provide conformal contact with the subject's skin and may help prevent electrodes 350 (electrodes 350 are not visible in FIG. 1, but are visible in FIG. 6A described below) from peeling or lifting off of the skin, thereby providing strong motion artifact rejection and better signal quality by minimizing transfer of stress to electrodes 350. Furthermore, flexible body 110 includes a configuration and various features that facilitate comfortable wearing of device 100 by a patient for fourteen (14) days or more without removal. Housing 115, which typically does not adhere to the patient in the embodiments described herein, includes features that lend to the comfort of device 100. Hinge portions 132 are relatively thin, even more flexible portions of flexible body 110. They allow flexible body 110 to flex freely at the area where it is joined to housing 115. This flexibility enhances comfort, since when the patient moves, housing 115 can freely lift off of the patient's skin. Electrode traces 311, 312 are also very thin and flexible, to allow for patient movement without signal distortion.

Referring now to FIG. 1B, a partially exploded view of physiological monitoring device 100 illustrates component parts that make up, and that are contained within, housing 115 in greater detail. In this embodiment, housing 115 includes an upper housing member 140, which detachably couples with a lower housing member 145. Sandwiched between upper housing member 140 and lower housing member 145 are an upper gasket 370, and a lower gasket 360 (not visible on FIG. 1B but just below upper gasket 370). Gaskets 370, 360 help make housing 115 watertight when assembled. A number of components of monitoring device 100 may be housed between upper housing member 140 and lower housing member 145. For example, in one embodiment, housing 115 may contain a portion of flexible body 110, a printed circuit board assembly (PCBA) 120, a battery holder 150, and two batteries 160. Printed circuit board assembly 120 is positioned within housing 115 to contact electrode traces 311, 312 and batteries 160. In various embodiments, one or more additional components may be contained within or attached to housing 115. Some of these optional components are described further below, in reference to additional drawing figures.

Battery holder 150, according to various alternative embodiments, may hold two batteries (as in the illustrated embodiment), one battery, or more than two batteries. In other alternative embodiments, other power sources may be used. In the embodiment shown, battery holder 150 includes multiple retain tabs 153 for holding batteries 160 in holder 150. Additionally, battery holder 150 includes multiple feet 152 to establish correct spacing of batteries 160 from the surface of PCBA 120 and ensure proper contact with spring fingers and/or contacts 235 and 236. Spring fingers 235 and 236 are used in this embodiment rather than soldering batteries 160 to PCBA 120. Although soldering may be used in alternative embodiments, one advantage of spring fingers 235 and 236 is that they allow batteries 160 to be removed from PCBA 120 and holder 150 without damaging either of those components, thus allowing for multiple reuses of both. Eliminating solder connections also simplifies and speeds up assembly and disassembly of monitoring device 100.

In some embodiments, upper housing member 140 may act as a patient event trigger. When a patient is wearing physiological monitoring device 100 for cardiac rhythm monitoring, it is typically advantageous for the patient to be able to register with device 100 (for example, log into the device's memory) any cardiac events perceived by the patient. If the patient feels what he/she believes to be an episode of heart arrhythmia, for example, the patient may somehow trigger device 100 and thus provide a record of the perceived event. In some embodiments, trigger of perceived events by the patient may initiate transmission of data associated with the triggered event. In some embodiments, trigger of perceived events may simply mark a continuous record with the location of the triggered event. In some embodiments, both transmission of associated data as well as marking of the continuous record may occur. At some later time, the patient's recorded symptom during the perceived event could be compared with the patient's actual heart rhythm, recorded by device 100, and this may help determine whether the patient's perceived events correlate with actual cardiac events. One problem with patient event triggers in currently available wearable cardiac rhythm monitoring devices, however, is that a small trigger may be hard to find and/or activate, especially since the monitoring device is typically worn under clothing. Additionally, pressing a trigger button may affect the electronics and/or the electrodes on the device in such a way that the recorded heart rhythm signal at that moment is altered simply by the motion caused to the device by the patient triggering. For example, pressing a trigger may jar one or both of the electrodes in such a way that the recorded heart rhythm signal at that moment appears like an arrhythmia, even if no actual arrhythmia event occurred. Additionally, there is a chance that the trigger may be inadvertently activated, for instance while sleeping or laying on the monitoring device.

In the embodiment shown in FIGS. 1A and 1B, however, housing 115 is sufficiently rigid, and flexible body 110 is sufficiently flexible, that motion applied to housing 115 by a patient may rarely or ever cause an aberrant signal to be sensed by the electrodes. In this embodiment, the central portion of upper housing member 140 is slightly concave and, when pressed by a patient who is wearing device 100, this central portion depresses slightly to trigger a trigger input on PCBA 120. Because the entire upper surface of housing 115 acts as the patient event trigger, combined with the fact that it is slightly concave, it will generally be quite easy for a patient to find and push down the trigger, even under clothing. Additionally, the concave nature of the button allows it to be recessed which protects it from inadvertent activations. Thus, the present embodiment may alleviate some of the problems encountered with patient event triggers on currently available heart rhythm monitors. These and other aspects of the features shown in FIGS. 1A and 1B will be described in further detail below.

Figure 2B:
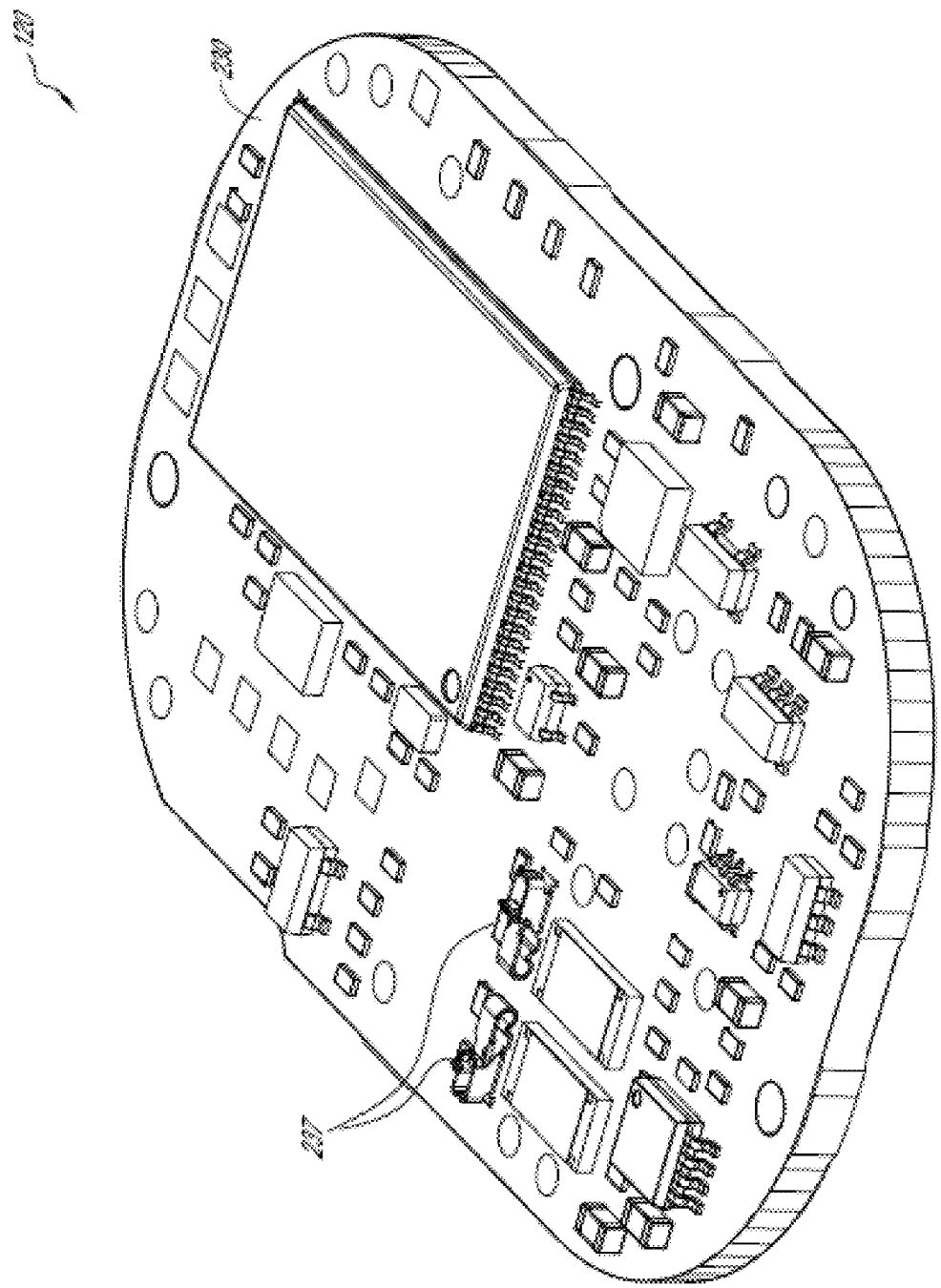

Referring now to the embodiments in FIGS. 2A and 2B, printed circuit board assembly 120 (or PCBA) may include a top surface 220, a bottom surface 230, a patient trigger input 210 and spring contacts 235, 236, and 237. Printed circuit board assembly 120 may be used to mechanically support and electrically connect electronic components using conductive pathways, tracks or electrode traces 311, 312. Furthermore, because of the sensitive nature of PCBA 120 and the requirement to mechanically interface with rigid housing 115, it is beneficial to have PCBA 120 be substantially rigid enough to prevent unwanted deflections which may introduce noise or artifact into the ECG signal. This is especially possible during patient trigger activations when a force is transmitted through rigid housing 115 and into PCBA 120. One way to ensure rigidity of the PCBA is in some embodiments, to ensure that the thickness of the PCBA is relatively above a certain value. For example, a thickness of at least about 0.08 cm is desirable and, more preferably, a thickness of at least about 0.17 cm is desirable. In this application, PCBA 120 may also be referred to as, or substituted with, a printed circuit board (PCB), printed wiring board (PWB), etched wiring board, or printed circuit assembly (PCA). In some embodiments, a wire wrap or point-to-point construction may be used in addition to, or in place of, PCBA 120. PCBA 120 may include analog circuits and digital circuits.

Patient trigger input 210 may be configured to relay a signal from a patient trigger, such as upper housing member 140 described above, to PCBA 120. For example, patient trigger input 210 may be a PCB switch or button that is responsive to pressure from the patient trigger (for example, the upper surface of upper housing member portion 140). In various embodiments, patient trigger input 210 may be a surface mounted switch, a tactile switch, an LED illuminated tactile switch, or the like. In some embodiments, patient trigger input 210 may also activate an indicator, such as an LED. Certain embodiments may involve a remotely located trigger such as on a separate device or as a smart phone app.

One important challenge in collecting heart rhythm signals from a human or animal subject with a small, two-electrode physiological monitoring device such as device 100 described herein, is that having only two electrodes can sometimes provide a limited perspective when trying to discriminate between artifact and clinically significant signals. For example, when a left-handed patient brushes her teeth while wearing a small, two-electrode physiological monitoring device on her left chest, the tooth brushing may often introduce motion artifact that causes a recorded signal to appear very similar to Ventricular Tachycardia, a serious heart arrhythmia. Adding additional leads (and, hence, vectors) is the traditional approach toward mitigating this concern, but this is typically done by adding extra wires adhered to the patient's chest in various locations, such as with a Holter monitor. This approach is not consistent with a small, wearable, long term monitor such as physiological monitoring device 100.

An alternate approach to the problem described above is to provide one or more additional data channels to aid signal discrimination. In some embodiments, for example, device 100 may include a data channel for detecting patch motion. In certain embodiments, an accelerometer or other suitable device may provide patch motion by simply analyzing the change in magnitude of a single axis measurement, or alternatively of the combination of all three axes. The accelerometer may record device motion at a sufficient sampling rate to allow algorithmic comparison of its frequency spectrum with that of the recorded ECG signal. If there is a match between the motion and recorded signal, it is clear that the device recording in that time period is not from a clinical (for example, cardiac) source, and thus that portion of the signal can be confidently marked as artifact. This technique may be particularly useful in the tooth brushing motion example aforementioned, where the rapid frequency of motion as well as the high amplitude artifact is similar to the heart rate and morphology, respectively, of a potentially life-threatening arrhythmia like Ventricular Tachycardia. Other suitable devices described herein this section and elsewhere in the specification may also be utilized to provide motion information.

In some embodiments, using the magnitude of all three axes for such an analysis would smooth out any sudden changes in values due to a shift in position rather than a change in activity. In other embodiments, there may be some advantage in using a specific axis of measurement such as along the longitudinal axis of the body to focus on a specific type of artifact introduced by upward and downward movements associated with walking or running. In a similar vein, the use of a gyroscope in conjunction with the accelerometer may provide further resolution as to the nature of the motion experienced. While whole body movements may be sufficiently analyzed with an accelerometer on its own, specific motion of interest such as rotational motion due to arm movement is sufficiently complex that an accelerometer alone might not be able to distinguish.

In addition to detecting motion artifact, an accelerometer tuned to the dynamic range of human physical activities may provide activity levels of the patient during the recording, which can also enhance accuracy of algorithmic true arrhythmia detection. Given the single-lead limitation of device 100, arrhythmias that require observation of less prominent waves (for example P-wave) in addition to rate changes such as Supraventricular Tachycardia pose challenges to both computerized algorithms as well as the trained human eye. This particular arrhythmia is also characterized by the sudden nature of its onset, which may be more confidently discriminated from a non-pathological Sinus Tachycardia if a sudden surge in the patient's activity level is detected at the same time as the increase in heart rate. Broadly speaking, the provision of activity information to clinical professionals may help them discriminate between exercise-induced arrhythmia versus not. As with motion artifact detection, a single-axis accelerometer measurement optimized to a particular orientation may aid in more specifically determining the activity type such as walking or running. This additional information may help explain symptoms more specifically and thereby affect the subsequent course of therapeutic action.

In certain embodiments, an accelerometer with 3 axes may confer advantages beyond what magnitude of motions can provide. When the subject is not rapidly moving, 3-dimensional accelerometer readings may approximate the tilt of PCBA 120, and therefore body orientation relative to its original orientation. The original body orientation can be assumed to be in either an upright or supine position which is required for appropriate positioning and application of the device to the body. This information may aid in ruling out certain cardiac conditions that manifest as beat-to-beat morphology changes, such as cardiac *alternans* where periodic amplitude changes are observed, often in heart failure cases. Similar beat-to-beat morphology changes are observable in healthy subjects upon shift in body position due to the shift in heart position relative to the electrode vector, for example from an upright to a slouching position. By design, the single-channel device 100 does not have an alternate ECG channel to easily rule out potential pathological shifts in morphology, however, correlation with shifts in body orientation will help explain these normal changes and avoid unnecessary treatment due to false diagnosis.

In other embodiments, the accelerometer may also be used as a sleep indicator, based on body orientation and movement. When presenting clinical events (for example, pauses), it is diagnostically helpful to be able to present information in a manner that clearly separates events that occurred during sleep from those during waking hours. In fact, certain algorithms such as for ECG-derived respiratory rate only make sense to run when the patient is in a relatively motionless state and therefore subtle signal modulation introduced by chest movement due to breathing is observable. Respiratory rate information is useful as one channel of information necessary to detect sleep apnea in certain patient populations.

In certain embodiments, the accelerometer may also be used to detect free-falls, such as fainting. With an accelerometer, device 100 may be able to mark fainting (syncope) and other free-fall events without relying on patient trigger. In some embodiments, such free-fall event triggers may initiate transmission of associated data. In order to allow timely detection of such critical events, yet considering the battery and memory limitations of a small, wearable device such as device 100, acquisition of accelerometer readings may be done in bursts, where only interesting information such as a potential free fall is written to memory at a high sampling rate. An expansion of this event-trigger concept is to use specific tapping motions on device 100 as a patient trigger instead of or in conjunction with the button previously described. The use and detection of multiple types of tapping sequences may provide better resolution and accuracy into what exactly the patient was feeling, instead of relying on the patient to manually record their symptom and duration in a trigger log after the fact. An example of such added resolution is to indicate the severity of the symptom by the number of sequential taps.

Alternatively, in other embodiments, optical sensors may be used to distinguish between device motion and patient body motion. Further, in additional embodiments, the device may not require a button or trigger. In still more embodiments, suitable devices described herein this section or elsewhere in the specification may also be used.

Another optional data channel that may be added to physiological monitoring device 100 is a channel for detecting flex and/or bend of device 100. In various embodiments, for example, device 100 may include a strain gauge, piezoelectric sensor or optical sensor to detect motion artifact in device 100 itself and thus help to distinguish between motion artifact and cardiac rhythm data. Yet another optional data channel for device 100 may be a channel for detecting heart rate. For example, a pulse oximeter, microphone or stethoscope may provide heart rate information. Redundant heart rate data may facilitate discrimination of ECG signals from artifact. This is particularly useful in cases where arrhythmia such as Supraventricular Tachycardia is interrupted by artifact, and decisions must be made whether the episode was actually multiple shorter episodes or one sustained episode. Another data channel may be included for detecting ambient electrical noise. For example, device 100 may include an antenna for picking up electromagnetic interference. Detection of electromagnetic interference may facilitate discrimination of electrical noise from real ECG signals. Any of the above-described data channels may be stored to support future noise discrimination or applied for immediate determination of clinical validity in real-time.

Figure 3A:
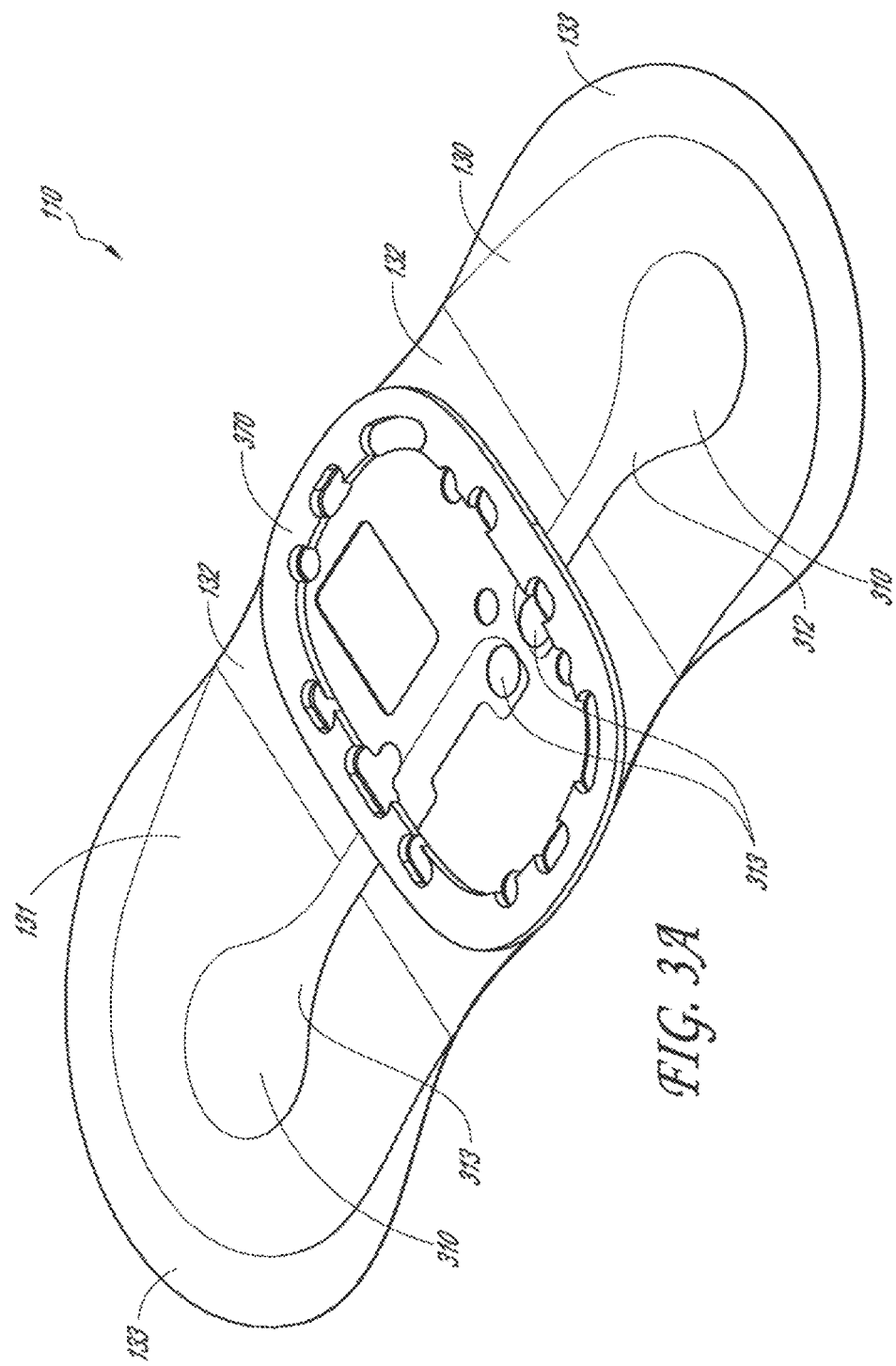
Figure 3B:
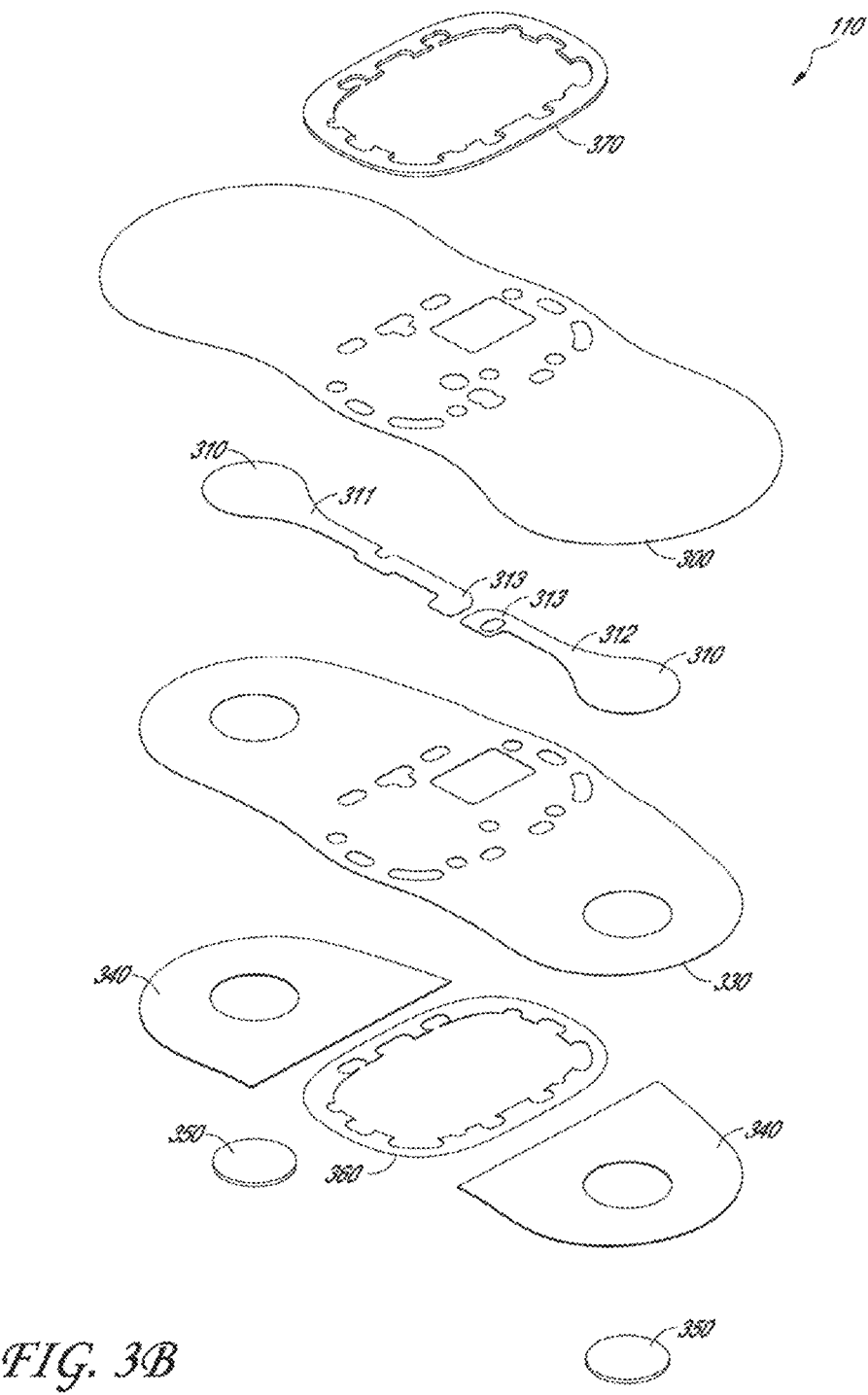

With reference now to the embodiments of FIGS. 3A and 3B, flexible body 110 is shown in greater detail. As illustrated in FIG. 3A, flexible body 110 may include wings 130, 131, a thin border 133 (or "rim" or "edge") around at least part of each wing 130, 131, electrode traces 311, 312, and a hinge portion 132 (or "shoulder") at or near a junction of each wing 130, 131 with housing 115. Also shown in FIG. 3A is upper gasket 370, which is not considered part of flexible body 110 for this description, but which facilitates attachment of flexible body 110 to housing 115.

Hinge portions 132 are relatively thin, even more flexible portions of flexible body 110. They allow flexible body 110 to flex freely at the area where it is joined to housing 115. This flexibility enhances comfort, since when the patient moves, housing 115 can freely lift off of the patient's skin. Electrode traces 311, 312 are also very thin and flexible, to allow for patient movement without signal distortion. Borders 133 are portions of flexible body 110 that is thinner than immediately adjacent portions and that provide for a smooth transition from flexible body 110 to a patient's skin, thus preventing edge-lift and penetration of dirt or debris below flexible body 110.

As shown in greater detail in FIG. 3B, flexible body 110 may include multiple layers. As mentioned previously, in some embodiments, upper gasket 370 and lower gasket 360 are not considered part of flexible body 110 for the purposes of this description but are shown for completeness of description. This distinction is for ease of description only, however, and should not be interpreted to limit the scope of the described embodiments. Flexible body 110 may include a top substrate layer 300, a bottom substrate layer 330, an adhesive layer 340, and flexible electrodes 350. Top and bottom substrate layers 300, 330 may be made of any suitable, flexible material, such as one or more flexible polymers. Suitable flexible polymers can include, but are not limited to, polyurethane, polyethylene, polyester, polypropylene, nylon, teflon and carbon impregnated vinyl. The material of substrate layers 300, 330 may be selected based on desired characteristics. For example, the material of substrate layers 300, 330 may be selected for flexibility, resilience, durability, breathability, moisture transpiration, adhesion and/or the like. In one embodiment, for example, top substrate layer 300 may be made of polyurethane, and bottom substrate layer 330 may be made of polyethylene or alternatively polyester. In other embodiments, substrate layers 300, 330 may be made of the same material. In yet another embodiment, substrate layer 330 may contain a plurality of perforations in the area over adhesive layer 340 to provide for even more breathability and moisture transpiration. In various embodiments, physiological monitoring device 100 may be worn continuously by a patient for as many as 14-21 days or more, without removal during the time of wear and with device 100 being worn during showering, exercising and the like. Thus, the material(s) used and the thickness and configuration of substrate layers 300, 330 affect the function of physiological monitoring device 100. In some embodiments, the material of substrate layers 300, 330 acts as an electric static discharge (ESD) barrier to prevent arcing.

Typically, top and bottom substrate layers 300, 330 are attached to one another via adhesive placed on one or both layers 300, 330. For example, the adhesive or bonding substance between substrate layers 300, 330 may be an acrylic-based, rubber-based, or silicone-based adhesive. In other alternative embodiments, flexible body 110 may include more than two layers of flexible material.

In addition to the choice of material(s), the dimensions—thickness, length and width—of substrate layers 300, 330 may be selected based on desired characteristics of flexible body 110. For example, in various embodiments, the thickness of substrate layers 300, 330 may be selected to give flexible body 110 an overall thickness of between about 0.1 mm to about 1.0 mm. According to various embodiments, flexible body 110 may also have a length of between about 7 cm and 15 cm and a width of about 3 cm and about 6 cm. Generally, flexible body 110 will have a length sufficient to provide a necessary amount of separation between electrodes 350. For example, in one embodiment a distance from the center of one electrode 350 to the center of the other electrode 350 should be at least about 6.0 cm and more preferably at least about 8.5 cm. This separation distance may vary, depending on the application. In some embodiments, substrate layers 300, 330 may all have the same thickness. Alternatively, the two substrate layers 300, 330 may have different thicknesses.

As mentioned above, hinge portions 132 allow the rigid housing 115 to lift away from the patient while flexible body 110 remains adhered to the skin. The functionality of hinge portions 132 is critical in allowing the device to remain adhered to the patient throughout various activities that may stretch and compress the skin. Furthermore, hinge portions 132 allow for significantly improved comfort while wearing the device. Generally, hinge portions 132 will be sufficiently wide enough to provide adequate lift of rigid housing 115 without creating too large of a peel force on flexible body 110. For example, in various embodiments, the width of hinge portion 132 should be at least about 0.25 cm and more preferably at least about 0.75 cm.

Additionally, the shape or footprint of flexible body 110 may be selected based on desired characteristics. As seen in FIG. 3A, wings 130, 131 and borders 133 may have rounded edges that give flexible body 110 an overall "peanut" shape. However, wings 130, 131 can be formed in any number of different shapes such as rectangles, ovals, loops, or strips. In the embodiment shown in FIGS. 3A and 3B, the footprint top substrate layer 300 is larger than the footprint of bottom substrate layer 330, with the extension of top substrate layer 300 forming borders 133. Thus, borders 133 are made of the same polyurethane material that top layer 300 is made of. Borders 133 are thinner than an adjacent portion of each wing 130, 131, since they includes only top layer 300. The thinner, highly compliant rim and/or border 133 will likely enhance adherence of physiologic monitoring device 100 to a patient, as it provides a transition from an adjacent, slightly thicker portion of wings 130, 131 to the patient's skin and thus helps prevent the edge of the flexible body 110 from peeling up off the skin. Border 133 may also help prevent the collection of dirt and other debris under flexible body 110, which may help promote adherence to the skin and also enhance the aesthetics of the flexible body 110. In some embodiments, the border 133 may comprise a width (e.g., from an outer edge of the border 133 to an inner edge of the border 133) of at least about 3 mm, 6 mm, 9 mm, 12 mm, or 15 mm. In alternative embodiments, the footprint of substrate layers 300, 330 may be the same, thus eliminating borders 133.

While the illustrated embodiments of FIGS. 1A-3B include only two wings 130, 131, which extend from housing 115 in approximately opposite directions (for example, at a 180-degree angle relative to each other), other configurations are possible in alternative embodiments. For example, in some embodiments, wings 130, 131 may be arranged in an asymmetrical orientation relative to one another and/or one or more additional wings may be included. As long as sufficient electrode spacing is provided to permit physiological signal monitoring, and as long as wings 130, 131 are configured to provide extended attachment to the skin, any suitable configuration and number of wings 130, 131 and electrode traces 311, 312 may be used. The embodiments described above have proven to be advantageous for adherence, patient comfort and accuracy of collected heart rhythm data, but in alternative embodiments it may be possible to implement alternative configurations.

Adhesive layer 340 is an adhesive that is applied to two portions of the bottom surface of bottom substrate layer 330, each portion corresponding to one of wings 130, 131. Adhesive layer 340 thus does not extend along the portion of bottom substrate layer 330 upon which housing 115 is mounted. Adhesive layer 340 may be made of any suitable adhesive, although certain adhesives have been found to be advantageous for providing long term adhesion to patient skin with relative comfort and lack of skin irritation. For example, in one embodiment, adhesive layer 340 is a hydrocolloid adhesive. In another embodiment, the adhesive layer 340 is comprised of a hydrocolloid adhesive that contains naturally-derived or synthetic absorbent materials which take up moisture from the skin during perspiration.

With reference now to FIG. 3B, each of the two portions of adhesive layer 340 includes a hole, into which one of electrodes 350 fits. Electrodes 350 are made of flexible material to further provide for overall conformability of flexible body 110. In one embodiment, for example, flexible electrodes 350 may be made of a hydrogel. Electrodes 350 generally provide conformal, non-irritating contact with the skin to provide enhanced electrical connection with the skin and reduce motion artifact. In some embodiments, hydrogel electrodes 350 may be punched into adhesive layer 340, thus forming the holes and filling them with hydrogel electrodes 350. In one alternative embodiment, electrodes 350 and adhesive 340 may be replaced with an adhesive layer made of a conductive material, such that the entire adhesive layer on the underside of each wing 130, 131 acts as an electrode. Such an adhesive layer may include a hybrid adhesive/conductive substance or adhesive substance mixed with conductive elements or particles. For example, in one embodiment, such an adhesive layer may be a hybrid of a hydrogel and a hydrocolloid adhesive. Housing 115 of FIG. 1A also protects the electronics and power source contained in the housing and/or the PCBA 120, enhances the ability of a patient to provide an input related to a perceived cardiac event, and allows for simple manufacturing and reusability of at least some of the contents of housing 115. These and other features of physiological monitoring device 100 are described in greater detail below.

As discussed above, in some embodiments, adhesive layer 340 may cover a portion of the underside of lower substrate layer 330, such that at least a portion of the bottom side of flexible body 110 does not include adhesive layer 340. As seen in FIG. 3A, hinges 132 may be formed in the flexible body 110 as portions of each wing 130, 131 on which adhesive layer 340 is not applied. Hinge portions 132 are generally located at or near the junction of flexible body 110 with housing 115, and thus provide for flexing of device 100 to accommodate patient movement. In some embodiments, hinge portions 132 may have a width that is less than that of adjacent portions of wings 130, 131, thus giving device 100 its "peanut" shape mentioned above. As shown in FIG. 8, as a subject moves, device 100 flexes along with patient movement. Device flexion may be severe and is likely to occur many times during long term monitoring. Hinge portions 132 may allow for dynamic conformability to the subject, while the rigidity of housing 115 may allow housing 115 to pop up off the patient's skin during device flexion, thus preventing peeling of the device 100 off of the skin at its edge.

Figure 3D:
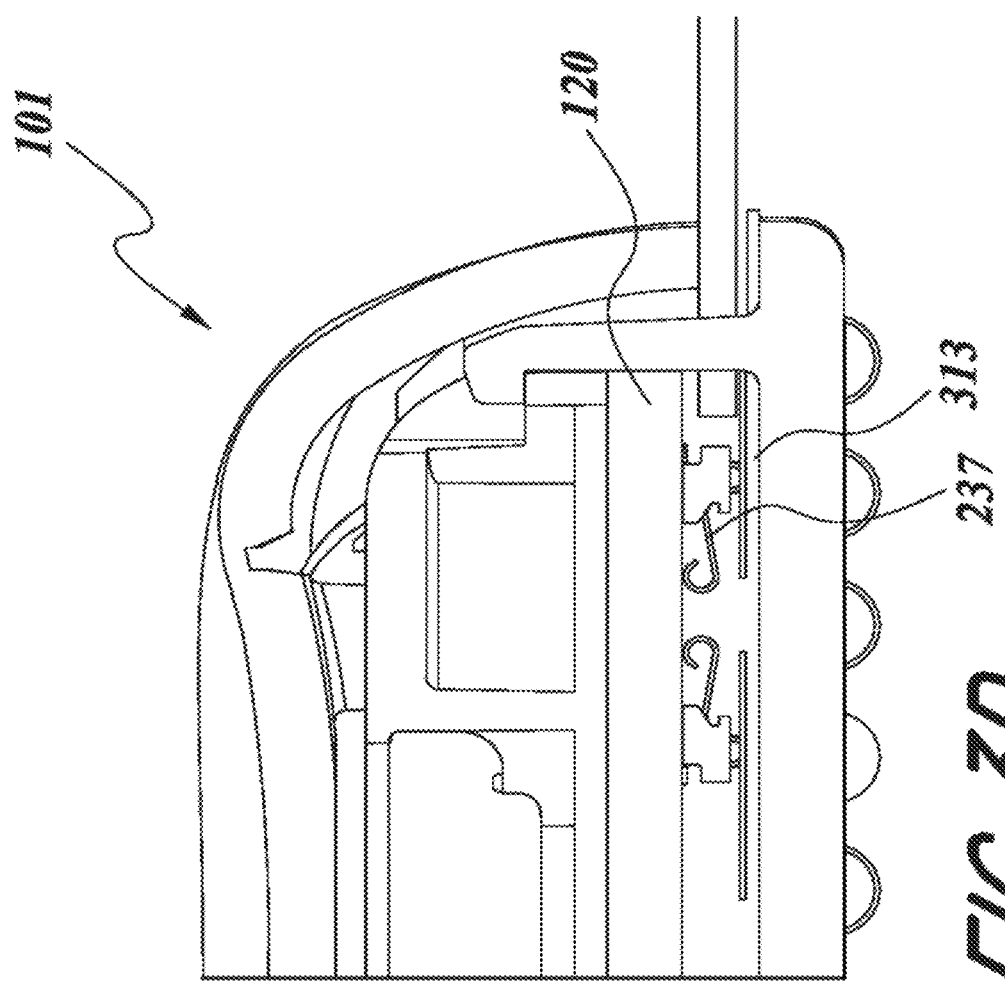

Flexible body 110 further includes two electrode traces 311, 312 sandwiched between upper substrate layer 300 and lower substrate layer 330. Each electrode trace 311, 312 may include an electrode interface portion 310 and an electrocardiogram circuit interface portion 313. As illustrated in the embodiments of FIGS. 3C and 3D, ECG circuit interface portions 313 are in physical contact with spring fingers 237 and provide electrical communication with PCBA 120 when device 100 or zoomed-in device portion 101 is assembled. Electrode interface portions 310 contact hydrogel electrodes 350. Thus, electrode traces 311, 312 transmit cardiac rhythm signals (and/or other physiological data in various embodiments) from electrodes 350 to PCBA 120.

The material and thickness of electrode traces 311, 312 are important for providing a desired combination of flexibility, durability and signal transmission. For example, in one embodiment, electrode traces 311, 312 may include a combination of silver (Ag) and silver chloride (AgCl). The silver and silver chloride may be disposed in layers. For example, one embodiment of electrode traces 311, 312 may include a top layer of silver, a middle layer of carbon impregnated vinyl, and a bottom (patient-facing) layer of silver chloride. In another embodiment, both top and bottom layers of electrode traces 311, 312 may be made of silver chloride. In one embodiment, the top and bottom layers may be applied to the middle layer in the form of silver ink and silver chloride ink, respectively. In an alternative embodiment, each electrode trace may include only two layers, such as a top layer of silver and a bottom layer of silver chloride. In various embodiments, the material of a bottom layer of each electrode trace 311, 312, such as AgCl, may be selected to match the chemistry of the hydrogel electrodes 350 and create a half-cell with the body of the subject.

The thickness of the electrode traces 311, 312 may be selected to optimize any of a number of desirable properties. For example, in some embodiments, at least one of the layers of electrode traces 311, 312 can be of a sufficient thickness to minimize or slow depletion of the material from an anode/cathode effect over time. Additionally, the thickness may be selected for a desired flexibility, durability and/or signal transmission quality.

Figure 3E:
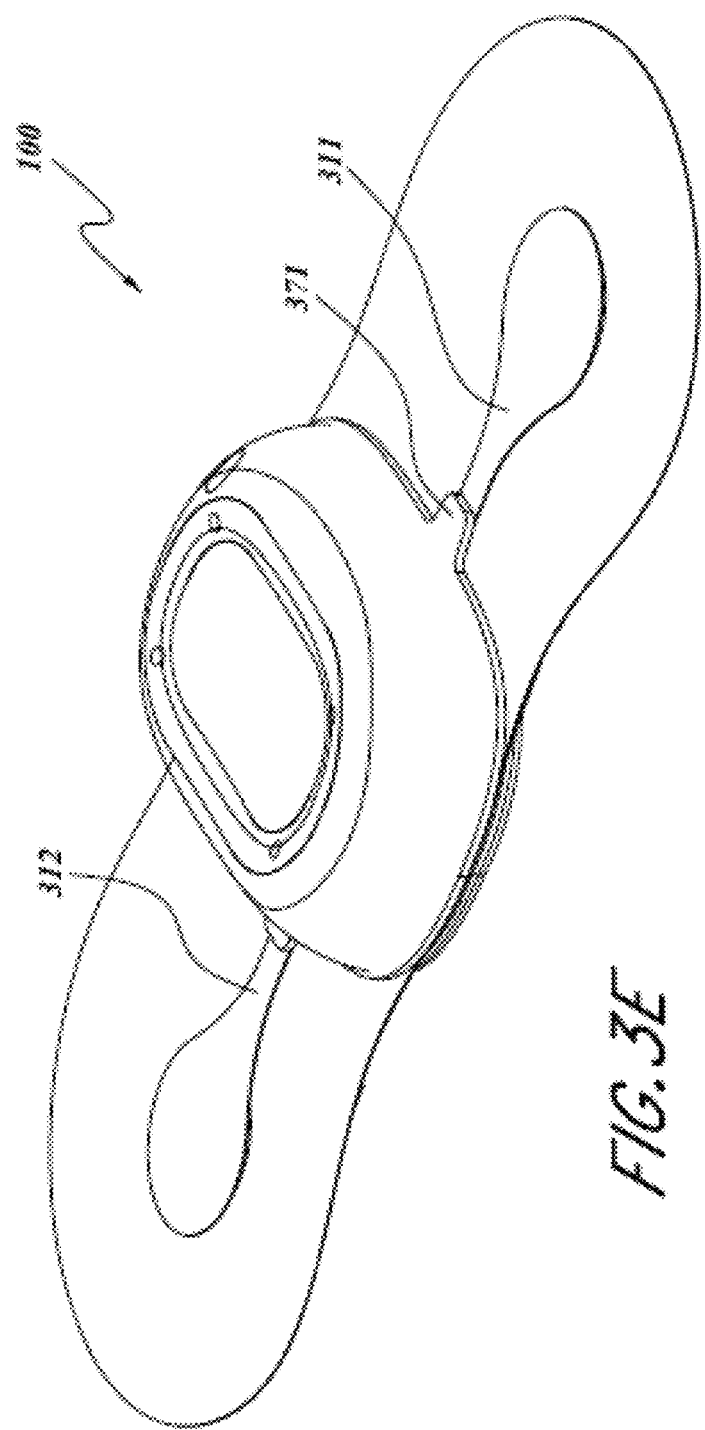

As mentioned above, in some embodiments, top gasket 370 and bottom gasket 360 may be attached upper substrate 300 and lower substrate 330 of flexible body 110. Gaskets 360, 370 may be made of any suitable material, such as urethane, which provides a water tight seal between the upper housing member 140 and lower housing member 145 of housing 115. In one embodiment, top gasket 370 and/or bottom gasket 360 may include an adhesive surface. FIG. 3E depicts yet another embodiment where top gasket 370 includes tabs 371 that protrude away from the profile of top housing member 140 while still being adhered to upper substrate 300. The tabs 371 cover a portion of electrode traces 311, 312 and provide a strain relief for the traces at the point of highest stress where the flexible body meets the housing.

FIGS. 4A-4E depict embodiments of adhesive layers 340, which can be included as adhesive layers in the embodiments of FIGS. 1-3 and below in FIGS. 5A-8D. Such adhesive layers may be incorporated into any of the physiological monitoring device embodiments described herein this section or elsewhere in the specification. In certain embodiments, the adhesive layer 340 may be configured to optimize (e.g., maximize) transpiration of moisture from the surface of the patient's skin beneath a physiological monitoring device such as depicted in FIGS. 1A-B, 3A-3E, and 5A-8D, through the wings of said devices such as described above as 130, 131. Promoting transpiration of moisture through the physiological monitoring device 100 (as shown in FIG. 3E and elsewhere) may improve adhesion of the device 100 to the patient's skin by preventing, reducing, and/or inhibiting the collection or pooling of moisture between the patient's skin and the bottom of the adhesive layer 340. Collection of moisture between the patient's skin and the bottom of the adhesive layer 340 may prevent, inhibit, and/or interfere with the adhesion of the adhesive layer 340 to the patient's skin, especially over long durations. For instance, the presence of excessive moisture may cause, promote, and/or accelerate the peeling of the edges of the adhesive layer 340 away from the patient's skin. Accordingly, longer term adhesion may be achieved by promoting the transpiration of moisture through the device so that it may be released (e.g., evaporate) into the atmosphere. The management of moisture may be particularly advantageous for when the patient sweats, such as during exercise or during a hot shower.

In particular embodiments, the adhesive layer 340 may generally comprise a top surface adhered to a bottom surface of the bottom substrate layer 330 (such as shown in FIG. 3B and elsewhere) or another support layer and a bottom surface configured to be adhered to the patient's skin. The top surface may generally overlap the bottom surface, and/or the top and bottom surfaces of the adhesive layer 340 may define an adhesion area or surface area that extends in a horizontal plane to a peripheral edge of the adhesive layer 340. The adhesive layer 340 may have a vertical thickness extending from the bottom surface to the top surface. The thickness may be relatively uniform across the adhesion area. In some embodiments, the adhesive layer 340 may comprise a plurality of channels 341 connecting the bottom surface of the adhesion layer 340 to the top surface and/or the peripheral edge of the adhesive layer 340. The channels 341 may be formed as hollow voids within the adhesive layer 340. The cumulative surface area of the channels 341 where the channels 341 interface the skin of the subject may, in some embodiments, be proportional to the rate of moisture transpiration. Larger cumulative surface areas of void regions may increase the rate of transpiration but may reduce the amount of adhesive force between the skin of the subject and the adhesive layer 340. The adhesive layer 340 may or may not comprise barriers separating the void volumes from the adhesive matrix material (e.g., the hydrocolloid).

In some embodiments, the inclusion of channels 341 within the adhesive layer 340 may generally make the adhesive layer 340 more conformable to the surface of the subject (e.g., the skin). For instance the adhesive layer 340 may better absorb bending strain due to the presence of the plurality of channels 341, which may promote or improve adhesion of the physiological monitoring devices (such as described herein this section or throughout the specification) to the subject, particularly on a non-flat surface and/or on a portion of the body expected to experience dynamic conformational changes. The plurality of channels 341 can be arranged to promote customized movement or strain of the flexible body 110 (as shown in FIG. 3B and elsewhere) in response to particular muscle stretches and/or contractions.

Figure 4A:
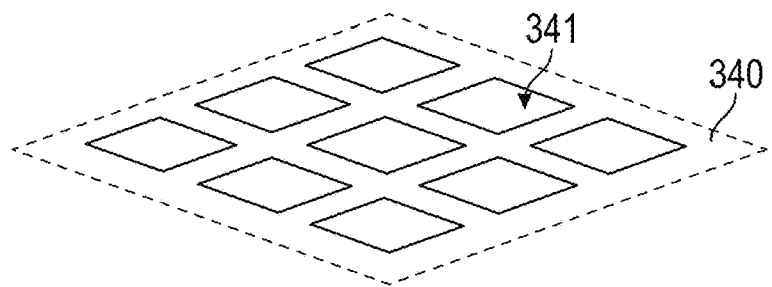
FIGS. 4A-4E schematically depict examples of adhesive layers comprising different arrangements of channels.

FIGS. 4A-4E further display examples of adhesive layers 340 comprising different arrangements of channels 341. The plurality of channels 341 may be generally linear and/or non-linear. In some embodiments, the plurality of channels 341 may comprise vertical channels 341 that extend from the top surface to the bottom surface of the adhesive layer 340. FIG. 4A schematically illustrates a top view of a portion of adhesive layer comprising vertical channels 341. The vertical channels 341 may extend in a direction substantially normal to the top surface and/or the bottom surface of the adhesive layer 340. The cross-sections of the vertical channels 341 may have generally diamond shapes, as shown in FIG. 4A, circular shapes (e.g., cylindrical channels), oval shapes, rectangular shapes, trapezoidal shapes, pentagonal shapes, hexagonal shapes, other polygonal shapes, or any other suitable shape. In some embodiments, particularly in which vertical channels 341 are closely spaced, the remaining adhesive layer 340 may take the form of a lattice structure, as shown in FIG. 4A. The shape of the vertical channels 341 may affect the mechanical properties of the latticed adhesive layer 340. Diamond-shaped channels 341 may allow preferential expansion and/or compression in an accordion-like fashion. For example, the adhesive layer 340 illustrated in FIG. 4A may provide less resistance to tension and/or compression along axes parallel to those that bisect the angular corners of the diamond-shaped vertical channels 341 than along axes which are parallel to the latticed struts formed from the adhesive layer 340. Also, the adhesive layer 340 may provide less resistance to tension and/or compression along axes parallel to those that bisect larger angles of the vertical channels 341 than axes parallel to those that bisect smaller angles of the vertical channels.

Figure 4B:
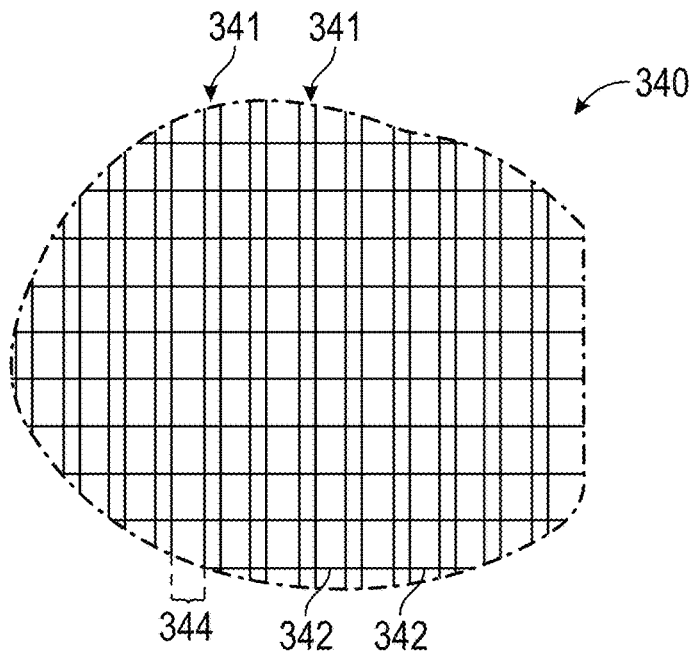

In some embodiments, the plurality of channels 341 may comprise horizontal rows or columns of channels 341 that connect the top and bottom surfaces of the adhesive layer 340. The rows or columns may be arranged in a relatively uniformly spaced manner. The rows or columns may extend from and/or to the periphery of the adhesive layer 340. The rows or columns may extend across the adhesive layer to another point on the periphery of the adhesive layer 340 dividing the adhesive layer into thin strips 342. FIG. 4B schematically illustrates an adhesive layer 340 comprising column channels 341. In some implementations, an adhesive layer 340 comprising either rows or columns of channels 341 may be configured to be oriented on the subject such that the rows or columns extend parallel to the height of the subject (e.g., aligned with a direction from the subject's head to the subject's feet). Aligning the channels 341 entirely or even partially with the height of the subject may advantageously promote gravity-facilitated drainage of moisture from under the adhesive layer 340 when the subject (e.g., a human subject) is in an upright (e.g., standing) position. The direction of the channel 341 can be defined by orthogonal components and the effect of gravity may depend on the magnitude of the component aligned with the height. Aligning the channels 341 in a first direction (e.g., aligned with the height of the subject) may partially relieve tensile and/or compressive forces along a second direction orthogonal to the first direction (e.g., aligned transverse to the height of the subject). In some embodiments, the channels 341 may be arranged such that the channels 341 are aligned transverse to a direction expected to undergo the most significant strain (e.g., the channels 341 may be aligned transverse to a direction of extension/contraction of a muscle over which the physiological monitoring device 100 is positioned). The channels 341 may absorb some of the strain improving the longevity of the adhesive layer 340. The presence of and, particularly, the arrangement of the channels 341 may mechanically improve the resistance of the adhesive layer 340 to delamination from the skin of the subject, particularly along certain directions, and may promote longer term adhesion of the physiological monitoring device 100 (such as shown in FIG. 3E and elsewhere).

Figure 4C:
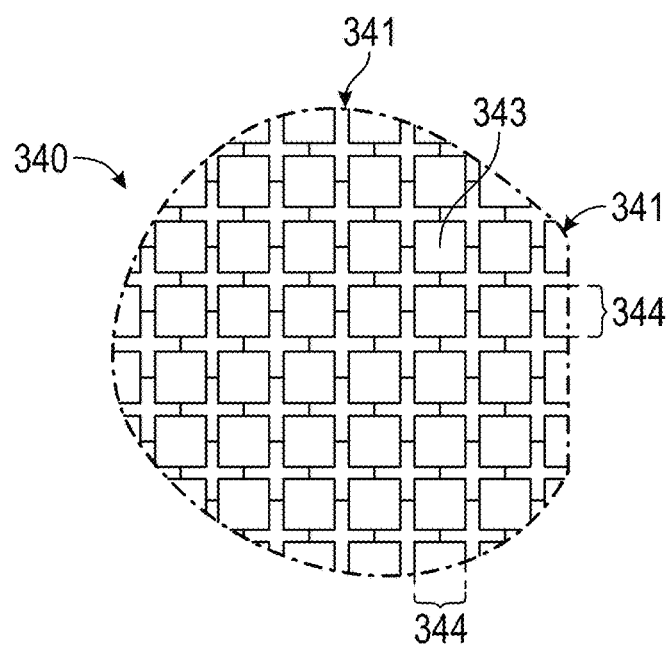
Figure 4D:
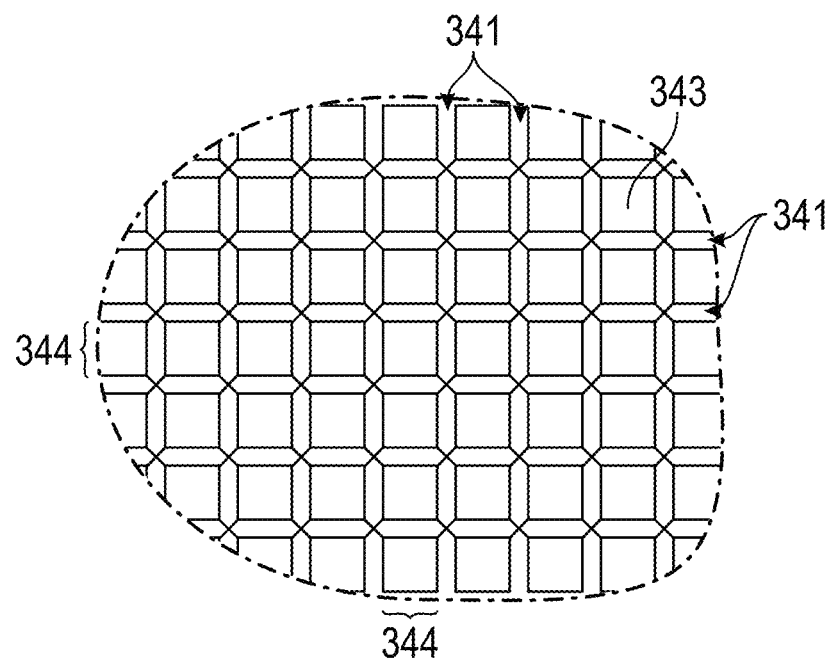

In some embodiments, the plurality of channels 341 may comprise both rows and columns. The rows and columns may be arranged in a uniformly spaced manner (e.g., substantially perpendicular to each other) to form a lattice network which divides the adhesive layer 340 into small islands 343 of adhesive material. The islands 343 may have rectangular configurations (e.g., a perpendicular lattice network), diamond configurations, trapezoidal configurations, pentagonal configurations, hexagonal configurations, other polygonal configurations, etc. FIGS. 4C and 4D schematically illustrate examples of an adhesive layer 340 comprising lattice networks of channels 341. In various embodiments, there may be a maximum separation distance 344 between the channels 341. In other words, each channel 341 may be separated from another channel 341 or from a peripheral edge of the adhesive layer 340 at any point along the length of the channel 341 by no more than the maximum separation distance 344. In some embodiments, the maximum separation distance 344 may be approximately 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 20 mm, 25 mm, 30 mm, or greater than 30 mm. The actual separation distance may be equal to the maximum separation distance 344. In some preferred embodiments, the separation distance may be approximately 8 mm. The close spacing of the channels 341 (e.g., within the maximum separation distance 344) may more efficiently promote the transpiration of moisture from beneath the adhesive layer 340 and/or may prevent, inhibit, or decrease the amount of peeling of the adhesive layer 340 from the skin of the subject.

In some embodiments, the strips 342 and/or islands 343 of the adhesive material may be interconnected by a network of thin webbing 345. The webbing 345 may comprise thin, flexible strands of material coupling the strips 342 and/or islands 343 together. In some embodiments, the webbing 345 may comprise nylon, cotton, polyester, and/or another suitable material. In some embodiments, the webbing 345 may extend through the strips 342 and/or islands 343, as schematically illustrated in FIG. 4B. For instance, in some embodiments, the strips 342 and/or islands 343 may be formed around the strands of the webbing 345 such that the strands extend through an interior volume of the strip 342 and/or island 343. In some embodiments, the network of webbing 345 may comprise a generally perpendicular network of columns and rows of strands as shown in FIGS. 4C and 4D. In some embodiments, the network of webbing 345 may be oriented in substantially the same manner as the rows and columns of channels 341 as shown in FIG. 4C, where rows of strands intersperse rows of channels 341 and columns of strands intersperse columns of channels 341. In some embodiments, the network of webbing 345 may be oriented in a different manner such as shown in FIG. 4D, where the rows and columns of webbing 345 strands are approximately 45 degrees offset from the rows and columns of channels 341. The webbing 345 may extend diagonally through the islands 343 and strands of webbing 345 may cross each other within the channels 341.

Figure 4E:
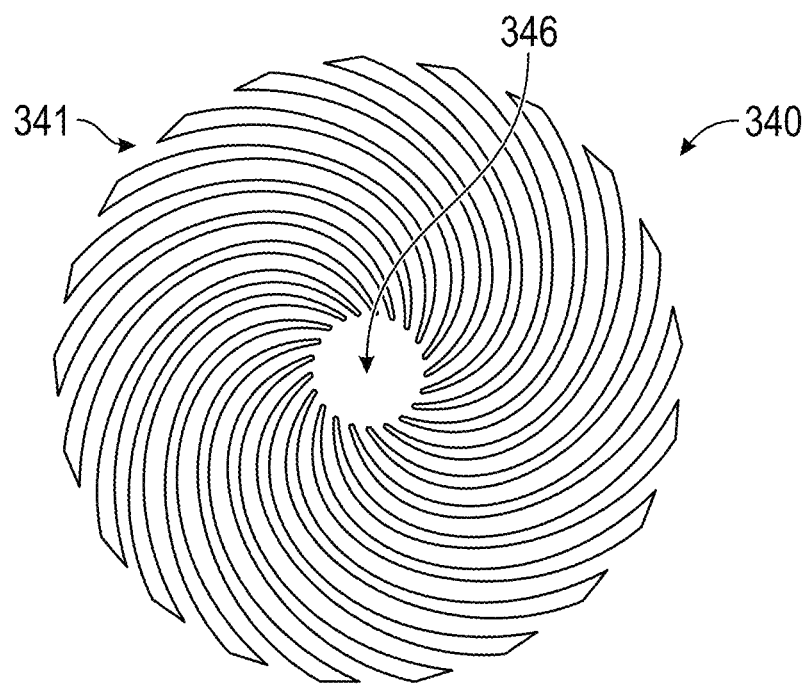

In some embodiments, the channels 341 may be arranged in a radial pattern (e.g., a linear spoke pattern). In some embodiments, the channels 341 may be non-linear (e.g., a coaxial arrangement of ring-shaped channels 341). For example, the channels 341 may be radially arranged in the horizontal plane in a spiraling fashion, as schematically illustrated in FIG. 4E. The channels 341 may meet at a central point 346. In some embodiments, the central point 346 may be a solid piece of the adhesive layer 340. In some embodiments, the central point 346 may be a void space, as shown in FIG. 4E. The void space may be substantially circular. In some embodiments, the void space may comprise at least about 5%, 10%, 15%, 20%, 25%, or 30% of the total surface area of the adhesive layer 340.

In some embodiments, the strips 342 and/or islands 343 of adhesive material may be affixed to a thin backing layer. For instance, in some embodiments the strips 342 and/or islands 343 may be formed directly on a bottom surface of the bottom substrate layer 330. In some embodiments, the adhesive layer 340 may be formed on a removable backing layer which is removed from the adhesive layer 340 after it is transferred to the bottom substrate layer 330 of the flexible body 110. In some embodiments, the adhesive layer 340 may be formed free of any backing layer (e.g., formed around the webbing 345). In some embodiments, the channels 341 may be formed during fabrication of the adhesive layer 340. For instance, the adhesive matrix of the adhesive layer 340 may be formed around a die imparting the shape of the channels 341. In some embodiments, the channels 341 may be formed after fabrication of the adhesive layer 340. For instance, after fabrication the adhesive layer 340 may be perforated or vertical channels 341 may be punched through the adhesive layer 340. In some embodiments, tubes (e.g., capillary tubes) may be inserted into and through the adhesive layer 340 to form vertical channels 341. In some embodiments, horizontal strips of adhesive layer may be removed (e.g., by cutting) leaving behind strips 342 and/or islands 343 of the adhesive material. In some embodiments, the adhesive matrix of the adhesive layer 340 may be formed on a backing layer or substrate, which may optionally be removed from the adhesive layer 340 prior to adhering the adhesive layer 340 to the bottom substrate layer 330 (such as shown in FIG. 3B and elsewhere). In some embodiments, the adhesive layer 340 may be fabricated around strands of a network of woven or non-woven webbing 345 as described elsewhere herein. In instances where the adhesive layer is fabricated around strands of non-woven webbing, the channels may manifest as random voids (which may have any suitable shape, such as an ellipsoid) dispersed through the adhesive. Where the voids and/or pockets connect, channels are formed but even where they do not connect directly, their presence may enable improvement of air flow through the adhesive. With a less solid adhesive layer, this approach may improve conformability to the skin. In some embodiments, a network of webbing 345 may be coupled to the adhesive layer 340 (e.g., pressed into) after the adhesive layer has been fabricated. A network of webbing 345 may be useful for helping to remove the adhesive layer 340 from a die or backing layer and/or for positioning the adhesive layer 340 over the bottom substrate layer 330 of the flexible body 110. In certain embodiments, the adhesive layer 340 may include channels for transpiration. Such channels may or may not have continuous walls. In certain embodiments, the channels may be vertical, orthogonal, or be oriented at any suitable angle.

In some embodiments, the adhesive layer 340 may comprise moisture wicking materials (e.g., water adsorbing materials) and/or may be coupled to a layer of moisture wicking materials. The moisture wicking materials may comprise a matrix of moisture wicking fibers. The moisture wicking materials may comprise wool, nylon, polyethylene terephthalate (PET), polytetrafluoroethylene (PTFE), expanded PTFE (ePTFE), thermoplastic elastomers (TPE), and/or any other suitable water-absorbent material. In some embodiments, the moisture wicking materials may be hydrophobic and/or hydrophilic, such that the core can retain the water, move it outward/upward and the outer sheath of the fiber can insulate the surrounding adhesive from moisture. The moisture wicking material may be formed as a layer above the top surface of the adhesive layer 340 (e.g., between the adhesive layer 340 and the bottom substrate layer 330) or used as capillary tubes. The moisture wicking material may be used to partially or entirely fill or line one or more of the plurality of channels 341. In some implementations, the inclusion of moisture wicking materials may facilitate drawing moisture from the surface of the subject through the channels 341 and/or into the adhesive layer 340 and/or upper substrate layers, such as through a moisture vapor permeable layer. In certain embodiments, the moisture may be moved out to the uppermost surface and optionally evaporated through a moisture vapor permeable layer, and/or to the outer edges of the adhesive for evaporation. The inclusion of moisture wicking materials may allow for the storage of moisture within the adhesive layer 340 away from the interface between the bottom of the adhesive layer 340 and the skin of the subject where the moisture is likely to promote delamination of the adhesive layer 340. The storage of moisture within the adhesive layer 340 or other layers of the physiological monitoring device 100 may be advantageous when the moisture from the surface of the subject cannot be transpired through the device 100 as quickly as it is generated, preventing or inhibiting the buildup of moisture between the bottom surface of the adhesive layer 340 and the skin. In some embodiments the wicking and/or fibers present in the materials may be oriented such that moisture is pulled outward radially from the adhesive. At outer areas of the adhesive or where perforations are present, a moisture sink may be created which maximizes surface area of those fibers, allowing for evaporation of the moisture that accumulates from within.

The peripheral edge of the adhesive layer 340 may promote undesired adhesion of materials to the periphery of the adhesive layer 340. Particularly in examples comprising a border 133, portions of the flexible body 110 may become adhered to the peripheral edge of the adhesive layer 340. For instance, the bottom surface of the top substrate layer 300 forming the border 133 may become adhered to the peripheral edge of the adhesive layer 340. Adhesion of substrate layers of the flexible body 110 to the peripheral edge of the adhesive layer 340 may deform the flexible body 110 from its intended configuration and/or may interfere with the proper mechanics and distribution of stress throughout the flexible body 110 which could inhibit or decrease the duration of long-term adhesion between the device 100 and the skin. Additionally or alternatively, dirt, debris, or adjacent portions of skin may become adhered to the peripheral edge of the adhesive layer 340 which may also interfere with long-term adhesion. Adhesion of foreign material to the peripheral edge of the adhesive layer 340 may promote or lead to loss of adhesion of material between the skin of the subject and the bottom surface of the adhesive layer 340. Delamination of the adhesive layer 340 may tend to initiate at the edge of the adhesive layer 340. If the edge begins to delaminate from the skin, the border 133 or other materials which are adhered to the peripheral edge may become tucked under the adhesive layer 340 between the bottom surface and the skin. For instance, the border 133 may begin to fold under the adhesive layer 340. The wedging of materials between the bottom surface of the adhesive layer 340 and the skin of the subject may apply a stress to the adhesive layer 340 and/or deform the adhesive layer 340 which may lead to further delamination, such that peeling may begin to nucleate from the peripheral edge. Adhesion between the bottom surface of the adhesive layer 340 and the external material may continue to draw the material in under the adhesive layer 340, creating an "inchworm effect," particularly where the material experiences a stronger adhesion to the adhesive layer 340 than the skin of the subject experiences relative to the adhesive layer 340.

In some embodiments, adhesion to the peripheral edge of the adhesive layer 340 may be prevented or inhibited by lining the peripheral edge of the adhesive layer 340 with a non-adhesive material in the form of a blocking liner. In certain examples, no adhesive may be applied to the periphery such that a blocking liner may not be used to prevent or inhibit adhesion to the peripheral edge. Where no adhesive is used at the periphery, adhesive may be printed to a carrier film, but not to the periphery. In some embodiments, the non-adhesive material may comprise a silicone (e.g., polydimethylsiloxane (PDMS)) and/or any other suitable material. The non-adhesive lining may outline the entire periphery of the adhesive layer 340 or may outline continuous and/or discontinuous portions of the periphery. The non-adhesive lining may comprise an annular (e.g., ring-shaped) configuration. An inner diameter of the non-adhesive lining may be generally equal to an outer diameter of the adhesive layer 340. The non-adhesive liner may be generally flexible or elastic such that it may conform to the peripheral edge of the adhesive layer 340 and/or may experience dynamic strain as the subject moves without delaminating from the adhesive layer 340. The non-adhesive lining may extend from the top of the peripheral edge to the bottom of the peripheral edge or may extend along a portion of the thickness (e.g., a top portion, a bottom portion, and/or an intermediate portion). The non-adhesive lining may comprise a width extending from the peripheral edge of the adhesive layer 340 to an outer edge of the lining. The width may be no greater than approximately 0.5 mm, 1 mm, 2 mm, 3 mm, 4 mm, or 5 mm. In some embodiments, the inner diameter of the non-adhesive liner may comprise an adhesive surface, which may facilitate the adhesion of the non-adhesive liner to the peripheral edge of the adhesive layer 340. In some embodiments, the bottom surface of the non-adhesive lining may be non-adhesive creating a buffer between the bottom surface of the adhesive layer 340 and the outer diameter of the non-adhesive lining. In some embodiments, the bottom surface of the non-adhesive lining may be adhesive and configured to adhere to the skin of the subject. The non-adhesive liner may prevent or inhibit the adhesion of any portion of the flexible body 110, any other materials, or adjacent portions of skin form adhering to the peripheral edge of the adhesive layer 340 and/or may prevent or inhibit materials from inserting themselves between the bottom surface of the adhesive layer 340 and the skin of the subject. The non-adhesive liner may promote or increase the duration of long-term adhesion of the adhesive layer 340 to the skin of the subject.

In some embodiments, a peripheral area of the adhesive layer 340 may comprise a tapered thickness. The thickness of the adhesive layer 340 may decrease from a central location radially outward toward the peripheral edge of the adhesive layer 340, and/or vice versa. In some embodiments, the central location may be a generally central point of the adhesive layer 340 such that the width is variable across an entire radius of the adhesive layer 340. In some embodiments, a central region of the adhesive layer 340 may comprise a uniform thickness and a peripheral annular region may comprise a tapered thickness, and/or vice versa. In some embodiments, particularly in embodiments in which the adhesive layer 340 comprises a generally circular surface area, the thickness of the adhesive layer 340 may be uniform in a circumferential direction or at points positioned equal distances from the peripheral edge. In some embodiments, at least the outer most 1 mm, 2 mm, 3 mm, 4 mm, 5 mm, 6 mm, 7 mm, 8 mm, 9 mm, or 10 mm of the adhesive layer 340 may comprise a tapering thickness. A more gradual taper may provide for more advantageous mechanics and distribute stresses through the adhesive layer 340 more uniformly. The thickness of the peripheral edge of the adhesive layer 340 may be no greater than approximately 5%, 10%, 15%, 20%, 25%, 30%, 40%, or 50% of a maximal thickness of the adhesive layer 340 (e.g., at a central portion). In some embodiments, the thickness may taper down to a generally pointed edge of negligible thickness. The reduced thickness of the peripheral edge may prevent or prohibit adhesion of the flexible body 110, any other materials, or adjacent portions of skin form adhering to the peripheral edge of the adhesive layer 340 and/or may prevent or inhibit materials from inserting themselves between the bottom surface of the adhesive layer 340 and the skin of the subject. The tapered peripheral edge may promote or increase the duration of long-term adhesion of the adhesive layer 340 to the skin of the subject.

Figure 5A:
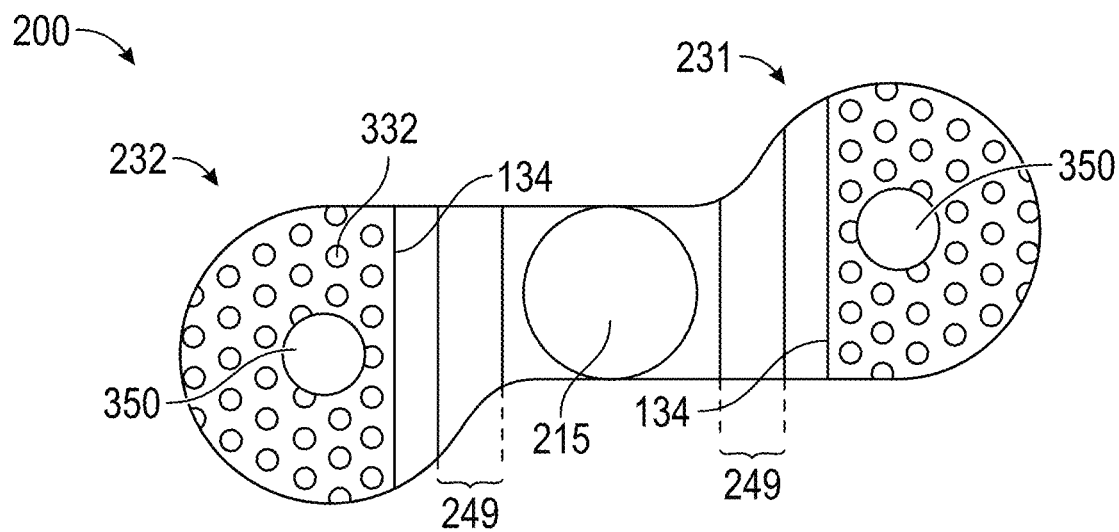
FIGS. 5A-5H schematically illustrate another embodiment of a physiological monitoring device.

FIGS. 5A-5H schematically illustrate another embodiment of a physiological monitoring device 200, similar to the physiological monitoring devices depicted in FIGS. 1A-1B and in additional figures later in the specification, such as FIGS. 6A-6H. FIG. 5A schematically depicts a bottom view the physiological monitoring device 200 including the horizontal disposition of various constituent layers. The physiological monitoring device 200 may comprise wings 232, 231 which are each asymmetrical or symmetrical about a longitudinal axis extending between the electrodes 350. One of the wings 231, 232 may comprise a body which is disproportionately distributed above the longitudinal axis and the other wing 231 may comprise a body which is disproportionately distributed below the longitudinal axis. The wings 231, 232 may make the flexible body asymmetric about a transverse axis, perpendicular to the longitudinal axis and extending through the housing 215, also including patient trigger 216. In certain embodiments, the patient trigger may encompass about: 10 to 30% of the total top area, such as about 20% of the top area or about 23% such as about 22.8% of the total top area. In certain embodiments, the patient trigger may encompass more than about 20%, more than about 30%, more than about 40%, more than about 50%, or more than about 75%. In certain examples, the patient trigger may encompass the entire top surface of the housing. The wings 231, 232 may comprise identical shapes which are reversed or flipped about both the longitudinal axis and the transverse axis as shown in FIG. 5A. The configuration of the flexible body may be particularly suitable for positioning the electrodes in a diagonal arrangement with respect to the height of a subject (e.g., FIGS. 9B-9E).

In various embodiments, such as those shown in FIGS. 3A-3E, FIGS. 5A-5H, and any other embodiments described herein, the one or more of the substrate or support layers supporting the adhesive layer 340 and the electrodes 350 may comprise perforations or apertures 332 disposed through the thickness of one or more layers. The apertures 332 may provide breathability through one or more layers and may promote transpiration of moisture from below the adhesive layer 340 through the layer or layers comprising the apertures 332. The shape and/or arrangement of the apertures 332 may affect the mechanical properties of the latticed adhesive layer 340. The apertures 332 may provide a degree of compliance or conformability to a relatively rigid layer which provides structural support to the flexible body 110, 310. For instance, the apertures 332 may promote bendability of the thin layer. In some embodiments, the apertures 332 may be circular in shape as shown in FIG. 5A. In some embodiments, the apertures may be diamond-shaped similar to the vertical channels 341 shown in FIG. 4. In embodiments, the apertures 332 may be rectangular, square, oval, trapezoidal, pentagonal, hexagonal, polygonal, or any other suitable shape as well. Like the vertical channels 341 in the adhesive layer 340, the apertures 332 may create a lattice structure within at least a region of the perforated layer, particularly where apertures 332 are positioned close together. The perforated layer may provide anisotropic resistance to tension and/or compression along various axes within the horizontal plane of the perforated layer in the same manner as described elsewhere herein with respect to the vertical channels 341.

In some embodiments, the wings 130, 131 may comprise structural reinforcement members (not shown) along peripheral edges of the wings 130, 131. The structural support members may comprise thin wire-like configurations. The structural reinforcement members may be disposed in or in between any layers of the wings 130, 131, such as the top substrate layer 300 or the bottom substrate layer 330. In some embodiments, the structural reinforcement members may be disposed in the borders 133 outside and around the adhesive layers 340. The structural reinforcement members may maintain or preserve the general shape (e.g., outer outline) of the wings 130, 131 even if the adhesive layer 340 begins to peel, deteriorate, and/or break down along the edges. The structural support members may comprise a relatively stiff metal or plastic. In some embodiments, the structural support member may comprise a shape memory material (e.g., nitinol). The shape memory properties of the shape memory structural support member may resist permanent deformation of the wings 130, 131 and may help prevent, for example, wrinkling of the wings and/or the border 133 tucking under the adhesive layer 340.

In some embodiments, the support layer may comprise at least two overlapping layers of material (e.g., top substrate layer 300 and bottom substrate layer 330). In some embodiments, the bottom most substrate layer (e.g., bottom substrate layer 330) and/or the top most substrate layer (e.g. top substrate layer 300) of the flexible body 110 may comprise more than one layer. The various layers may comprise polyethylene terephthalate (PET) and/or polyurethane (PU). In various embodiments, layers comprising PET may provide structural support to the flexible body. PET may be the most rigid or stiff material present throughout the layers of the flexible body 110. The layer providing structural support may also provide resistance to wrinkling of adjacent more wrinkle-prone (e.g., less rigid) layers. In various embodiments, layers comprising polyurethane may provide a conformable and/or breathable barrier to the flexible body 110, 310. Polyurethane may be the least rigid material or at least not the most rigid material present throughout the layers of the flexible body 110. The polyurethane may generally create a seal against water preventing water from entering through the ambient environment and penetrating between the adhesive layer 340 and the skin of the subject. The barrier layer may be particularly advantageous for allowing the subject to shower. Providing a shower-compatible physiological monitoring device may improve user compliance and/or promote or increase the duration of long-term wear. The polyurethane layer may be generally breathable allowing transpiration to occur through the polyurethane layer, particularly where the polyurethane layer is relatively thin. In some embodiments, a perforated PET layer may be positioned between the adhesive layer 340 and the polyurethane layer. In embodiments, a polyurethane layer may be positioned between the adhesive layer 340 and a perforated PET layer. In some embodiments, the bottom most substrate layer 330 may be integrated with the adhesive layers, for example in a spun polyurethane that enables the adhesive to be formed around the lattice or mesh structure provided by the substrate.

Figure 5B:
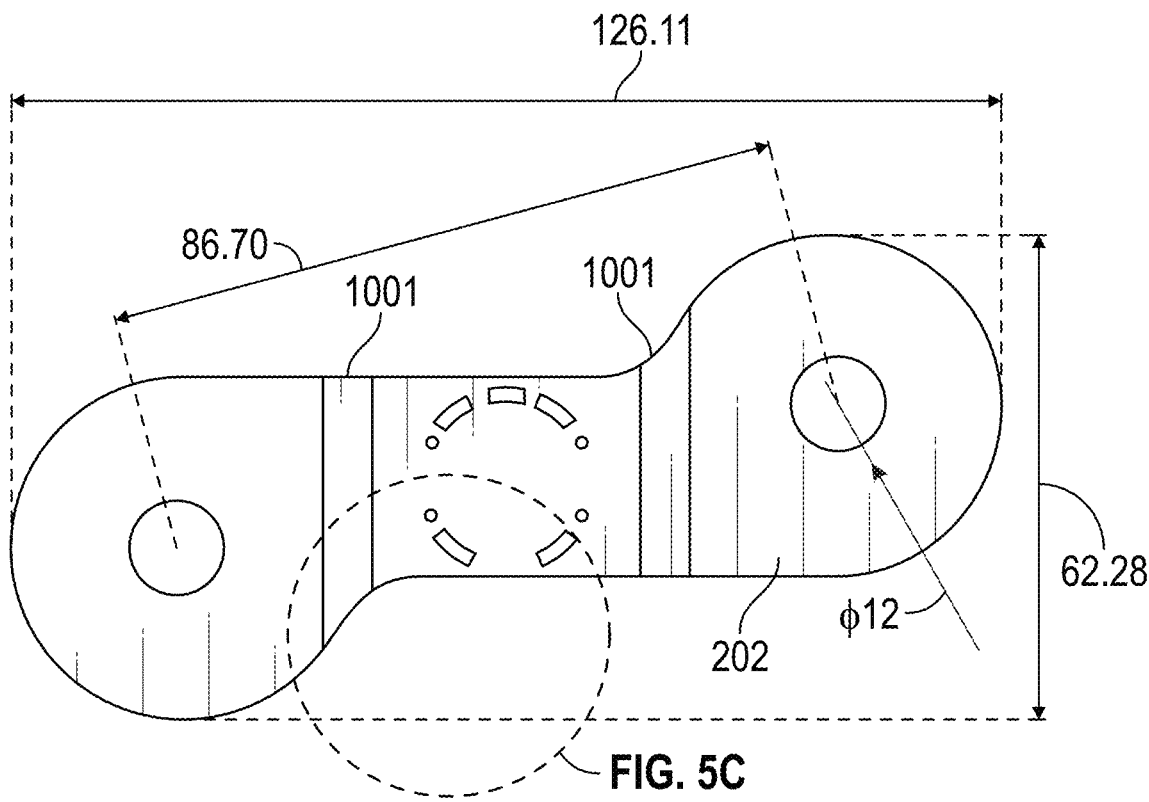
Figure 5C:
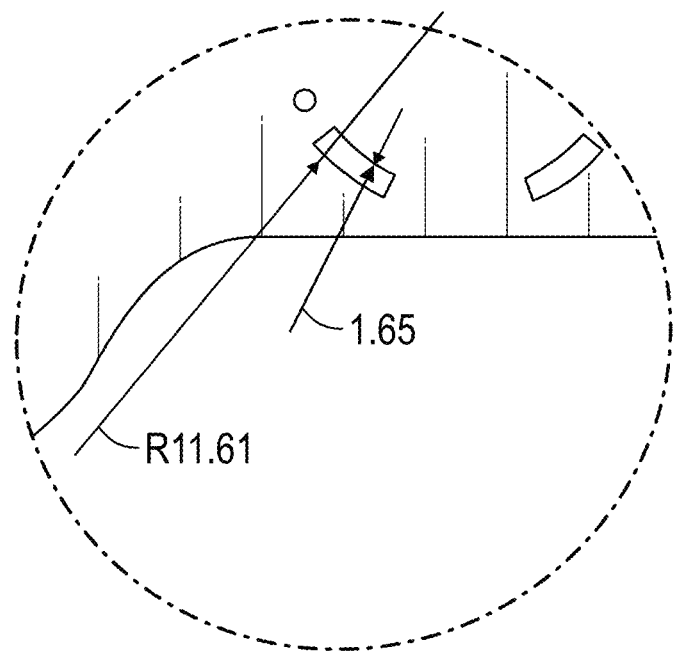
Figure 5D:
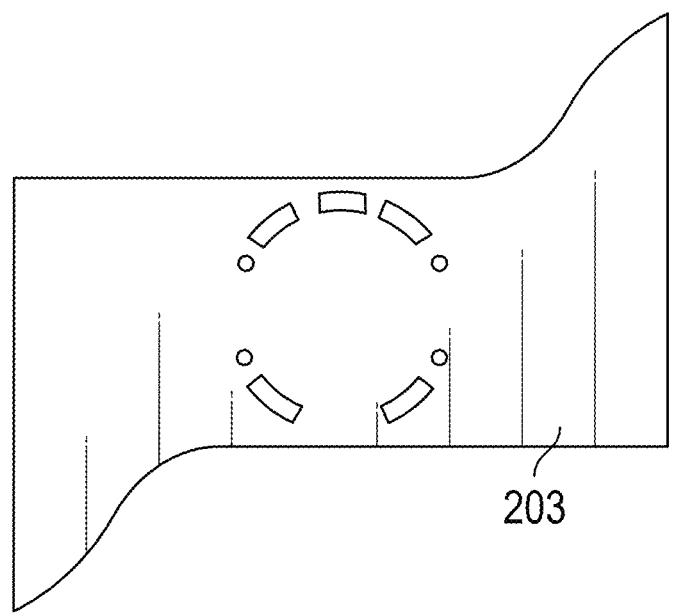
Figure 5E:
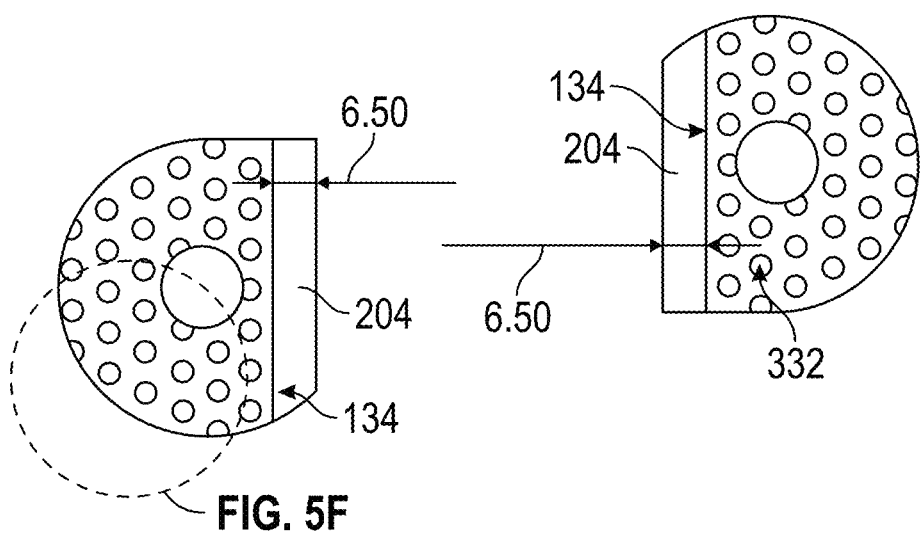
Figure 5F:
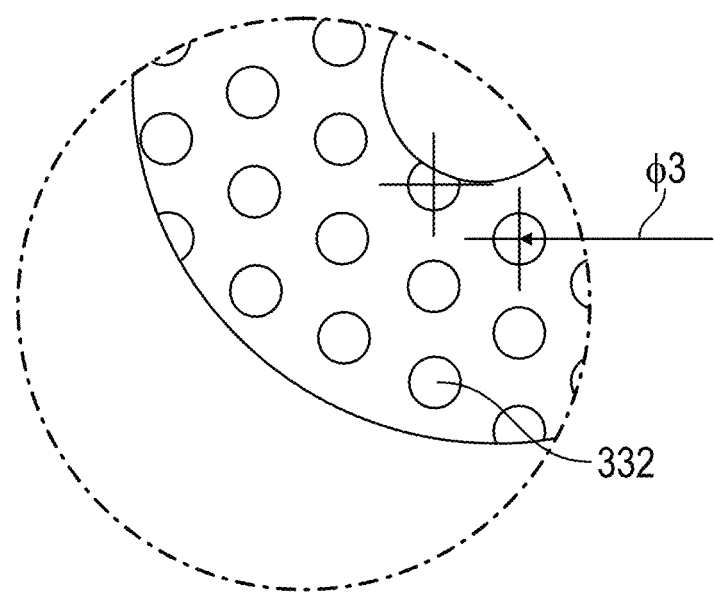
Figure 5G:
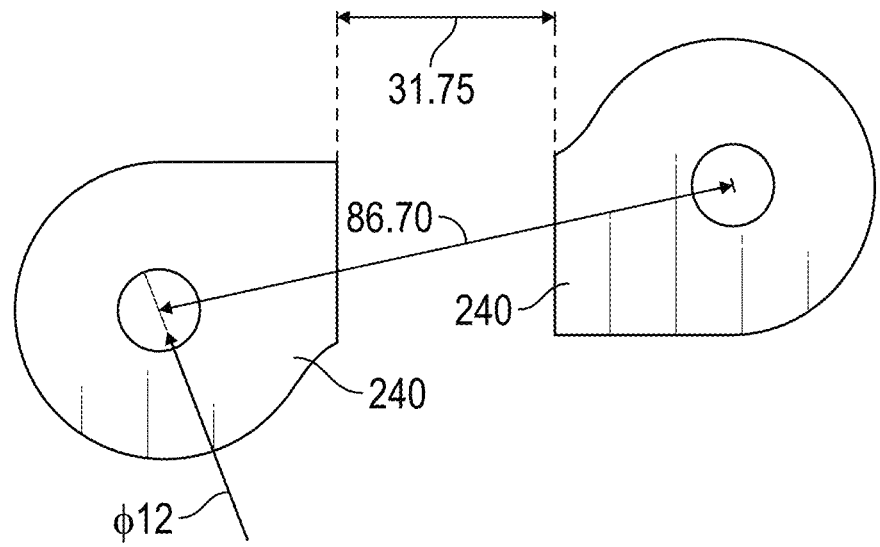
Figure 5H:
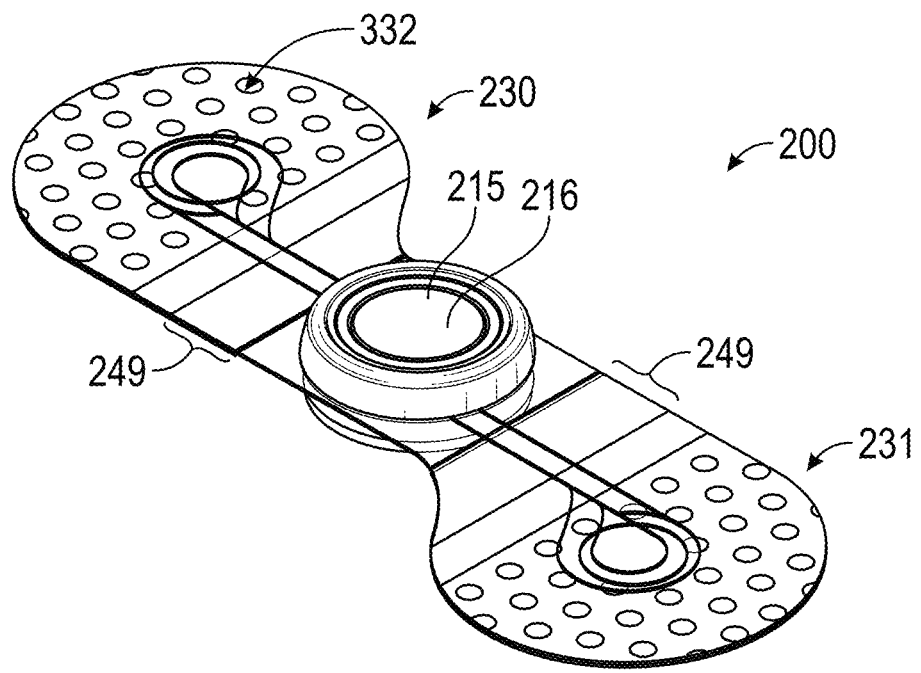

FIGS. 5B-5G schematically depict bottom views of various component layers of the embodiment shown in FIG. 5A and include examples of non-limiting dimensions (in mm) of the embodiment. All of the various layers forming the wings 231, 232 may comprise overlapping holes configured to receive electrodes 350 as described elsewhere herein. FIG. 5B illustrates a support layer 202 (e.g., polyurethane) forming the main structure of the flexible body. FIG. 5C illustrates a close-up of the inset A depicted in FIG. 5B. FIG. 5D illustrates an additional layer configured to form a "butterfly flap" 203 that supports the extension of adhesive 240, as shown in FIG. 5G, which may serve to limit opportunity for the adhesive to fold back and stick on itself during application. The butterfly flap layer 203 may extend between hinge lines 134. FIG. 5E illustrates perforated layers 204 (e.g., perforated PET layers) comprising apertures 332 for providing structural support to the wings 231, 232 while permitting moisture transmission. The perforated layers 204 may not extend continuously between the wings 231, 232 as shown. FIG. 5F illustrates a close-up view of the inset A depicted in FIG. 5E. FIG. 5G depicts two adhesive layers 240. As shown by a comparison of the various layers, the perforated layer 204 may not extend the entire length of the adhesive layer 240 along the longitudinal axis. The adhesive layer 240 may extend inward toward the housing 315 beyond the hinge line 134 forming flaps 249 which are supported on the top surface by butterfly flap layer 203 and adhered on the bottom surface to skin of the subject but which are not adhered to the overlying hinge portion of the support layer 202. In certain embodiments, this feature (as shown in FIG. 5B), where the hinge portion 1001 of support layer 202 is anchored to the subject's skin by both the proximal portion of adhesive 240 and the distal portion of adhesive 240, may distribute stresses applied upon the adhesive during wear and minimize peel forces that could more easily weaken the adhesive bond to skin. FIG. 5H depicts a perspective view of the physiological monitoring device 200.

In various embodiments, the adhesive layer (e.g., adhesive layer 340, 240, or any other adhesive layer described herein) may be replaceable. Replacing the adhesive layer 340 may prolong the duration of wear of the physiological monitoring device 100 as a fresh adhesive layer 340 may supplant an adhesive layer 340 which is beginning to or has lost a substantial ability to adhere the device 100 to the skin of the subject. To replace an adhesive layer 340, the top surface of the adhesive layer 340 may be separated from the bottom surface of the substrate layers of the flexible body 110 (e.g., the bottom surface of the bottom substrate layer 330). The physiological monitoring device 100 may be removed from the body of the subject and then the adhesive layer 340 separated from the flexible body 110. The adhesive layer 340 may be easiest to remove by peeling the adhesive layer 340 from the flexible body 110 beginning at an inside corner of the adhesive layer 340 (e.g., a corner closest to the housing 115. A specialized removal device may be provided for facilitating the removal of the adhesive layer 340. For instance, the removal device may comprise a thin flat blade configured to be inserted between the adhesive layer 340 and the flexible body 110. The removal device may comprise a handle extending from the blade. The handle may extend from the blade at an angle such that the blade may be positioned parallel to the flexible body which may be supported on a flat surface and the handle may be positioned and held above the flat surface. For example, the removal tool may be used to separate a corner of the adhesive layer 340 from the flexible body 110 and then the corner of the adhesive layer 340 may be used to pull or peel the remainder of the adhesive layer 340 from the flexible body 110. The removal tool or a separate removal tool may comprise a means for grasping the adhesive layer 340 after it has been partially separated from the substrate layers of the flexible body 110 such that the removal tool may be used to pull or peel the adhesive layer 340 from the substrate layers of the flexible body 110. The replacement adhesive layer 340 may be applied to the flexible body 110 in the same or similar manner as when the original adhesive layer 340 is applied to the substrate layers of the flexible body 110 during manufacture or assembly of the physiological monitoring device 100. For example, the adhesive layer 340 may be formed on a backing layer on the bottom surface of the adhesive layer 340, which can be removed after the top surface of the adhesive layer is adhered to the flexible body 110. In some embodiments, the replacement adhesive layer may be applied to the flexible body 110 through the use of a template or tool to enable easy and accurate positioning relative to the features on flexible body 110.

In some embodiments, the adhesive layer 340 may be comprised of multiple layers. In certain examples, if experiencing adhesion failure or for other suitable reasons, the user may remove the physiological monitoring device 100, and remove the bottom-most layer of 340 that was in direct contact with the skin. This removed layer may be the entire surface of 340, exposing a fresh adhesive layer of 340 below, or it might be an annular area of 340, exposing a fresh layer in only one portion of the adhesive, or some other smaller area that is less than the entire area. In certain embodiments, the layer of "used" adhesive may take the shape of a pattern distributed across the surface of adhesive 340, resulting in a distributed mix of fresh adhesive and "used" adhesive across its surface. Similar to replacement of the adhesive, refreshing the adhesive through removal of some or all of the most recent skin-contacting layer may have the effect of extending wear duration. The multiple layers of 340 in such an embodiment may be constructed through a combination of adhesive and release liner, where the release liner may be siliconized for releasability on the top surface but adhered more permanently on its bottom surface or vice-versa. The siliconization may be tuned to allow for intentional layer removal, without causing undue challenges in maintaining adhesion on the body. Additionally, in certain examples, adhesive layer removal may be enabled through the use of pull tabs built into the layers. Further, removal may also be enabled through a tool that adheres more strongly to the "used" adhesive than the release liner is adhered to the layer below it. In embodiments, the adhesive may be integrated within a lattice or mesh substrate, enabling separation from other layers of adhesive without losing integrity. In some embodiments, the physiological monitoring device 100 may have an annular ring of adhesive exposed without removal from the user's skin. An inner shape of adhesive on each wing may remain adhered while an annular ring was removed, exposing fresh adhesive and enabling extended wear. Adhesion failure often begins at the outermost edges of the adhesive, therefore this approach of refreshing only an annular ring on the outer layer may help extend wear duration while minimizing interruption of data collection and also increasing likelihood that the user continues to wear the device.

In some embodiments, a pull string (not shown) may be sandwiched between the adhesive layer 340 and the bottom substrate layer 330, embedded in the adhesive layer 340, or partially embedded in the adhesive layer 340 and partially sandwiched between the adhesive layer 340 and the bottom substrate layer 330. The pull string may have a free tail end at a proximal of the pull string extending beyond a peripheral edge of the adhesive layer 340. The pull string may extend across a surface area of the adhesive layer 340 according to a particular pattern. In some embodiments, the pull string may closely follow or trace the peripheral edge of the adhesive layer 340. In some embodiments, the pull string may closely follow an outer diameter of the electrode(s) 350. In some embodiments, the pull string may form a substantially closed circuit around a surface area of the adhesive layer 340. For instance, a distal tail end may be positioned in close proximity to the proximal free tail end. The distal tail end may freely extend beyond the peripheral edge of the adhesive layer 340 as does the proximal free tail end or it may be positioned within the surface area of the adhesive layer 340. The pull string may be configured to help remove the removable adhesive layer from substrate layer 330 or from another layer within adhesive layer 340. Pulling the free tail end of the pull string (e.g., pulling the free tail end of the pull string across a bottom surface of the adhesive layer 340) may cause the pull string to cut through the adhesive layer 340 and/or separate (e.g., lift off) the adhesive layer 340 or portions thereof from the substrate layers of the flexible body 110. In some embodiments, the pull string may remove a peripheral border area (e.g., an annular area) of the adhesive layer 340 from an inner central portion of the adhesive layer 340. The border area and/or other portions of the adhesive layer 340 may be lifted off the bottom substrate layer 330 or other layers within adhesive layer 340. Forming a division between different portions of the adhesive layer 340 may facilitate removal of the portions from the bottom substrate layer 330. The new severed edges created in the adhesive layer 340 by the pull string may provide starting locations for peeling the adhesive layer 340 from the bottom substrate layer 330. These edges may be easier to separate from the natural or original peripheral edges of the adhesive layer 340, particularly where the natural edges are flush with the edges of the bottom substrate layer 330. It may be easier to lift the severed edge of the adhesive layer off of an underlying surface such as the bottom substrate layer 330 than to separate two thin edges from each other at a peripheral edge of the flexible body 110. In some embodiments, pulling the pull string may at least partially lift the severed edge of the adhesive layer 340 off of the bottom surface of the bottom substrate layer 330 making subsequent peeling of the adhesive layer 340 easier. In some embodiments, the adhesive layer 340 may be naturally segmented or segmentable along paths not formed by a pull string. For instance, the adhesive layer 340 may be fabricated to be particularly frangible along a similar outline as the pull string, such as by disposing a path of perforations across the surface area of the adhesive layer 340. The pull string may be used in combination with other removal methods and/or tools disclosed elsewhere herein.

In some embodiments, the adhesive layer 340 may extend entirely to the edge or border of the substrate layers (e.g., including top substrate layer 300) such that the top surface of the adhesive layer 340 is adhered to the bottom surface of the border 133 as well as the bottom surface of the bottom substrate layer 330. In some embodiments, the flexible body 110 may not comprise a border 133 and the adhesive layer may extend to the edge of the bottom substrate layer 330. Embodiments that comprise replaceable adhesive layer 340 may be particularly suitable for adhesive layers 340 that extend to the outer edge or border of the flexible body 110.

Figure 8A:
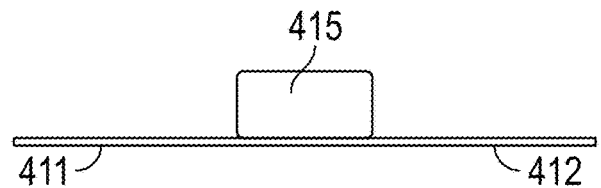
FIGS. 8A-8J schematically illustrate embodiments of a physiological monitoring device having a rigid body and traces coupled to the top surface of a flexible body.
Figure 8B:
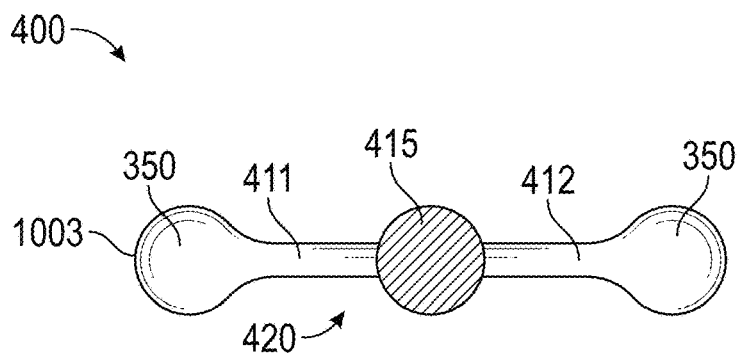
Figure 8C:
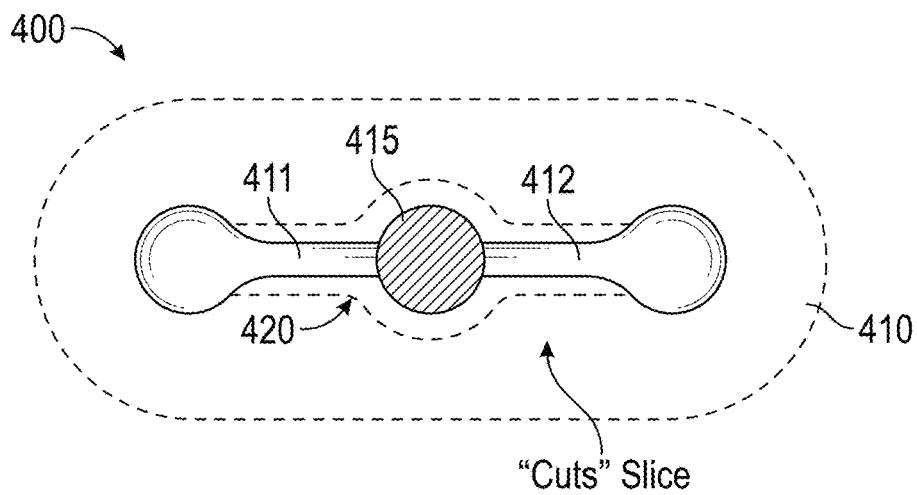
Figure 8D:
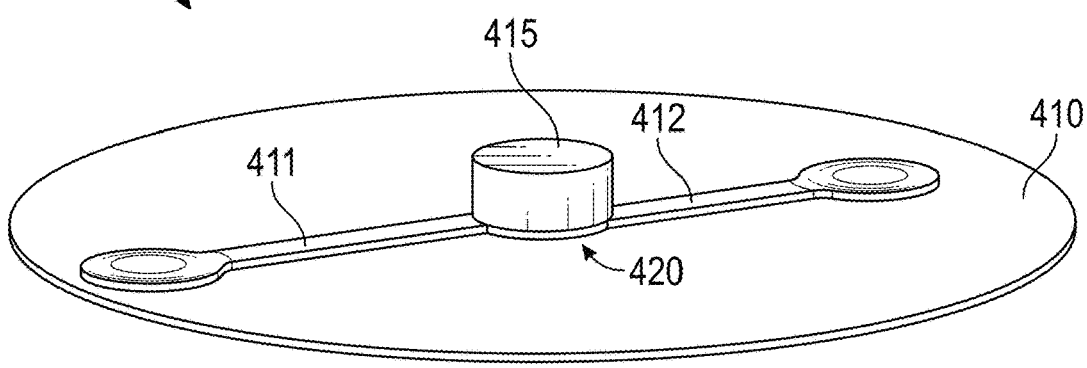

FIGS. 8A-8J illustrate embodiments of a physiological monitoring device 400. In some embodiments, the physiological monitoring device 400 may comprise a housing 415 that is connected to electrode traces 411, 412 as shown in FIGS. 8A and 8B. FIG. 8A shows a side view of the housing 415 and traces 411, 412 and FIG. 8B shows a top view of the housing 415 and the traces 411, 412. The traces 411, 412 may extend from the sides and/or from the bottom of the housing 415. The traces 411, 412 may be fixedly coupled to electrodes 350 at ends opposite the housing 415. To assemble the physiological monitoring device 400 the housing 415 and traces 411, 412 may be coupled (e.g., adhered) to a bottom surface of a flexible body 410, as shown in FIG. 8C. The flexible body 410 may be a single unit of material having a generally continuous flat surface. The outline or shape of the flexible body 410 may be the same as other flexible bodies described herein, maybe generally be round as shown in FIGS. 8C and 8D, or may be any other suitable shape. In some embodiments, the flexible body 410 may comprise apertures for receiving the electrodes 350. In some embodiments, the electrodes may be built into the flexible body 410 (e.g., the electrodes may be disposable). The flexible body 410 may comprise one or more constituent layers as described elsewhere herein, inclusive of adhesive and border layers. The constituent layers may extend continuously across the surface area of the flexible body 410 or may be proportioned across discrete sub-areas. The continuous flexible body 410 may be monolithic and continuous, covering the housing 415 and traces 411, 412. In certain embodiments, the flexible body 410 may be cut to allow relief for the housing 415, while covering traces 411 and 412. In embodiments, as shown in FIG. 8C, the continuous flexible body 410 may be cut along a path around a floating portion 420 or butterfly flap portion of the flexible body 410 which surrounds the rigid body and/or housing 415 and at least a portion of length of the traces 411, 412 extending from the rigid body and/or housing 415, but excluding the electrodes. The flexible body 410 may be provided in a pre-cut configuration prior to coupling the housing 415. In some embodiments, the flexible body 410 may comprise perforations or other frangible features which makes the floating portion 420 readily separable from the remainder of the flexible body 410. In some embodiments, the pre-cut areas of flexible body 410 may include a hinged portion that supports the trace as it lifts off the skin. The bottom surface of the floating portion 420 may be free of adhesive such that the floating portion 420 is free to lift off of the skin of the subject as shown in FIG. 8D and as described elsewhere herein. In particular embodiments, the bottom surface of the distal ends of traces 411, 412, prior to the hinge point, may be coated in adhesive to better secure the electrodes to the skin.

Figure 8E:
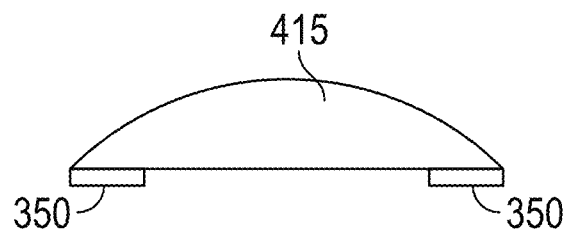
Figure 8F:
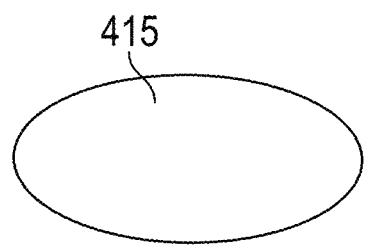
Figure 8G:
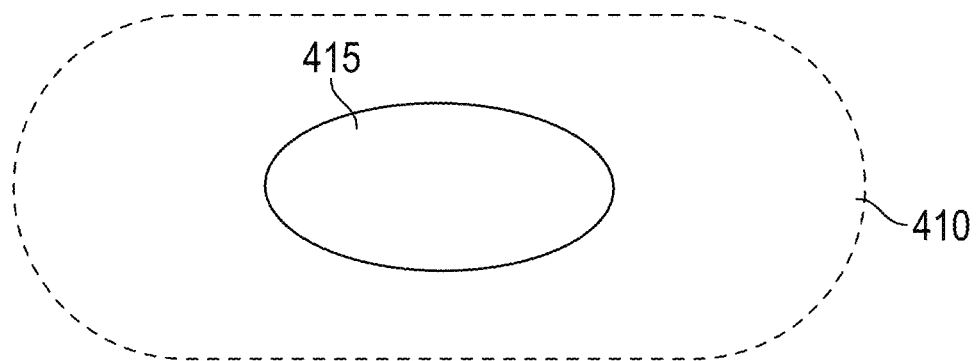
Figure 8H:
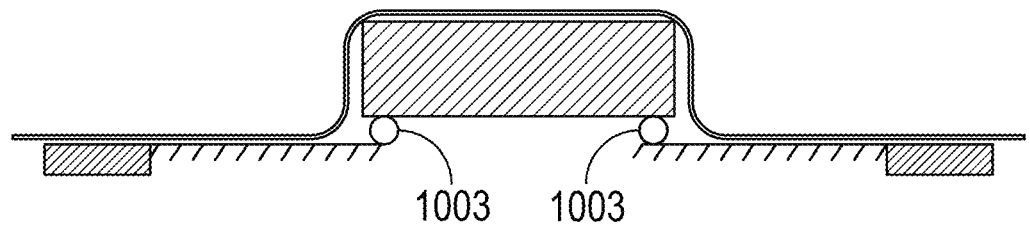
Figure 8I:
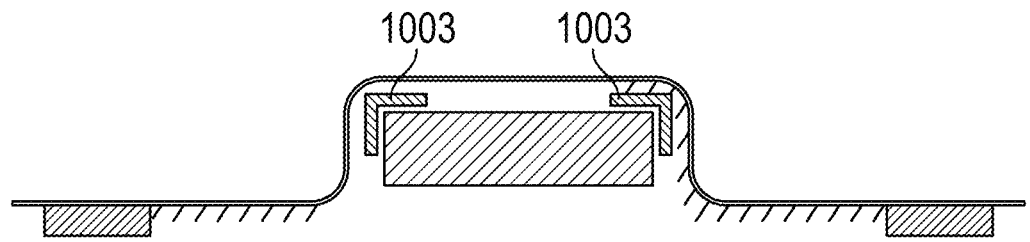
Figure 8J:
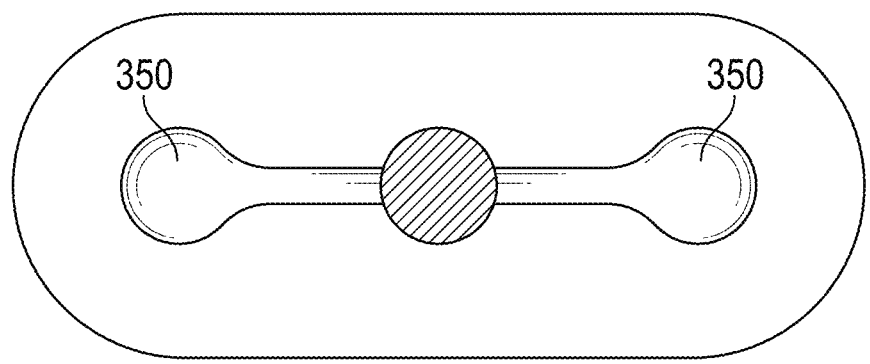

In some embodiments, a housing 415 may include sensing electrodes 350, as shown in FIGS. 8E (profile) and 8F (top view). A flexible adhesive body 410 may be placed over top of the housing 415, as shown in FIG. 8G. In some embodiments, the housing 415 may include electrical connections 1003 on the exterior surface that enable electrical coupling to traces integrated into flexible body 410. Such an arrangement may allow the traces and electrodes to be disposable and replaced with ease. Coupling between trace and housing may be enabled by conductive adhesive, conductive glue, conductive gel, or other suitable conductive material. In some embodiments, a top protective layer (not shown) may be provided over the traces 411, 412 and optionally over the rigid body 410 after they are coupled to the flexible body 410. The top protective layer may be coupled (e.g., adhered) to the flexible body 410. The top protective layer may be coupled to the flexible body prior to cutting the floating section flexible body 410 so that overlapping cuts are imposed on both the flexible body 410 and the top protective layer. In some embodiments, the top protective layer may be provided in a pre-cut form.

The flexible body 410 of the physiological monitoring device 400 may be replaceable. The flexible body 410 may be removed from the housing 415 and electrode traces 411, 412 and a replacement flexible body 410 may be reapplied in the same manner as the original was assembled. In certain embodiments discussed herein, the flexible body 410 may include the electrode traces 411, 412 and flexible body 410 may be removed from the housing 415 to be replaced by another in the same location. This embodiment of the physiological monitoring device 400 may provide a convenient method for replacing the adhesive layers of the physiological monitoring device 400 after the adhesive layers have begun to wear and/or peel, allowing for a longer duration of use of the device 400.

Physiological Monitoring Device

Figure 6A:
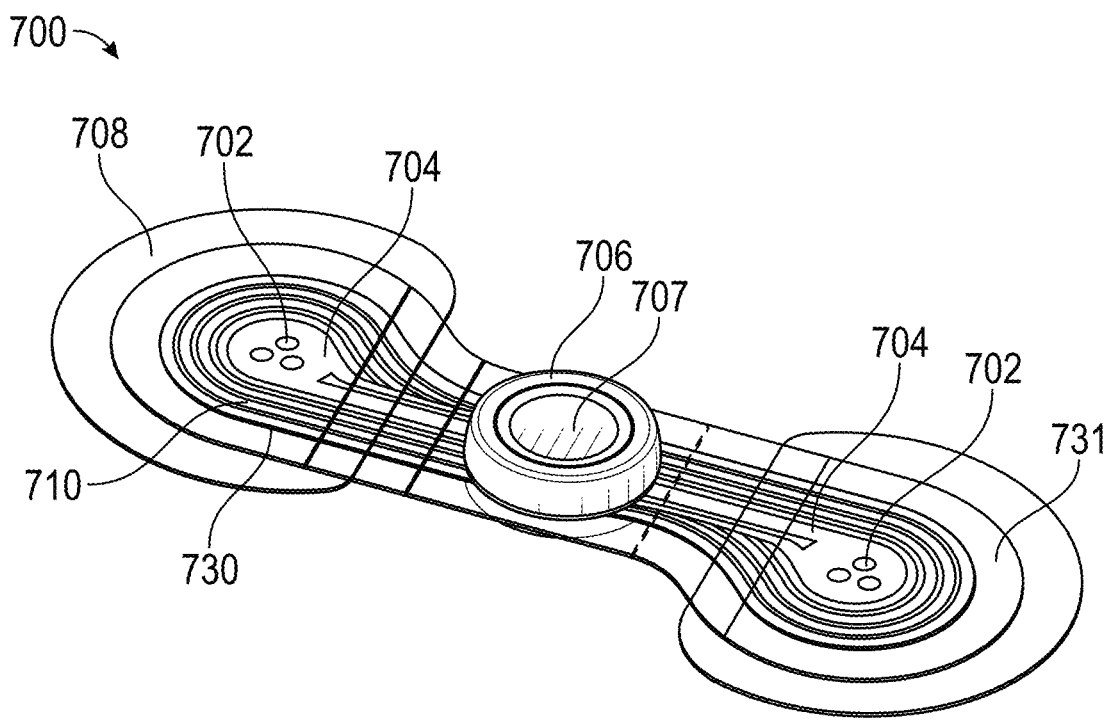
Figure 6B:
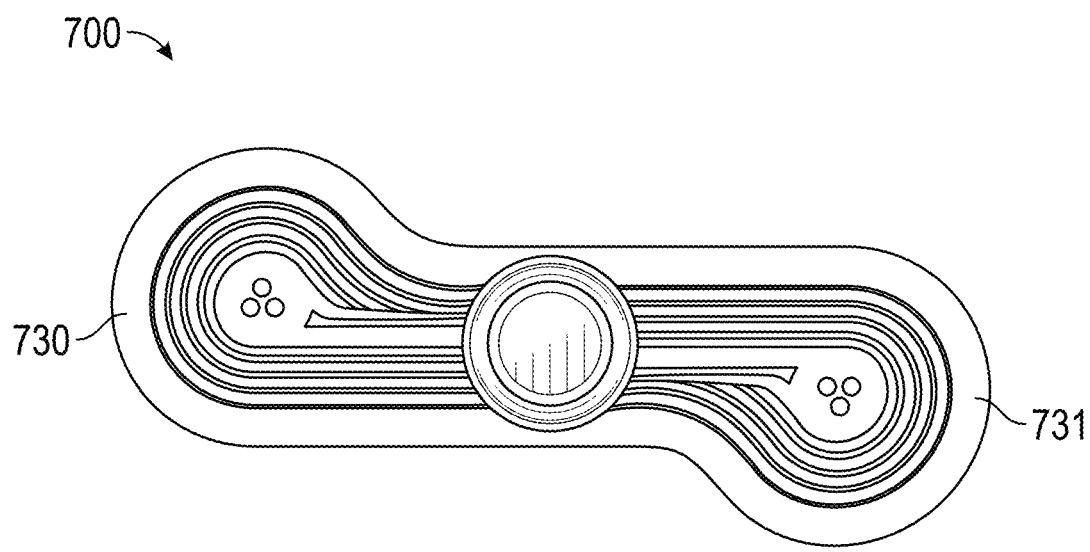
Figure 6C:
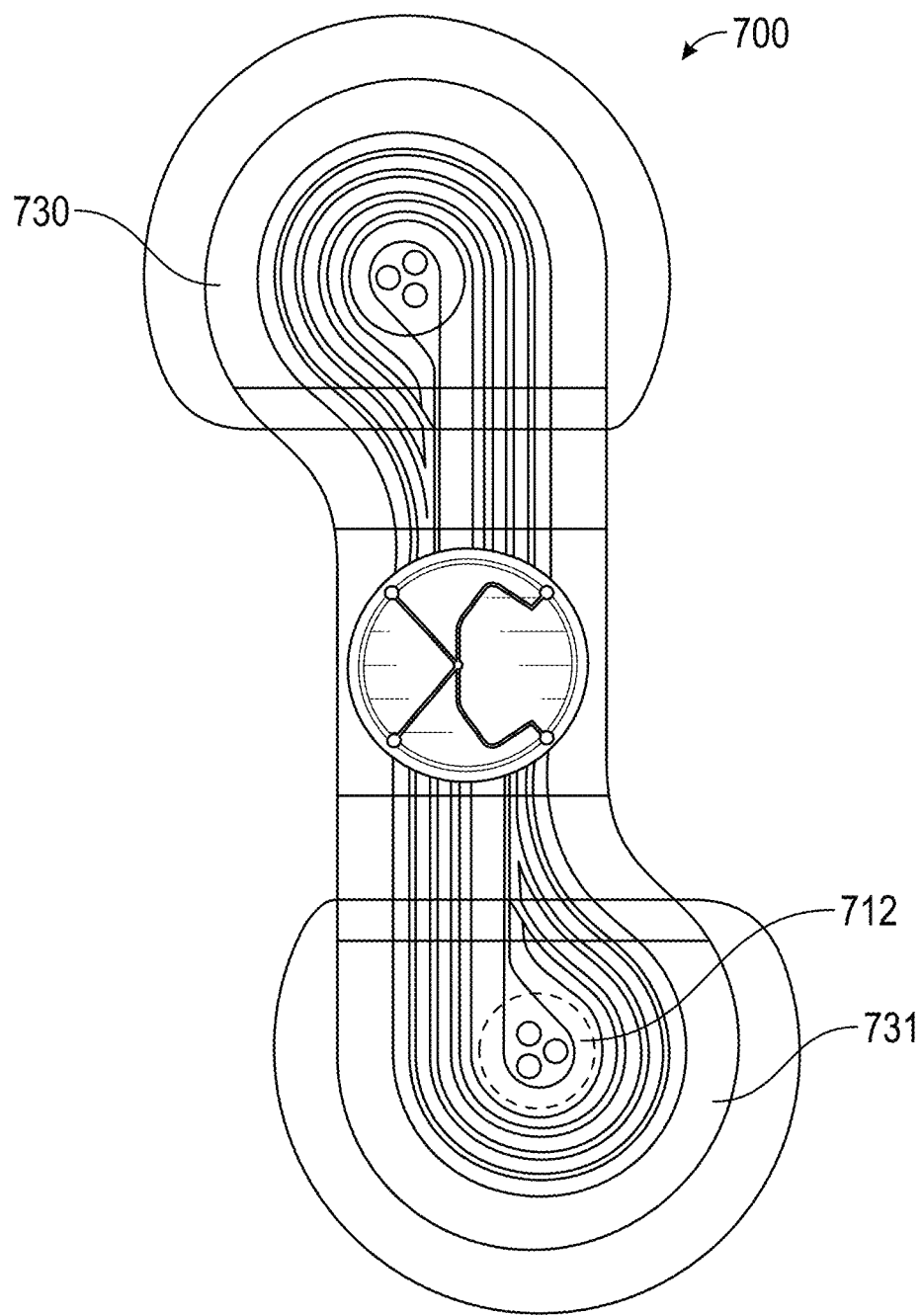

FIGS. 6A-6H depict an embodiment of a physiological monitoring device 700, similar to the physiological monitoring devices depicted in FIGS. 1A-5H. FIG. 6A depicts a perspective view of the physiological monitoring device. As in FIG. 5A, the physiological monitoring device 700 may comprise wings 730, 731 which are each asymmetrical about a longitudinal axis approximately extending between the electrode interface portions 702 which overlie the electrodes positioned on the underside of the wings. Electrode traces 704, may extend from the housing to the electrodes, to provide electrical communication between the electrode and the central housing. As in FIG. 5A, above, one of the wings 730 may comprise a body which is disproportionately distributed above the longitudinal axis and the other wing 731 may comprise a body which is disproportionately distributed below the longitudinal axis. Therefore, the wings 730, 731, may make the flexible body asymmetric about a transverse axis, perpendicular to the longitudinal axis and extending through the housing 706, which may include patient trigger 707, similar to the other patient triggers disclosed herein this section or elsewhere in the specification. As described elsewhere herein, in certain embodiments, the patient trigger may encompass about: 10 to 30% of the total top area, such as about 20% of the top area or about 23% such as about 22.8% of the total top area. In certain embodiments, the patient trigger may encompass more than about 20%, more than about 30%, more than about 40%, more than about 50%, or more than about 75%. In certain examples, the patient trigger may encompass the entire top surface of the housing. The wings 730, 731 may comprise identical shapes which are reversed or flipped about both the longitudinal axis and the transverse axis as shown in FIGS. 6A-6C. In some embodiments, the wings may be asymmetrical in size and shape, for example the upper wing 730 may be larger than the lower wing 731 or vice-versa. The shapes of the wings 730, 731 may differ such that the relative shape of upper wing 730, differs from the relative shape of lower wing 731. In certain examples, the upper wing 730 may be under greater tension than the lower wing 731 or vice-versa, therefore different sizes and shapes between the two wings may aid in addressing unique force vectors during use of the physiological monitoring device. The configuration of the wings may be particularly suitable for positioning the electrodes in a diagonal arrangement with respect to the height of a subject, therefore potentially reducing peel off due to gravity. One of skill in the art will understand that the orientation of the wings may altered, such that the wings are mirrored, rather than being distributed disproportionately above or below a longitudinal axis. Further, those of skill in the art will understand that the shape of such wings, as described herein, may vary from the generally rounded shapes depicted in FIGS. 5-6. For example, the wings may be angular, such as a square shape, rectangular shape, triangular shape, pentagonal shape, or any suitable polygonal shape. These polygonal shapes may have rounded corners to reduce likelihood of peeling from the corner. A liner 708, such as depicted elsewhere herein may be used to cover and protect any adhesive, prior to application of the physiological monitoring device to a patient or user. In embodiments, the liner may be separated into two parts, one over each wing.

Figure 6E:
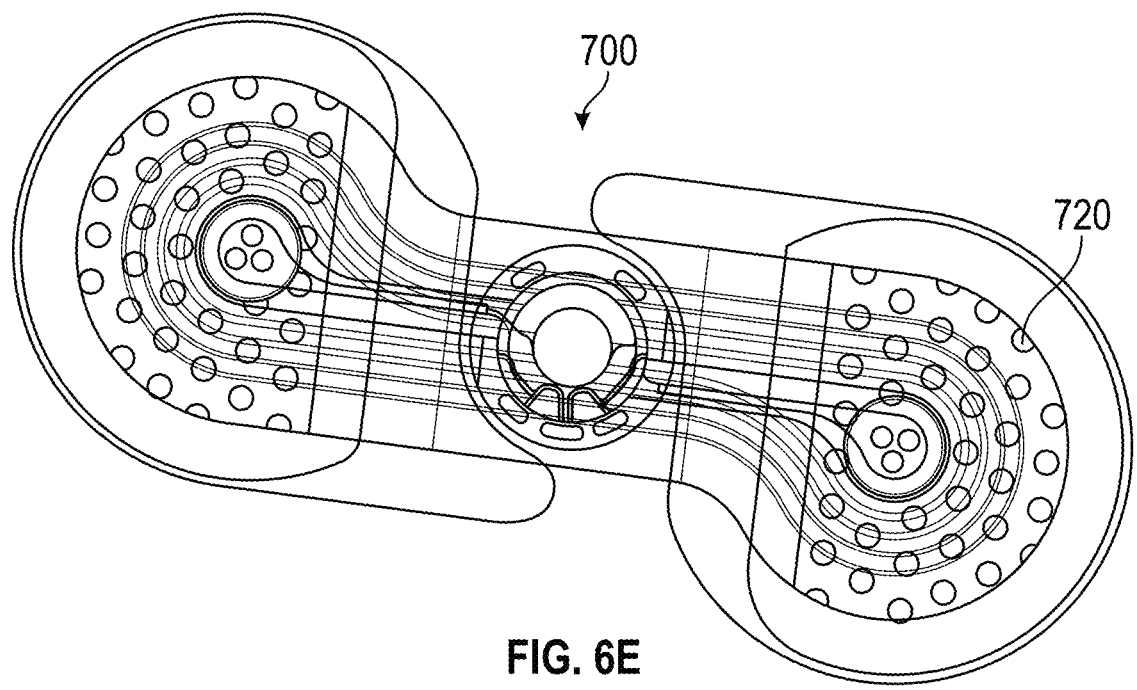
Figure 6F:
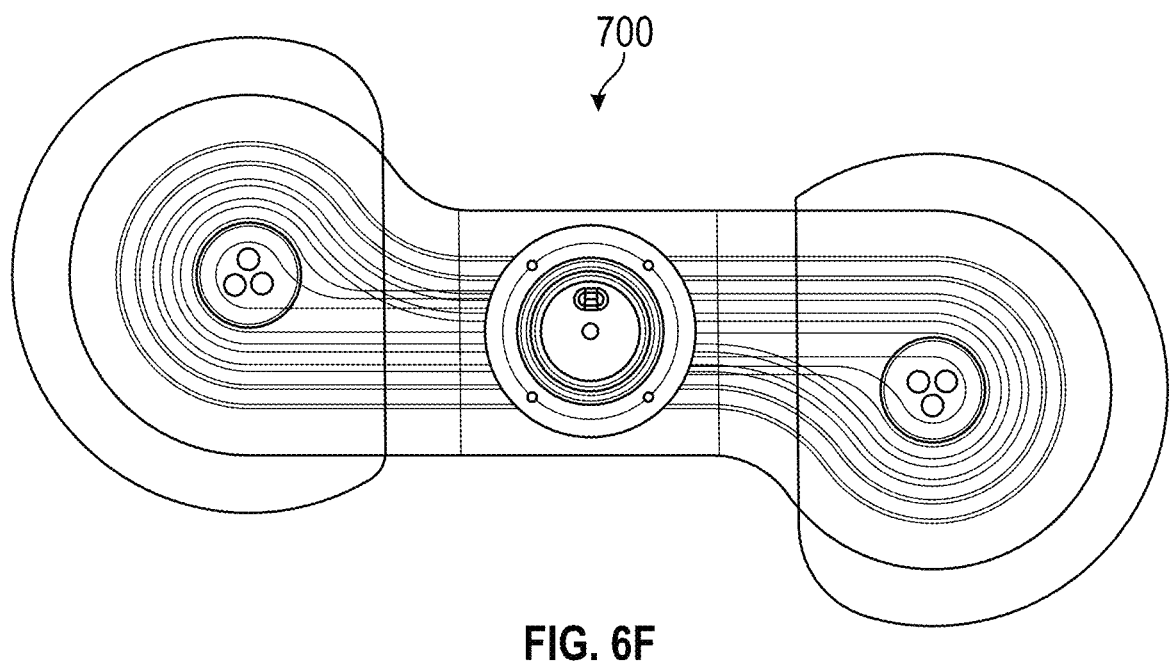

In certain embodiments, an additional visualization pattern 710 may extend through the wing. The visualization pattern 710 may be in any suitable size or shape to outline the electrode trace and frame the shape of the wings, for example, the visualization pattern 710 may be in the form of lines, such as rounded lines to reflect the contours of the electrode trace and the shape of the wings. In certain embodiments, there may be one, two, three, four, or more lines. In some embodiments, the visualization pattern may be formed from a pattern of dots, shapes or other combinations such that the visual cleanliness of the device is maintained as the otherwise clear adhesive layer becomes less visually acceptable to the user through the course of the wear period (e.g. if the adhesive layer picks up foreign material and/or becomes cloudy with absorption of moisture). In certain embodiments, the visualization pattern may have another functional purpose of alerting the user to how long they have been wearing the device, for example, by changing color over time or wearing down. This change in appearance may alert the user to remove the device at the right time. FIG. 6B shows a top view of an embodiment of the physiological device 700, while FIG. 6C shows a bottom view, and FIG. 6D1 depicts a side view. In FIG. 6C, the flexible electrodes 712 are visible. As shown in FIG. 6D1, top 714 and bottom housing 716 portions of the housing may be positioned above and below the flexible body 718. FIGS. 6E and 6F show the underside and topside of the physiological monitoring device 700, with each layer transparent such that all layers are visible. Each layer will be described below in greater detail in the exploded view of the physiological monitoring device 700. Apertures 720, similar to the apertures depicted above in the embodiments of FIG. 5, may be positioned in a substrate layer positioned above the adhesive layer. As described above in greater detail, such apertures may provide breathability through one or more layers and may promote transpiration of moisture from below the adhesive layer through the layer or layers comprising the apertures. As shown in FIG. 6D2, in embodiments, a gasket 719 may be positioned between the upper housing cover 714 and lower housing 716, co-molded into one or more of the housings. The gasket may compress down on the adhesive assembly and a ridged interface (shown below in FIG. 6D2) or another gasket on the opposite housing to provide waterproofing to the internal electronics hardware. As depicted in FIG. 6B2, a ridge 721 may be positioned on an upper edge of the lower housing 716, the ridge 721 configured to press into the adhesive layer 719. One of skill in the art will understand that the ridge 721 may be of any suitable shape, for example such as an edged ridge as depicted in FIG. 721. In some examples, the ridge may be rounded, square, and/or polygonal. In certain examples, the height of the ridge may be about 0.01 mm to 0.5 mm, about 0.05 mm to 0.4 mm, about 0.1 mm to 0.3 mm, about 0.1 mm to 0.2 mm, or about 0.15 mm such as about 0.13 mm.

Figure 6G:
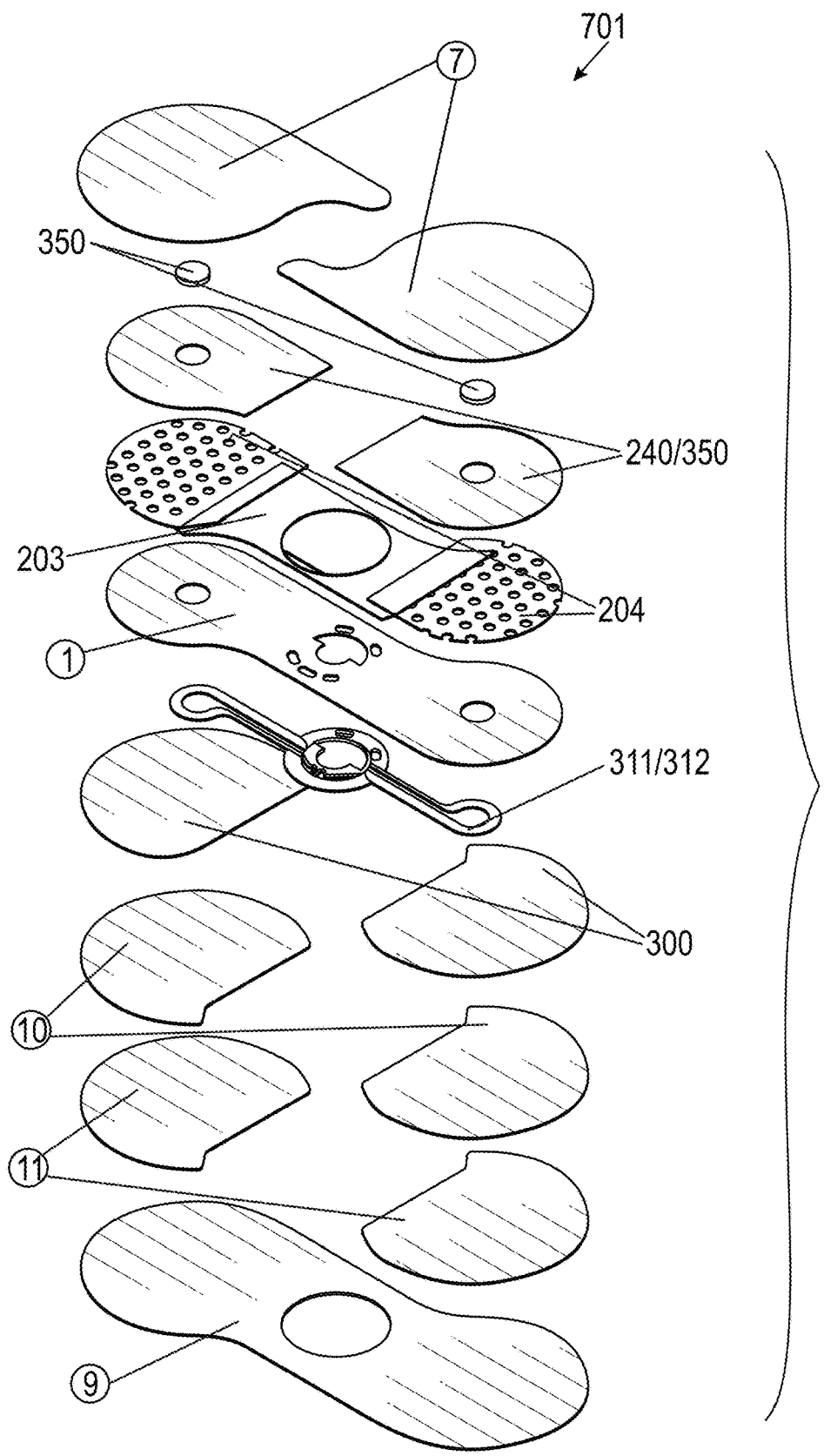

FIG. 6G depicts an exploded view of an embodiment of flexible body 701 of the physiological monitoring device 700 described herein this section and elsewhere in the specification. The housing 706 is not shown. As will be understood by one of skill in the art, the image in FIG. 6G is oriented upside down in relation to positioning on the skin. Following the numbering within FIG. 6G, #7 depicts a release liner, which protects the adhesive layer (240/340 and hydrogel electrodes 350. Directly above the adhesive layer are a perforated layer 204 (containing apertures such as described herein) and a flap layer 203. In certain embodiments, the perforated layer and flap layers may be constructed from any suitable material, such as polyethylene terephthalate (PET) and/or polyurethane. Directly above the perforated layer may be a lower substrate layer #1, which may be constructed of polyurethane. In embodiments, the lower substrate layer may have at least one textured side, this side may be positioned such that the textured side faces flap layer #3. In embodiments, flap layer #3 may also include at least textured side. This textured side may be configured to face lower substrate layer #1. The conductive electrode traces may be printed on an additional, separate substrate (311,312). Or, in some embodiments, conductive electrode traces may be printed directly on the substrate layer #1. Positioned above the conductive electrode traces may be an upper substrate layer 300. Positioned over the upper substrate layer may be an additional carrier layer #10, followed by an adhesive layer #11 and a topmost rigid liner #9. One of skill in the art will understand that such an arrangement of layers may be applicable to any embodiment of a physiological monitor described herein, such as the embodiments of FIG. 5H, FIGS. 8A-8D, and FIGS. 6A-6F.

Figure 6H:
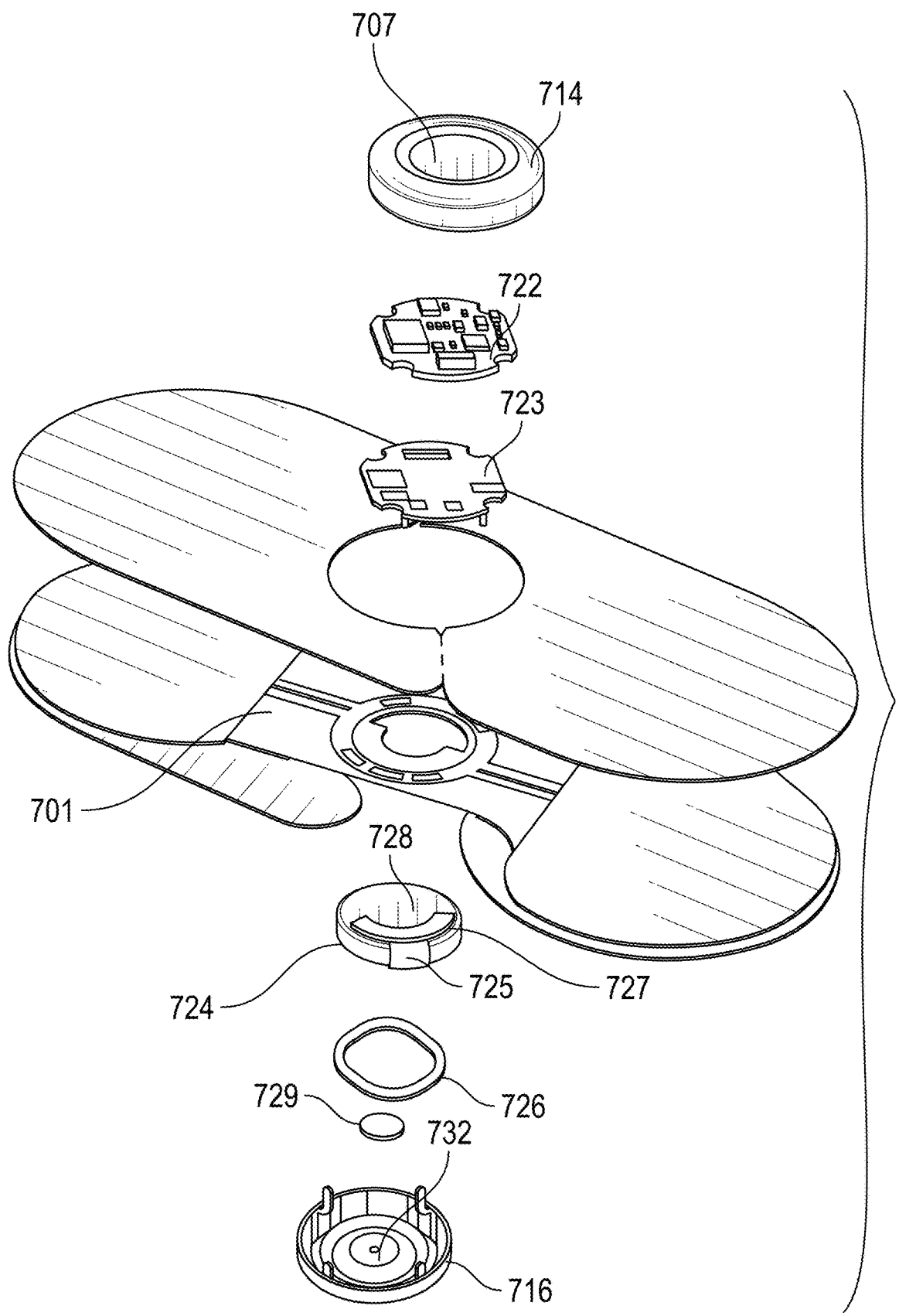

FIG. 6H depicts an exploded view of an embodiment of the housing 706 of the physiological monitor device 700, through which passes flexible body 701, described in detail above. Top housing cover 714 may include a patient trigger 707. Top housing cover may encase circuit board 722. Spacer 723, positioned below the circuit board, is configured to maintain consistent spacing between the conductive contact springs that are on the underside of the circuit board and the battery terminals/ECG trace contacts. The spacer may additionally provide electrical insulation between the circuit board and battery. There may be holes in the spacer to allow conductive contact springs to pass through, the contact springs connected to the circuit board. Battery terminal 725, may be positioned below the flexible body 701 and circuit boards 722, thereby overlying wave spring 726. In embodiments, the battery terminal 725 may be wrapped around and adhered to a coin cell battery 728. The battery terminal 725 may be constructed as a flex circuit with conductive vias 727 that enables the positive underside of the coin cell battery 728 to be brought up to the negative top side of the battery, so that both the negative and positive terminals are presented on the top side of the battery to meet the circuit board contact springs. Alternatively, a battery contact or contacts in the bottom housing can enable the positive underside of the coin cell battery to be brought up to the negative top side to contact the circuit board. Venting layer 729 may be positioned against lower housing portion 716, over a vent hole 732 in the lower housing. In embodiments, the venting layer may be constructed from a material that blocks liquid passage while allowing gas passage, for example ePTFE or any other suitable material. The vent hole 732 in combination with the venting layer allows normalization of air pressure between the outside and inside of the housing. In embodiments, the vent hole 732 in combination with the venting layer prevents button and/or trigger 707 from blowing out or sucking in depending on external air pressure, for example if the patient is at a different altitude such as on a plane. The venting layer may be thin and round with adhesive in a ring configuration on the bottom. The area of the venting layer coated in adhesive may not be gas permeable, while the central portion may be gas permeable but liquid impermeable. The central portion of the venting layer may be positioned over the vent hole, thereby allowing gas passage into and out of the housing while limiting liquid egress and ingress. In certain embodiments, the venting layer may be integrated into the bottom housing by molding it in, or it could also be ultrasonically welded into the bottom housing, or adhered via any suitable means.

Figure 7A:
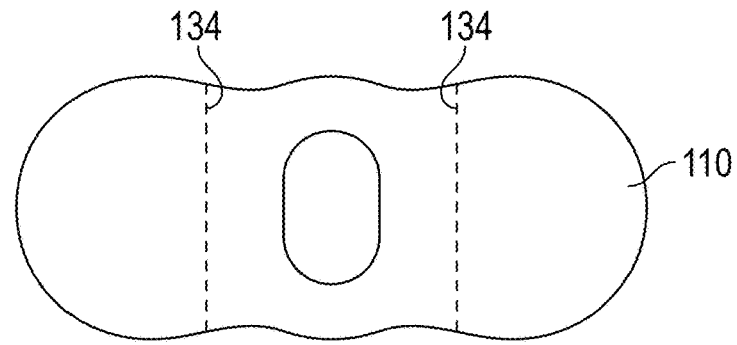
FIG. 7A schematically illustrates the profile of a substrate layer of a flexible body having hinge lines between which the flexible body is configured to float.
Figure 7B:
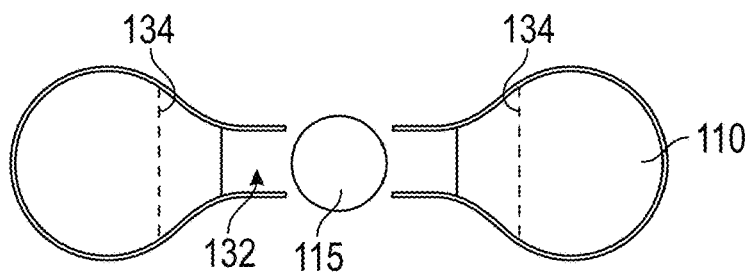
FIGS. 7B-7D schematically illustrate various examples of configurations of adhesive layers comprising bridges designed to be coupled to the flexible body and to extend underneath the housing.
Figure 7C:
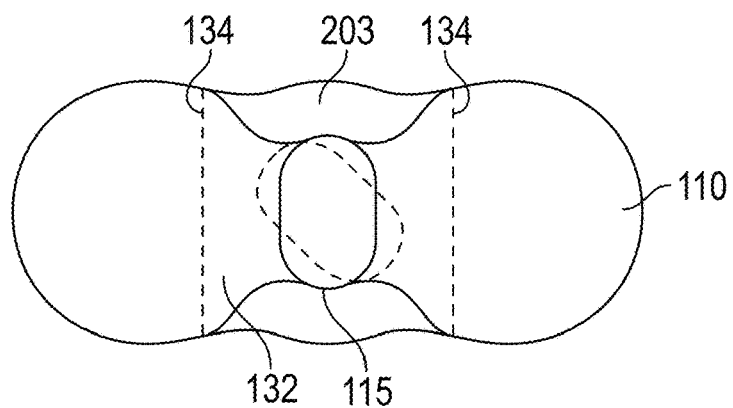
Figure 7D:
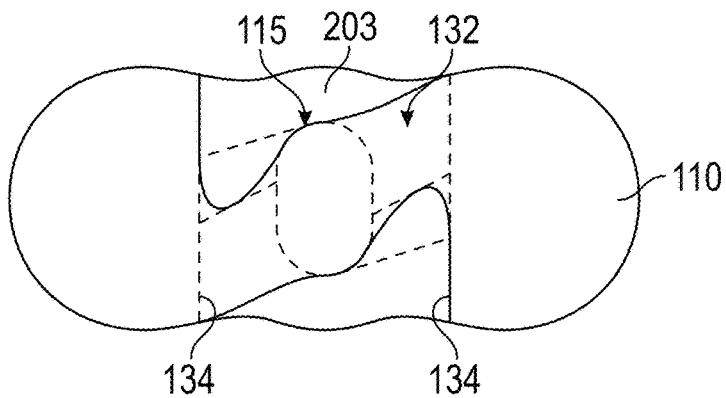

As shown in FIGS. 7A-7B, in some embodiments, the butterfly flap layer 203 may extend directly below the housing 115, 706 (in FIGS. 6A and 5H above). The non-adhesive top surface of the butterfly flap layer 203 may prevent the housing from adhering to the butterfly flap. Additionally, a central portion of the flexible body 110 (e.g. hinge portions 132) may be configured to float above the skin of the subject and above the butterfly flap layer 203. FIG. 7A schematically illustrates the profile of a flexible body 110 having hinge lines 134 between which the flexible body 110 is configured to lift off the skin of the subject. The adhesive layer 340 may be adhered to the overlying substrate layers of the flexible body 110 (e.g., bottom substrate layer 330) outside of the hinge lines 134 and adhered to the butterfly flap layer 203 between the hinge lines 134. Figure A illustrates an embodiment where the width of the flexible body 110 extends beyond the diameter of the housing 115. FIGS. 7B-7D schematically illustrate various examples of configurations of adhesive layers 340 comprising butterfly flaps layer 203 designed to be coupled to the flexible body 110 and to extend underneath the housing 115. The shape (e.g., the outer profile) of the adhesive layer 340 may be configured to mechanically distributed forces across the adhesive layer 340 in a manner that prevents or inhibits peeling of the adhesive layer 340 from the skin of the subject in order to promote a longer duration of wear. The outer edges of the adhesive layer 340 may comprise generally steep angles, particularly where the outer edge of the adhesive layer 340 intersects the hinge lines 134. The steep angles may be configured to promote a distribution of stresses through the adhesive layer 340 that maximize multiple directional vectors of stress, for example shear and tensile stresses, between the adhesive layer 340 and the skin of the subject and/or minimizes peel stresses between the adhesive layer 340 and the skin of the subject. Shear stresses and tensile stresses may be less likely to cause separation of the adhesive layer 340 from the skin. By shifting stress into non-peeling vectors, long-term adhesion may be improved.

For example, FIG. 7B illustrates a flexible body 110 having a profile generally resembling an accentuated bowtie, Papillon ears, and/or a round dumbbell. The flexible body 110 may comprise a longitudinal axis extending from the outer edge of one of the wings 130, 131 to the outer edge of the other and symmetrically bisecting the two wings 130, 131. The flexible body 110 may have a transverse axis perpendicular to the longitudinal axis and symmetrically dividing the flexible body 110 (e.g., the bottom substrate layer 330), separating the two wings 130, 131. The hinge portion 132 of the flexible body of the device 100 may extend between the hinge lines 134 of the two wings 130, 131. The hinge portion 132 may symmetrically bisect the adhesive layer 340 in the longitudinal direction. The hinge portion 132 may be narrower in the transverse direction than the two wings 130, 131. The hinge portion 132 may be narrower in the transverse direction than the underlying substrate layers (e.g., butterfly flap layer 203). The outer edge of the flexible body 110 may extend inward toward the longitudinal axis and the transverse axis from the hinge lines 134. The outer edges may have a curved shape where the outer edges intersect the hinge lines 134. In some embodiments, the outer edges may each comprise an inflection point at which the outer edges transition from a convex curvature to a concave curvature. The concave curvature may be positioned closer to the transverse axis than convex curvature. The inflection point may be positioned on the hinge line 134, outside the hinge line 134 (opposite the transverse axis), or inside the hinge line 134 (same side as the transverse axis). The curved edge of the adhesive layer 340 where the adhesive layer 340 intersects the hinge line 135 may adjust the vector of pull away from the edge by changing the angle of the edge as it extends across the hinge line 134, a point where the adhesive layer 340 may be particularly prone to peel.

FIG. 7C illustrates another embodiment of a flexible body 110 generally similar to that shown in FIG. 7B. However, as shown in FIG. 7C, the flexible body 110 (which may be layered with an adhesive layer) may be configured such that the housing 115 may be oriented at an angle offset from the transverse axis with respect to the flexible body 110. Such a configuration may allow for the physiological monitoring device 100 to be worn by the subject at an angle (e.g., FIGS. 9B-9F) while maintaining an alignment of a longitudinal axis of the housing 115 with an axis extending the height of the subject. Any of the embodiments disclosed herein may be modified in the same manner to reorient the housing 115 to accommodate for an expected orientation of adhesion of the flexible body 110 to the subject. FIG. 7D illustrates another configuration of a flexible body 110 including a hinge portion 132 configured to resist peeling mechanics. The flexible body 110 may comprise an outer profile generally having a "z-shaped" configuration or a backwards "z-shaped" configuration, as shown in FIG. 7D. The hinge portion 132 may extend between the hinge lines 134. The hinge portion 132 may extend from a lower inside corner of the flexible body 110 of one of the two wings 130, 131 to an upper inside corner of the flexible body 110 of the opposite wing. In some embodiments, the hinge portion 132 may be generally linear having a consistent width across a length of the hinge portion 132. In some embodiments, the outer edges of the flexible body 110 may be smoothed or somewhat rounded at intersections between the hinge portion 132 and the housing 115 and/or between the hinge portion 132 and the portions of the flexible body 110 outside the hinge lines 134, as shown in FIG. 7D. Accordingly, there may be no sharp corners along the hinge portion 132. The "z-shaped" configuration may reduce the length of the edges of the flexible body 110 which are aligned with and/or parallel to the hinge lines 134, which may be the edges of the adhesive layer 340 that are most prone to peel. The sharp bends between the hinge portion 132 and the edges along the hinge lines 134 may increase the shear forces aligned along the hinge line 134 and reduce the likelihood of peeling, particularly closer to the intersection between the hinge portion 132 and the hinge line 134. This may be achieved by minimizing connection between hinge portion 132 and the central housing 115 in situations when the subject's body is in a position that subjects the patch to torsional forces (as shown in FIG. 13B).

Figure 7E:
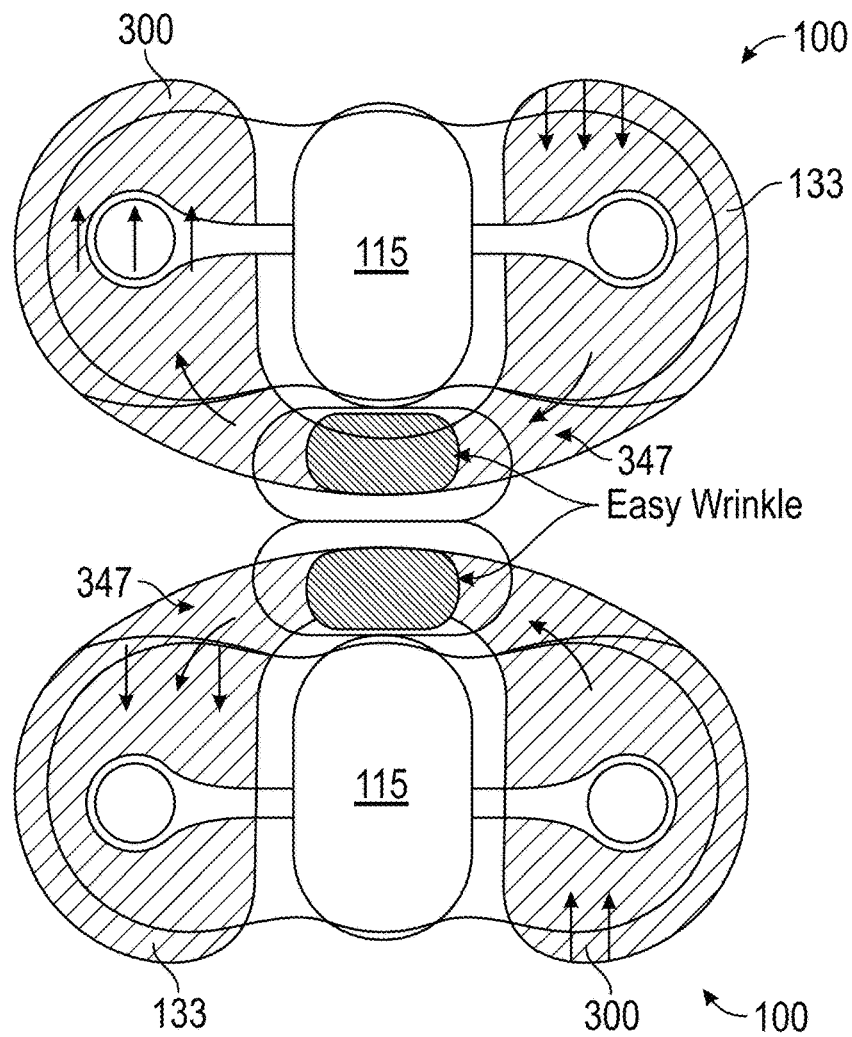
FIG. 7E schematically illustrates bottom views of physiological monitoring devices comprising a single adhesive layer having a "headphone" shaped configuration and comprising a bridge portion.

In some embodiments, the top substrate layer 300 may be replaced by the subject at some period of time into the intended wear period, such as about: 6 hours, 12 hours, 1 day, 2 days, 4 days, 1 week, or a period longer than one week, in order to extend duration of wear as well as refresh the aesthetic appearance of the device. In certain embodiments the top substrate layer 300 may exist as two separate pieces without intersecting housing 114, as shown in FIG. 6G, each piece can be removed independently and replaced by new adhesive-backed pieces. The manner of removal may be enabled by non-adhesive pull-tab features on substrate layer 300 or other protrusions, whether adhered or not adhered to the subject's skin. Replacement of top substrate layer 300 with fresh adhesive-backed sections may be enabled through similar means as used in the original application. The top substrate layer 300 may be supported by a rigid liner and protected by a release liner, where the release liner may be removed prior to application and the rigid liner may be removed after applying to the skin. The top substrate layer 300 may be a single integral piece, as shown in FIG. 3B, or it may be two or more separate pieces, as shown in FIG. 6G. As shown in FIG. 7E, top substrate layer may also be a single integral piece joined in a section that does not intersect with housing 115. The top substrate layer 300 may include a thin adhesive layer on its bottom surface, connecting top substrate layer 300 to the other substrates of flexible body 110 and connecting substrate layer 300 to the subject's skin along border 133. A bridge portion 347 may join right and left portions of the top substrate layer 300 positioned below the two wings 130, 131. FIG. 7E schematically illustrates a bottom view of physiological monitoring devices 100 comprising a single top substrate layer 300 comprising a bridge portion 347. In some embodiments, the bridge portion 347 may extend around (e.g., a height in the horizontal plane higher than or lower than) a central portion of the flexible body 110 coupled to the housing 115. FIG. 7E illustrates physiological monitoring devices 100 having bridges 347 that extend around the housing 115 in opposite directions. The bridge portion 347 may comprise a generally curved or arcuate shape. The top substrate layer 300 may comprise a "headphone" shape as illustrated in FIG. 7E. The bottom surface of the bridge portion 347 may be adhesive such that the bridge portion 347 is configured to adhere to the skin of the subject. In some embodiments, the bottom surface of the bridge portion 347 may not be adhesive such that the bridge portion 347 does not adhere to the skin of the subject. The top surface of the bridge portion 347 may be non-adhesive since it will be exposed when the physiological monitoring device 100 is worn by the subject.

The arrows in FIG. 7E schematically illustrates a possible preferred direction of removing the top substrate layer 300, if replaceable, from the flexible body 110. The adhesive layer 340 may be removed from one of the two wings 130, 131 prior to the other. The adhesive-backed top substrate layer 300 may be peeled from the flexible body 110 on a side opposite the bridge portion 347 (e.g., beginning at an inside corner as described elsewhere herein) and once the adhesive layer 340 is removed from one of the wings 130, 131, the adhesive-backed top substrate layer 300 may be removed from the other wing 130, 131 by peeling the adhesive-backed top substrate layer 300 from the second wing beginning at where the bridge portion 347 meets the second wing (e.g., beginning at an inside corner). In other implementations, the adhesive-backed top substrate layer 300 may be removed from the two wings 130, 131 substantially simultaneously by pulling the bridge portion 347 under and across the bottom surface of the flexible body 110 and the housing 115. In some implementations, the bridge portion 347 may be cut (e.g., substantially along the center of the bridge 347) creating two free ends which may be used to peel the adhesive layer 340 from each of the two wings 130, 131.

In some embodiments, placement of adhesive-backed top substrate layer 300 may be facilitated through application of a single monolithic piece without features or cutouts. This type of layer could be applied over the top of an entire device 100 for additional securement during wear, or placed after removal of adhesive-backed top substrate layer 300 as a replacement. In other embodiments, the adhesive-backed top substrate layer for additional securement or replacement may be a single piece with feature cutouts such as shown in FIG. 8D, allowing the housing 115 and hinge portions 132 to float free of the skin.

Figure 7F:
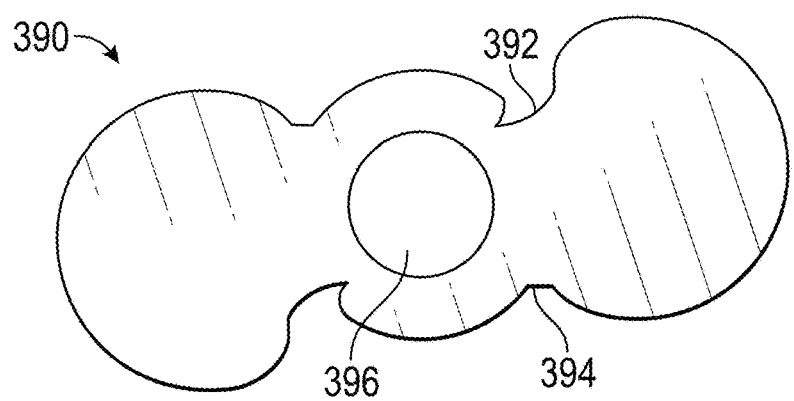
FIG. 7F depicts an embodiment of a wing shape.

FIG. 7F depicts an embodiment 390 of a wing shape similar to the embodiments of FIGS. 7A-7E. Here, as in FIGS. 5G-5H and 6A-6H, the wings are asymmetric, with a greater portion of one wing lying above the longitudinal line and a greater portion of another wing lying below the longitudinal line. However, here the wings include a sharp notch and a blunted notch 394. The sharp notch may allow the wing to more easily flex and rotate in a clockwise or counterclockwise direction around a z axis extending directly through the center of the hole 396.

Figure 9:
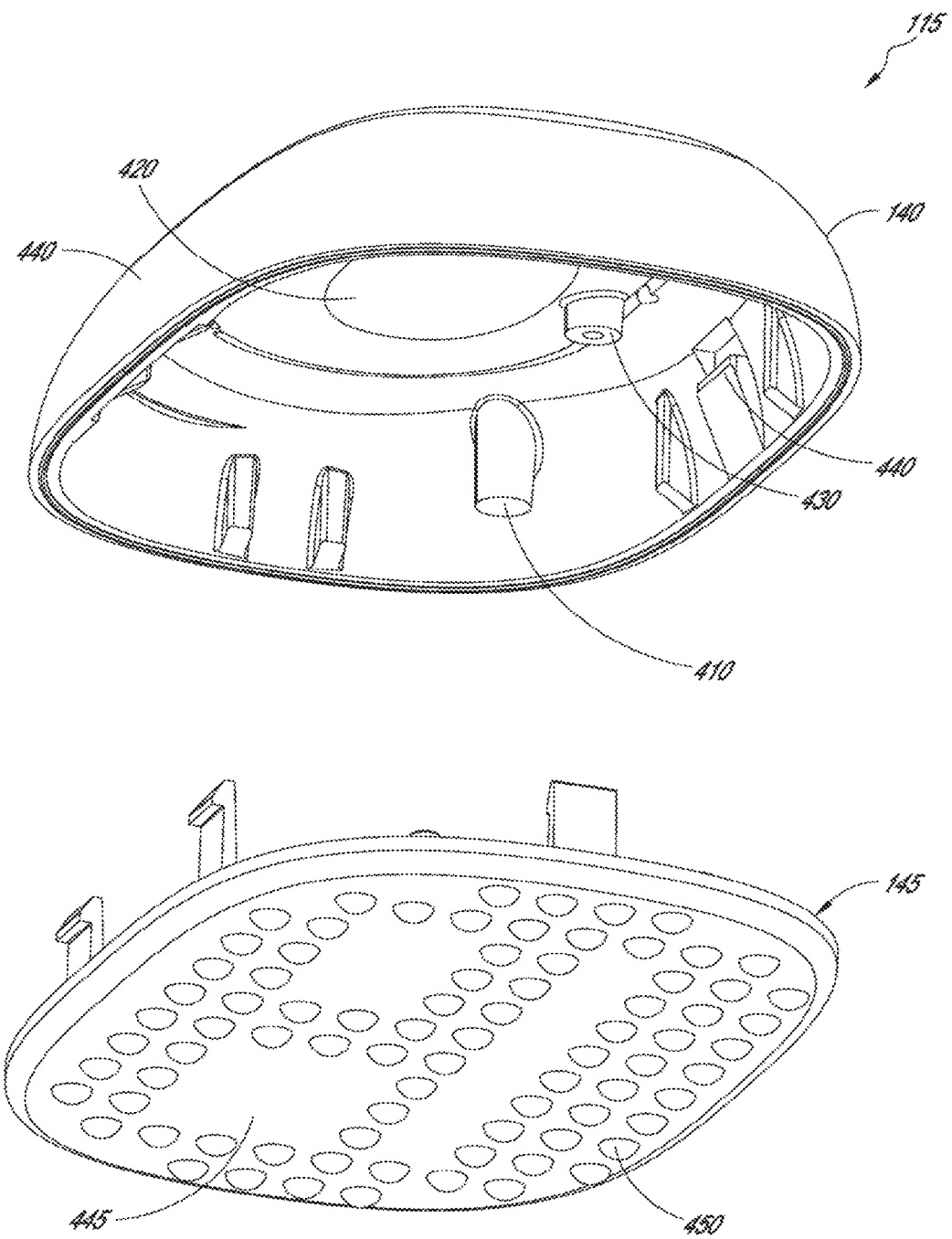
FIG. 9 is a view of a top portion and a bottom portion of a housing of the physiological monitoring device, according to one embodiment.

With reference now to the embodiment of FIG. 9, upper housing member 140 and lower housing member 145 of housing 115 are shown in greater detail. Upper and lower housing members 140, 145 may be configured, when coupled together with gaskets 360, 370 in between, to form a watertight enclosure for containing PCBA 120, battery holder 150, batteries 160 and any other components contained within housing 115. Housing members 140, 145 may be made of any suitable material to protect internal components, such as water resistant plastic. In one embodiment, upper housing member 140 may include a rigid sidewall and/or hook 440, a light pipe 410 to transmit visual information from the LEDs on the PCBA through the housing member, a slightly flexible top surface 420, and an inner trigger member 430 extending inward from top surface 420. Top surface 420 is configured to be depressed by a patient when the patient perceives what he or she believes to be an arrhythmia or other cardiac event. When depressed, top surface 420 depresses inner trigger member 430, which contacts and activates trigger input 210 of PCBA 120. Additionally, as discussed previously, top surface 420 may have a concave shape (concavity facing the inside of housing 115) to accommodate the shape of a finger. It is believed that the design of upper housing member 140 isolates activation of the trigger input 210 from electrodes 350, thereby minimizing artifact in the data recording.

With continued reference to FIG. 9, lower housing member 145 may be configured to detachably connect with upper housing member 140 in such a way that housing members 140, 145 may be easily attached and detached for reusability of at least some of the component parts of monitoring device 100. In some embodiments, a bottom surface 445 (patient facing surface) of lower housing member 145 may include multiple dimples 450 (or "bumps," "protrusions" or the like), which will contact the patient's skin during use. Dimples 450 may allow for air flow between bottom surface 445 and the patient's skin, thus preventing a seal from forming between bottom surface 445 and the skin. It is believed that dimples 450 improve comfort and help prevent a perception in currently available devices in which the patient feels as if monitoring device 100 is falling off when it housing 115 lifts off the skin and breaks a seal with the skin. In yet another embodiment the bottom surface 445 of lower housing member 145 may include multiple divots (recesses instead of protrusions, such as shown in FIG. 6C) to prevent a seal from forming.

Figure 10A:
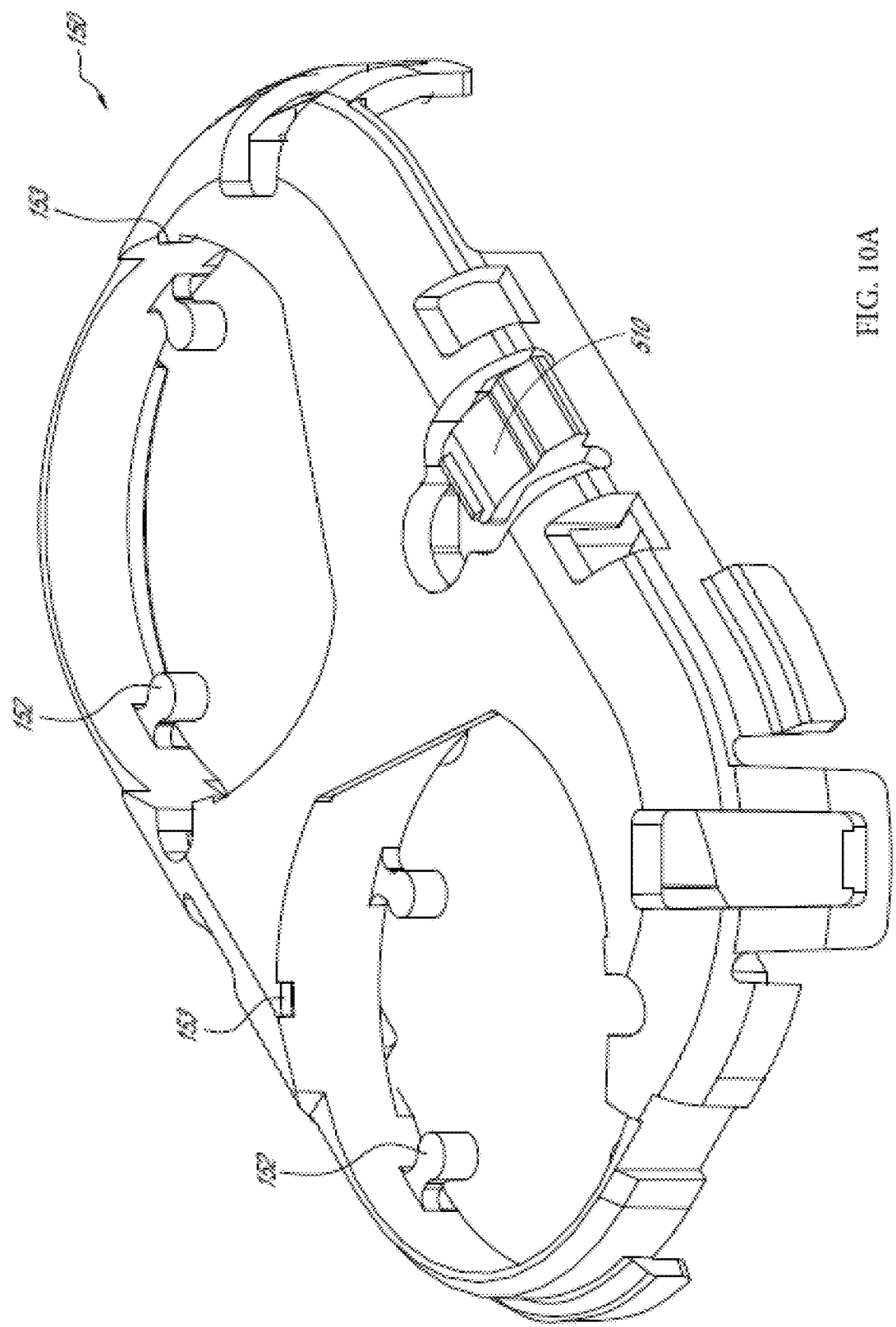

Referring now to the embodiment of FIG. 10A, battery holder 150 is shown in greater detail. Battery holder 150 may be made of plastic or other suitable material, is configured to be mounted to PCBA 120 and subsequently attached to housing 115, and is capable of holding two batteries 160 (FIG. 1B). In alternative embodiments, battery holder 150 may be configured to hold one battery or more than two batteries. A plurality of protrusions 152 provide a stable platform for batteries 160 to be positioned a fixed distance above the surface of PCBA 120, avoiding unwanted contact with sensitive electronic components yet providing for adequate compression of spring contacts 235 (FIG. 10B). Protrusions 153 lock batteries 160 into position and resist the upward force on the batteries from spring contacts 235. Battery holder 150 also positions batteries appropriately 160 to provide for adequate compression of spring contacts 236. Use of battery holder 150 in conjunction with spring contacts 235 and 236 allows for batteries 160 to be electrically connected to PCBA 120 while still having additional electronic components between batteries 160 and PCBA 120 and maintain a very compact assembly. Battery holder 150 may include a flexible hook 510 which engages a corresponding rigid hook 440 of upper housing member 140. Under normal assembly conditions the flexible hook 510 remains securely mated with rigid hook 440. For disassembly, flexible hook 510 can be pushed and bent using an appropriate tool passed through top housing member 140 causing it to disengage from rigid hook 440 and subsequently allow top housing member 140 to be removed.

Figure 11A:
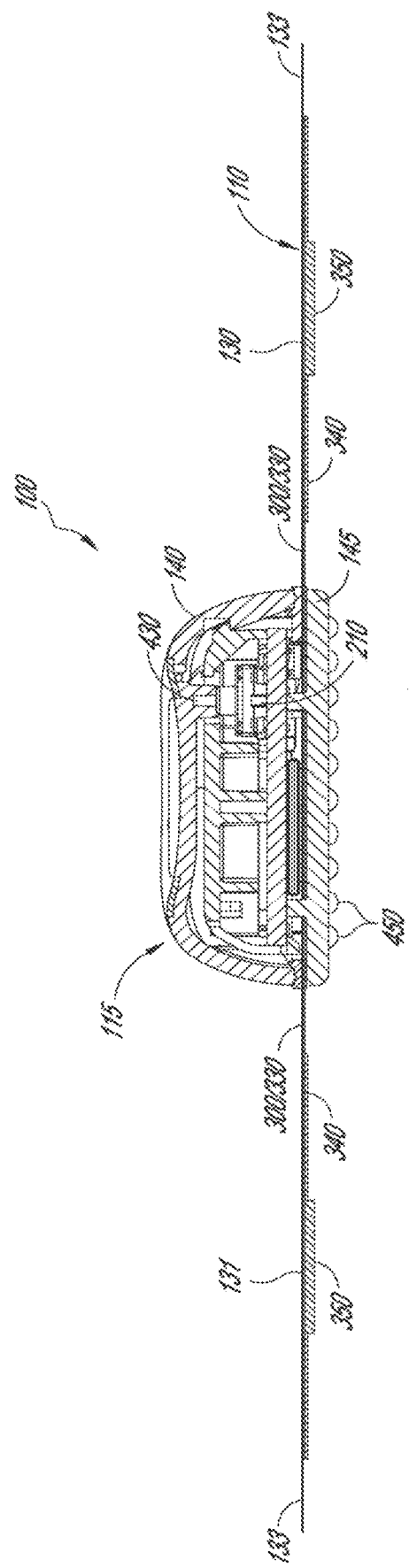
FIGS. 11A and 11B are cross sectional views of the physiological monitoring device, according to one embodiment.
Figure 11B:
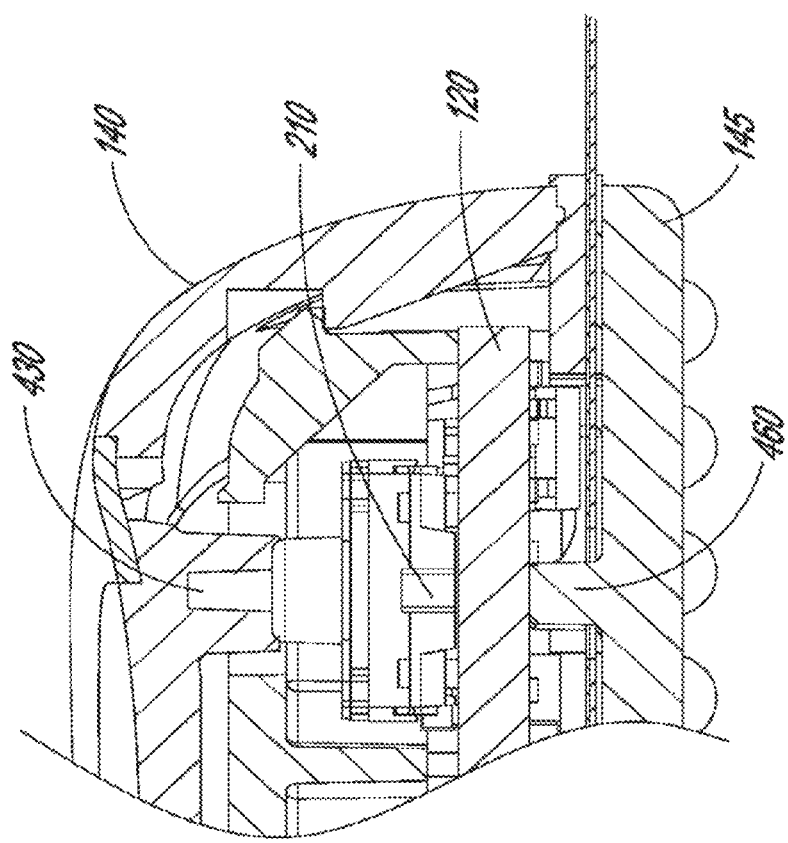

With reference now to the embodiments of FIGS. 11A and 11B, physiological monitoring device 100 is shown in side view cross-section. As shown in 6A, physiological monitoring device 100 may include flexible body 110 coupled with housing 115. Flexible body 110 may include top substrate layer 300, bottom substrate layer 330, adhesive layer 340 and electrodes 350. Electrode traces 311, 312 are also typically part of flexible body 110 and are embedded between top substrate layer 300 and bottom substrate layer 330, but they are not shown in FIG. 11. Flexible body 110 forms two wings 130, 131, extending to either side of housing 115, and a border 133 surrounding at least part of each wing 130, 131. Housing 115 may include an upper housing member 140 coupled with a lower housing member 145 such that it sandwiches a portion of flexible body 110 in between and provides a watertight, sealed compartment for PCBA 120. Upper housing member 140 may include inner trigger member 430, and PCBA may include patient trigger member 210. As discussed previously, lower housing member 145 may include multiple dimples 450 or divots to enhance the comfort of the monitoring device 100.

It is desirable that PCBA 120 is sufficiently rigid to prevent bending and introducing unwanted artifact into the signal. In certain embodiments, an additional mechanism to reduce and prevent unwanted bending of PCBA 120 may be used. This mechanism is shown in FIG. 11B. Support post 460 is integral to lower housing member 145 and is positioned directly under patient trigger input 210. During patient symptom triggering, upper housing member 140 is depressed, engaging inner trigger mechanism and/or member 430 and transmitting a force through patient trigger input 210 into PCBA 120. The force is further transmitted through PCBA 120 and into support post 460 without creating a bending moment, thus avoiding unwanted artifact.

Figure 12:
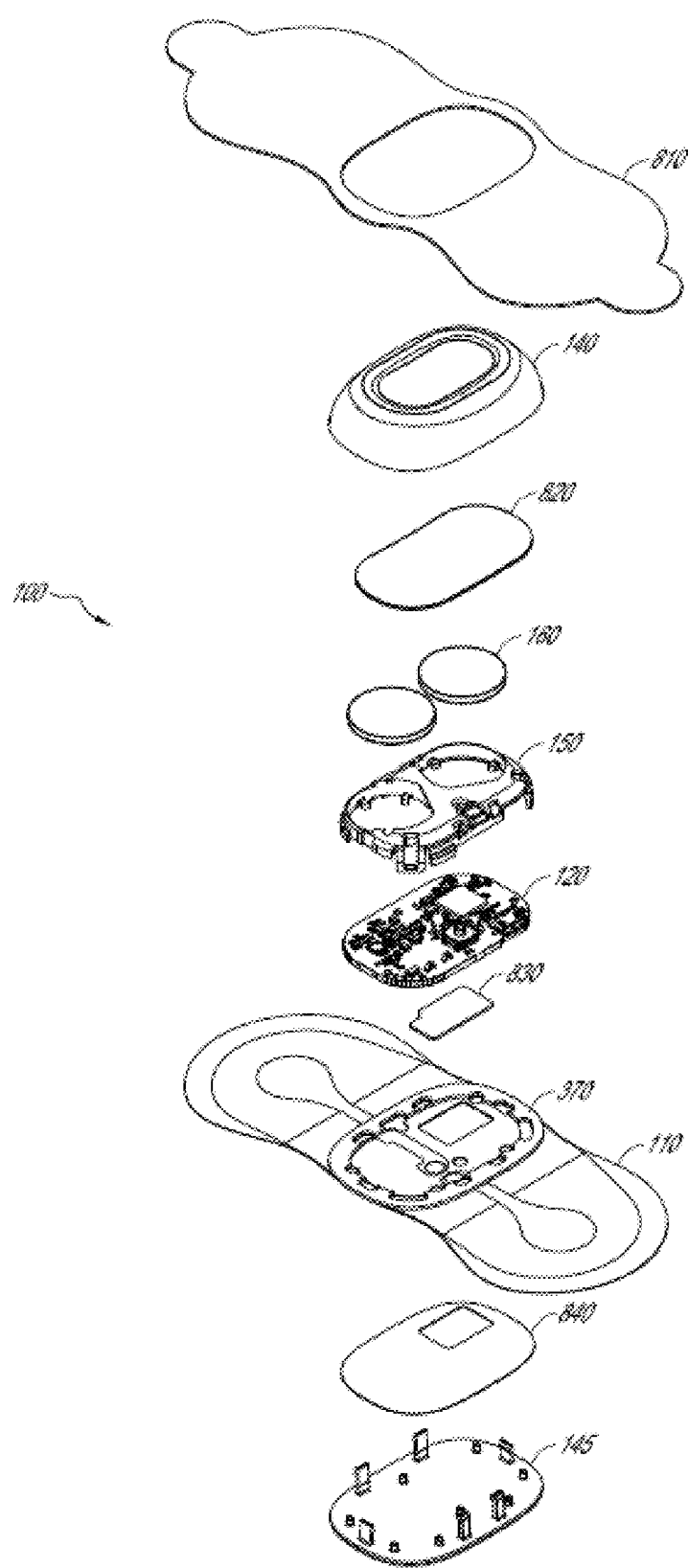
FIG. 12 is an exploded view of the physiological monitoring device including a number of optional items, according to one embodiment.

Referring to FIG. 12, in some embodiments, physiological monitoring device 100 may include one or more additional, optional features. For example, in one embodiment, monitoring device 100 may include a removable liner 810, a top label 820, a device identifier 830 and a bottom label 840. Liner 810 may be applied over a top surface of flexible body 110 to aid in the application of device 100 to the subject. As is described in further detail below, liner 810 may help support borders 133 of flexible body 110, as well as wings 130, 131, during removal of one or more adhesive covers (not shown) that cover adhesive surface 340 before use. Liner 810 may be relative rigid and/or firm, to help support flexible body 110 during removal of adhesive covers. In various embodiments, for example, liner 810 may be made of cardboard, thick paper, plastic or the like. Liner 810 typically includes an adhesive on one side for adhering to the top surface of wings 130, 131 of flexible body 110.

Labels 820, 840 may be any suitable labels and may include produce name(s), manufacturer name(s), logo(s), design(s) and/or the like. They may be removable or permanently attached upper housing member 140 and/or lower housing member 145, although typically they will be permanently attached, to avoid unregulated reuse and/or resale of the device by an unregistered user. Device identifier 830 may be a barcode sticker, computer readable chip, RFID, or the like. Device identifier 830 may be permanently or removably attached to PCBA 120, flexible body 110 or the like. In some embodiments, it may be beneficial to have device identifier 830 stay with PCBA 120.

Figure 13A:
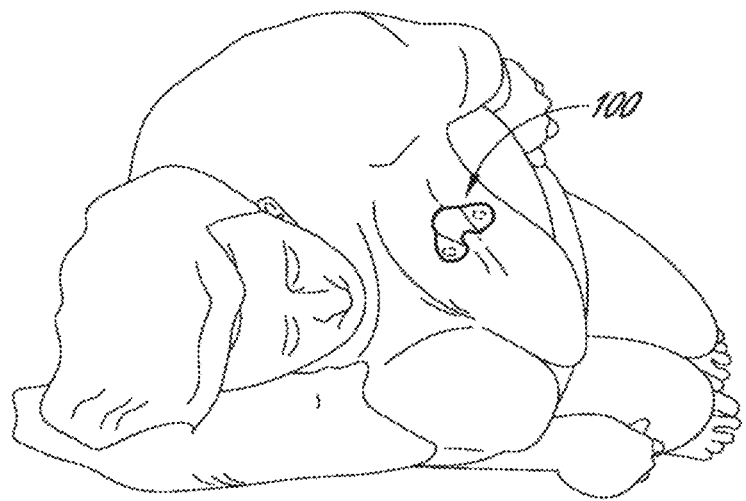
FIGS. 13A and 13B are perspective views of two people wearing the physiological monitoring device, illustrating how the device bends to conform to body movement and position, according to one embodiment.
Figure 13B:
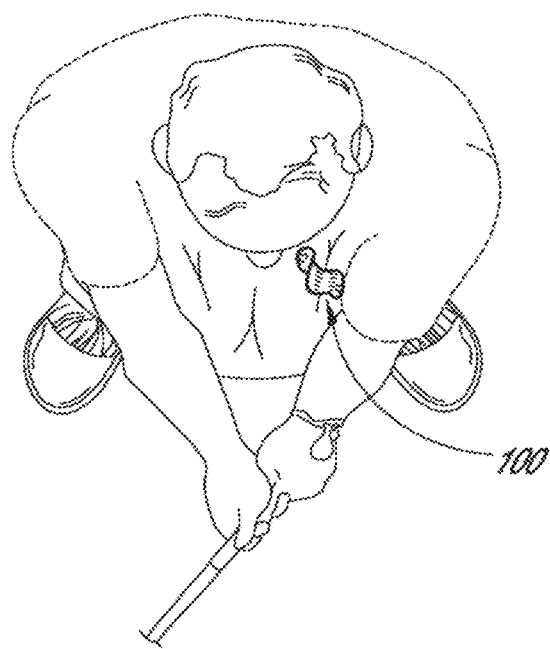

Referring now to the embodiments of FIGS. 13A and 13B, physiological monitoring device 100 may include hinge portions 132 at or near the juncture of each wing 130, 131 with housing 115. Additionally, each wing 130, 131 is typically adhered to the patient via adhesive layers 340, while rigid housing 115 is not adhered to the patient and is thus free to "float" (for example, move up and down) over the patient's skin during movement and change of patient position. In other words, when the patient's chest contracts, housing pops up or floats over the skin, thus minimizing stress on device 100, enhancing comfort, and reducing the tendency of wings 130, 131 to peel off of the skin. The advantage provided by the combination of the floating rigid housing 115 and the adhered wings 130, 131 is illustrated in FIGS. 13A and 13B. In FIG. 13A, a patient is sleeping, and in FIG. 13B, a patient is playing golf. In both examples, monitoring device 100 is squeezed together by the patient's body, causing housing 115 to float above the skin as wings 130, 131 move closer together. This advantage of a floating, non-attached portion of a physiological monitoring device is described in further detail in U.S. Pat. No. 8,560,046, which was previously incorporated by reference.

Figure 14A:
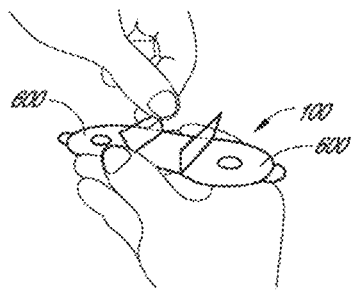
FIGS. 14A, 14B, 14C, 14D, 14E, and 14F illustrate various steps for applying the physiological monitor to a patient's body, according to one embodiment.
Figure 14B:
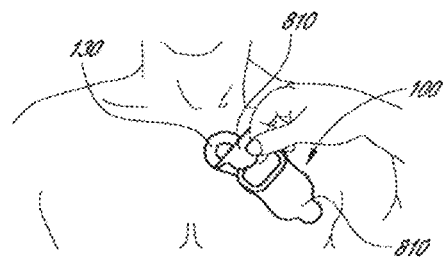
Figure 14C:
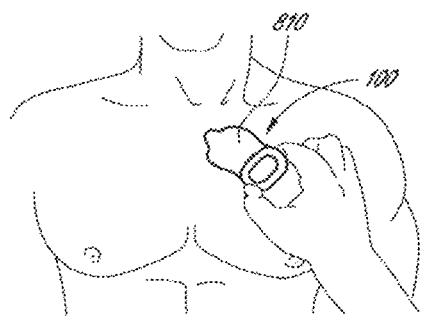

Referring now to FIGS. 14A-14F, one embodiment of a method for applying physiological monitoring device 100 to the skin of a human subject is described. In this embodiment, before the first step shown in FIG. 14A, the patient's skin may be prepared, typically by shaving a small portion of the skin on the left chest where device 100 will be placed and then abrading and/or cleaning the shaved portion. As shown in FIG. 14A, once the patient's skin is prepared, a first step of applying device 100 may include removing one or both of two adhesive covers 600 from adhesive layers 340 on the bottom surface of device 100, thus exposing adhesive layers 340. As illustrated in FIG. 14B, the next step may be to apply device 100 to the skin, such that adhesive layer 340 adheres to the skin in a desired location. In some embodiments, one adhesive cover 600 may be removed, the uncovered adhesive layer 340 may be applied to the skin, and then the second adhesive cover 600 may be removed, and the second adhesive layer 340 may be applied to the skin. Alternatively, both adhesive covers 600 may be removed before applying device 100 to the skin. While adhesive covers 600 are being removed, liner 810 acts as a support for flexible body 110, provides the physician or other user with something to hold onto, and prevents flexible body 110 and borders 133 of flexible body 110 from folding in on themselves, forming wrinkles, and so forth. As described above, liner 810 may be made of a relatively stiff, firm material to provide support for flexible body 110 during application of device 100 to the skin. Referring to FIG. 14C, after device 100 has been applied to the skin, pressure may be applied to flexible body 110 to press it down onto the chest to help ensure adherence of device 100 to the skin.

Figure 14D:
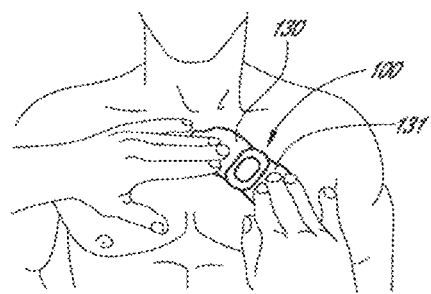
Figure 14E:
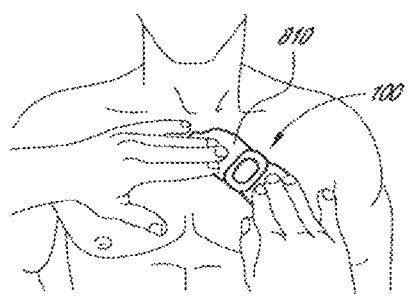
Figure 14F:
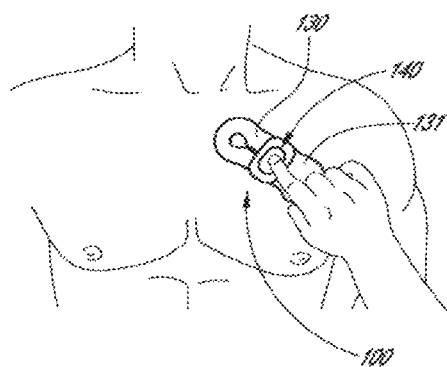

In a next step, referring to FIG. 14D, liner 810 is removed from (for example, peeled off of) the top surface of flexible body 110. As shown in FIG. 14E, once liner 810 is removed, pressure may again be applied to flexible body 110 to help ensure it is adhered to the skin. Finally, as shown in FIG. 14F, upper housing member 140 may be pressed to turn on physiological monitoring device 100. This described method is only one embodiment. In alternative embodiments, one or more steps may be skipped and/or one or more additional steps may be added.

In certain embodiments, when a desired monitoring period has ended, such as about 14 to 21 days in some cases, a patient (or physician, nurse or the like) may remove physiological monitoring device 100 from the patient's skin, place device 100 in a prepaid mailing pouch, and mail device 100 to a data processing facility. At this facility, device 100 may be partially or completely disassembled, PCBA 120 may be removed, and stored physiological data, such as continuous heart rhythm information, may be downloaded from device 100. The data may then be analyzed by any suitable method and then provided to a physician in the form of a report. The physician may then discuss the report with the patient. PCBA 120 and/or other portions of device 100, such as housing 115, may be reused in the manufacture of subsequent devices for the same or other patients. Because device 100 is built up as a combination of several removably coupled parts, various parts may be reused for the same embodiment or different embodiments of device 100. For example, PCBA 120 may be used first in an adult cardiac rhythm monitor and then may be used a second time to construct a monitor for sleep apnea. The same PCBA 120 may additionally or alternatively be used with a differently sized flexible body 110 to construct a pediatric cardiac monitor. Thus, at least some of the component parts of device 100 may be interchangeable and reusable.

In further embodiments described in greater detail below, the monitoring data may be transmitted wirelessly or through other communication mediums to be analyzed, rather than requiring physical shipment of the device for analysis and reporting.

Advantageously, physiological monitoring device 100 may provide long term adhesion to the skin. The combination of the configuration of flexible and conformal body 110, the watertight, low profile configuration of housing 115, and the interface between the two allows device 100 to compensate for stress caused as the skin of the subject stretches and bends. As a result, device 100 may be worn continuously, without removal, on a patient for as many as 14 to 21 days or more. In some cases, device 100 may be worn for greater or less time, but 14 to 21 days may often be a desirable amount of time for collecting heart rhythm data and/or other physiological signal data from a patient.

In various alternative embodiments, the shape of a particular physiological monitoring device may vary. The shape, footprint, perimeter or boundary of the device may be circular, an oval, triangular, a compound curve or the like, for example. In some embodiments, the compound curve may include one or more concave curves and one or more convex curves. The convex shapes may be separated by a concave portion. The concave portion may be between the convex portion on the housing and the convex portion on the electrodes. In some embodiments, the concave portion may correspond at least partially with a hinge, hinge region or area of reduced thickness between the body and a wing.

While described in the context of a heart monitor, the device improvements described herein are not so limited. The improvements described in this application may be applied to any of a wide variety of physiological data monitoring, recording and/or transmitting devices. The improved adhesion design features may also be applied to devices useful in the electronically controlled and/or time released delivery of pharmacological agents or blood testing, such as glucose monitors or other blood testing devices. As such, the description, characteristics and functionality of the components described herein may be modified as needed to include the specific components of a particular application such as electronics, antenna, power supplies or charging connections, data ports or connections for down loading or off-loading information from the device, adding or offloading fluids from the device, monitoring or sensing elements such as electrodes, probes or sensors or any other component or components needed in the device specific function. In addition or alternatively, devices described herein may be used to detect, record, or transmit signals or information related to signals generated by a body including but not limited to one or more of ECG, EEG and/or EMG. In certain embodiments, additional data channels can be include to collect additional data, for example, device motion, device flex or bed, heart rate and/or ambient electrical or acoustic noise.

The physiological monitors described above and elsewhere in the specification may further be combined with methods and systems of data processing and transmission that improve the collection of data from the monitor. Further, the methods and systems described below may improve the performance of the monitors by enabling timely transmission of clinical information while maintaining the high patient compliance and ease-of-use of the monitor described above. For example, the methods and systems of data processing and transmission described herein this section of elsewhere in the specification may serve to extend the battery life of the monitor, improve the accuracy of the monitor, and/or provide other improvements and advantages as described herein this section or elsewhere in the specification.

Device Monitoring and Clinical Analysis Platform

The systems and methods described in detail below, in reference to the embodiments of FIG. 15, may selectively extract, transmit, and analyze electrocardiographic signal data and other physiological data from a wearable physiological monitor, such as is described above in relation to FIGS. 1 through 14. The systems and methods described below can improve the performance of a wearable physiological monitor that simultaneously records and transmits data through multiple means. For example, selective transmission of extracted data allows for decreased power consumption because the wearable patch is not required to transmit all recorded data. By sending extracted data, much of the analysis may be performed away from the wearable device without requiring full on-board rhythm analysis, which can also be highly power consumptive, reducing battery life. Further, remote analysis without the power constraints inherent to a wearable device may allow for greater sensitivity and accuracy in analysis of the data. Decreased power consumption serves to improve patient compliance because it prolongs the time period between or even eliminates the need for device replacement, battery changes or battery recharging during the monitoring cycle. By decreasing battery consumption, longer monitoring times may be enabled without device replacement, for example, at least one week, at least two weeks, at least three weeks, or more than three weeks.

Figure 15:
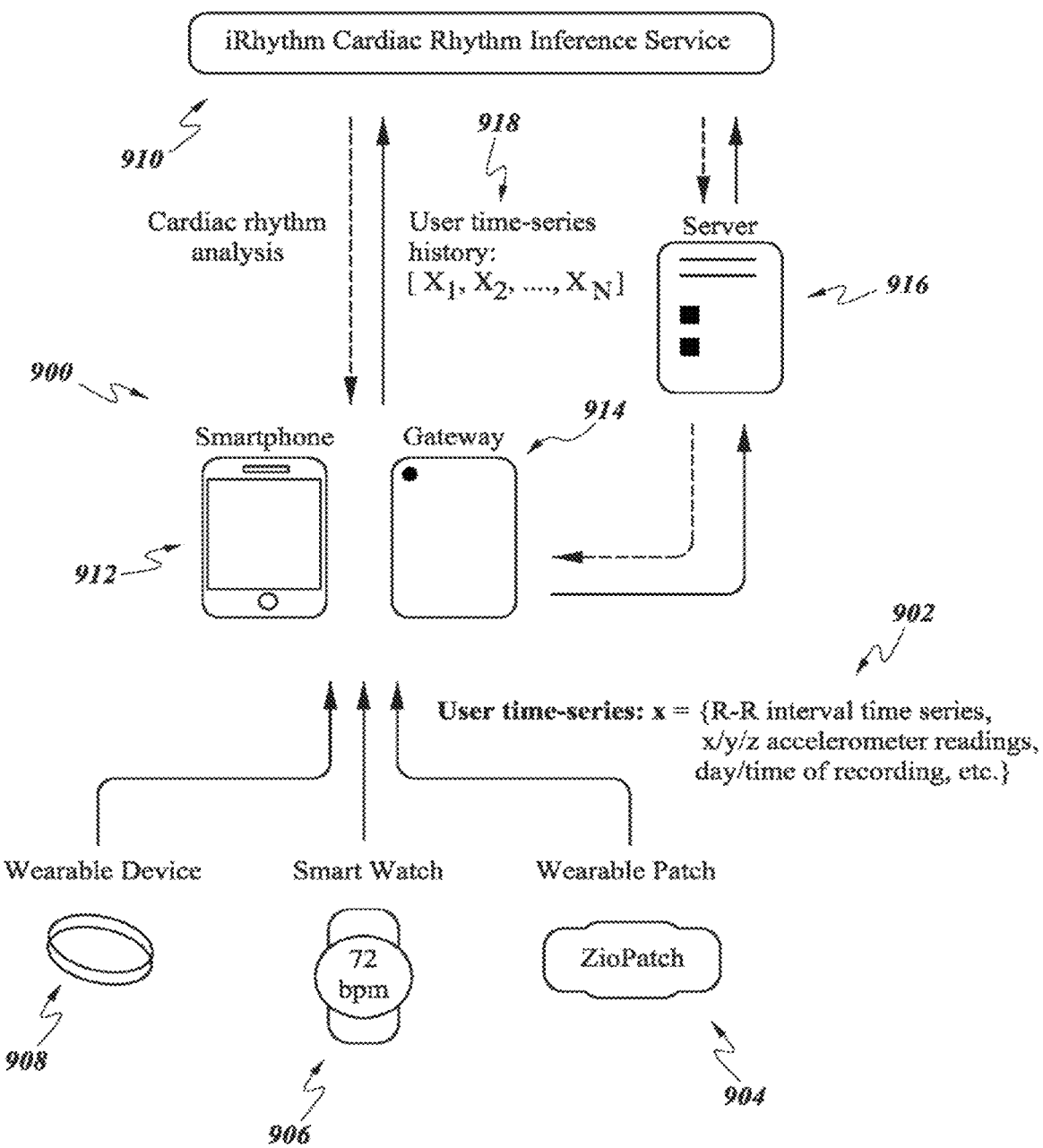
FIG. 15 illustrates a schematic diagram of an embodiment of a cardiac rhythm inference service.

FIG. 15 depicts a general overview of an embodiment of a system 900 for inferring cardiac rhythm information from an R-R interval time series 902, as may be generated by a continuous heart rate monitoring device 904. The R-R interval time series 902 inputted to the system may include a series of measurements of the timing interval between successive heartbeats. Typically each interval represents the time period between two successive R peaks as identified from an ECG signal. R peaks are part of the QRS complex, a combination of three graphical deflections typically seen on an ECG, representing the depolarization of the left and right ventricles of a mammal's heart. The R peak is generally the tallest and most visible upward deflection on an ECG, and thus makes for an appropriate reference point. However, in further embodiments, any characteristic ECG fiducial point (such as the QRS complex onset or offset) may be used in place of the R peak to provide an estimate of the R-R interval time series. The physical characteristics of the monitoring device are constructed in such a way as to improve signal fidelity, therefore the high signal fidelity allows for a high level of confidence in accurately extracting R-R peak data.

The R-R interval time series 902 data may be extracted from or received from a dedicated heart rate monitor such as a heart rate chest strap or heart rate watch, or a wearable health or fitness device 906, 908 that incorporates heart rate sensing functionality. Alternatively, the R-R interval time series 902 may be derived from a wearable patch designed to measure an ECG signal 904 (for instance, by locating the R peaks in the ECG using a QRS detection algorithm). Furthermore, the R-R interval time series 902 may be estimated from an alternative physiological signal such as that obtained from photoplethysmography (PPG). In this scenario, the peak-to-peak interval time series determined from the PPG signal may be used as an accurate estimate of the R-R interval time series.

In one aspect, a cardiac rhythm inference system 910 is implemented as a cloud service or server-based system that exposes an application programming interface (API) enabling R-R interval time series data or other signal data to be transmitted to the system (for instance, via HTTP) and the resulting cardiac rhythm information to be returned to the calling software. The R-R interval time series data 902 or other signal data may be transmitted to the cloud service directly from the heart-rate monitoring device itself, or indirectly via a smartphone 912, tablet or other internet-enabled communication device 914 that can receive data from the heart rate monitoring device in either a wireless or wired manner. In addition, the R-R interval time series data 902 or other signals may be transmitted from a server 916 that stores the data for a number of users.

In some embodiments, a cardiac rhythm inference system 910 is provided through a software library that can be incorporated into a standalone application for installation and use on a smartphone, tablet or personal computer. The library may provide identical functionality to that of the inference service, but with R-R interval time series data 902 or other signal data transmitted directly through a functional call, as opposed to through a web service API.

In certain embodiments, a cardiac rhythm inference system may accept a plurality of R-R interval time series measured from devices of a given user 918, in addition to an individual R-R interval time series 902. In this scenario, the system computes the frequency and duration of each of the cardiac rhythm types inferred from the collection of time series data. These results may then be used to estimate confidence statistics for each type of cardiac rhythm based on the frequency and duration of occurrence of that rhythm across the various time series. In addition, the rhythm confidence statistics may be updated in a sequential manner for each separate call of the inference service. Furthermore, in some embodiments, the cardiac rhythm information inferred by the system may be provided back to the calling software only in the event that the confidence score for a given rhythm type exceeds a pre-determined threshold value.

In particular embodiments, a cardiac rhythm inference system 910 may accept additional sources of data, generally described as alternate sensor channels, in addition to R-R interval time series data, to enhance the accuracy and/or value of the inferred results. One additional source of data includes user activity time series data, such as that measured by a 3-axis accelerometer concurrently with the R-R interval time series measurements. In addition, the system may accept other relevant metadata that may help to improve the accuracy of the rhythm analysis, such as user age, gender, indication for monitoring, pre-existing medical conditions, medication information, medical history and the like, and also information on the specific day and time range for each time series submitted to the system. Furthermore, the measurement device might also provide some measure of beat detection confidence, for example, for each R-Peak or for sequential time periods. This confidence measure would be based on analysis the recorded signal that, in typical embodiments, would not be recorded due to storage space and battery energy requirements. Finally, in the particular case that the R-R interval time series data are derived from an ECG signal, the system may accept additional signal features computed from the ECG. These features may include a time series of intra-beat interval measurements (such as the QT or PR interval, or QRS duration), or a time series of signal statistics such as the mean, median, standard deviation or sum of the ECG signal sample values within a given time period.

The various aspects described above could be used either individually or in combination to provide an application providing insights into an individual's health, stress, sleep, fitness and/or other qualities.

Some embodiments concern a system for selective transmission of electrocardiographic signal data from a wearable medical sensor. Current wearable sensors, such as the iRhythm ZioPatch™ 904, and further described above are capable of recording a single-lead electrocardiogram (ECG) signal for up to two weeks on a single battery charge. In many situations however, it is desirable for the sensor to be able to transmit, in real-time or near real-time, specific sections of the recorded ECG signal with clinical relevance to a computer device, such as either a smartphone 912 or an internet-connected gateway device 914 for subsequent processing and analysis. In this way, the patient or their physician can be provided with potentially valuable diagnostic ECG information during the period that the patient wears the sensor.

As described above, a significant challenge with this approach is to manage the battery life of the wearable sensor without requiring replacement or recharging, both of which reduce user compliance. Each transmission of an ECG from the sensor to a smartphone or local gateway device (using, for example, Bluetooth Low Energy) results in a subsequent reduction in the total charge stored in the sensor battery. Some embodiments of the present disclosure address this issue through the use of a novel hardware and software combination to enable the selective transmission of clinically relevant sections of ECG from a wearable sensor.

In certain embodiments, the wearable sensor incorporates either a software, hardware or hybrid QRS detector that produces a real-time estimate of each R-peak location in the ECG. The R-peak location data is then used to compute an R-R interval time series that is subsequently transmitted to a smartphone or gateway device according to a predefined schedule (for example, once per hour). In addition, a time stamp is also transmitted which stores the onset time for the R-R interval time series relative to the start of the ECG recording. Since the R-R interval time series for a given section of ECG is significantly smaller (in terms of bytes occupied) than the ECG signal itself, it can be transmitted with considerably less impact on battery life.

In some embodiments of a second stage of the system, the R-R interval time series together with the onset time stamp is subsequently transmitted by the smartphone or gateway device to a server. On the server, the R-R interval time series is used to infer a list of the most probable heart rhythms, together with their onset and offset times, during the period represented by the time series data. The list of inferred heart rhythms is then filtered according to specific criteria, such that only rhythms matching the given criteria are retained after filtering. A measure of confidence may also be used to assist in filtering the events in a manner that might improve the Positive Predictivity of detection.

In certain embodiments of a third stage of the system, for each rhythm in the filtered rhythm set, the server transmits to the smartphone or gateway device the onset and offset time for that specific rhythm. In the event that the inferred rhythm duration exceeds a pre-defined maximum duration, the onset and offset times may be adjusted such that the resulting duration is less than the maximum permissible duration. The onset and offset times received by the gateway are then subsequently transmitted to the wearable sensor, which in turn transmits the section of the recorded ECG signal between the onset and offset times back to the gateway. This section of ECG is then transmitted to the server where it can be analyzed and used to provide diagnostic information to the patient or their physician.

In some embodiments, the system fundamentally allows a device worn for up to about: 14, 21, or 30 days or beyond without battery recharging or replacement (both activities that reduce patient compliance and, therefore, diagnostic value) to provide timely communication of asymptomatic arrhythmia events. This development is motivated by technology constraints: in order to enable a small, wearable device that does not require battery change or recharging while providing continuous arrhythmia analysis with high accuracy, it is desirable to limit the complexity of analysis performed on-board. Similarly, streaming of all of the recorded ECG data to an off-board analysis algorithm may not be practical without imposing greater power requirements. This motivates a more creative "triage" approach where selected features of the recorded ECG signal, including but not limited to R-R intervals, are sent for every beat, allowing a customized algorithm to locate a number (for example, 10) of 90-second events to request from the device in full resolution to support comprehensive analysis, for example, a resolution capable of supporting clinical diagnosis.

In other embodiments, the system would provide the ability to detect asymptomatic arrhythmias in a timely manner on a wearable, adhesively affixed device that does not require frequent recharging or replacement. This would be used to enhance the value of some current clinical offerings, which only provide clinical insight after the recording is completed and returned for analysis.

In certain embodiments, the system would allow actionable clinical insight to be derived from data collected on low-cost, easy-to-use consumer wearable devices that are otherwise only focused on fitness and wellness. For example, the technology could be used to create a very effective, low-cost screening tool capable of detecting the presence of Atrial Fibrillation in the at-large population. By using such a tool, not only would patients in need of care be found more easily, but it may be done earlier and more cost effectively, which lead to better outcomes—namely, through reducing stroke risk by identifying AF more quickly.

In particular embodiments, the system may provide the service through a downloadable application that, after receiving customer consent for data access and payment approval, would initiate access and analysis of heart beat data stored from wearable devices, either stored locally in a mobile device or in an online repository. This data pull and analysis would happen through an Algorithm API, and would result in a clinical finding being sent back to the application to be provided to the user. If the data was sufficient to support a "screening oriented" finding, for example, "Likely presence of an irregular rhythm was detected", the application would direct them to a cardiologist where a more diagnostically focused offering, for example, the ZIO® Service, could be provided to support clinical diagnosis and treatment. In further embodiments, as also described elsewhere in the specification, the system may trigger an alarm if a particular measurement and/or analysis indicates that an alarm is needed.

Further examples of additional scenarios of clinical value may include coupling ambulatory arrhythmia monitoring with a blood-alcohol monitor to study the interaction of AF and lifestyle factors. For example, ambulatory arrhythmia monitoring could be coupled with a blood-glucose monitor to study the impact of Hypoglycemia on arrhythmias. Alternatively, ambulatory arrhythmia monitoring could be coupled with a respiratory rate and/or volume monitor to study the interaction of sleep apnea and breathing disorders. Further, there could be evaluation of the high rates of supraventricular ectopic beats as a potential precursor for AF (for example, 720 SVEs in 24-hour period).

Each of the processes, methods, and algorithms described in the preceding sections may be embodied in, and fully or partially automated by, code modules executed by one or more computer systems or computer processors comprising computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The term "including" means "included but not limited to." The term "or" means "and/or."

Any process descriptions, elements, or blocks in the flow or block diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be at least partially embodied in, and partially or fully automated via, software code modules executed by one or more computers. For example, the methods described herein may be performed by the computing system and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. For example, a feature of one embodiment may be used with a feature in a different embodiment. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Various embodiments of a physiological monitoring device, methods, and systems are disclosed herein. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

Various modifications to the implementations described in this disclosure may be made, and the generic principles defined herein may be applied to other implementations without departing from the spirit or scope of this disclosure. Thus, the scope of the disclosure is not intended to be limited to the implementations shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, such operations need not be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, the separation of various system components in the embodiments described above should not be interpreted as requiring such separation in all embodiments. Additionally, other embodiments are within the scope of the following claims. In some cases, the actions recited in the claims can be performed in a different order and still achieve desirable results.

What is claimed is:

1. A monitoring device configured to attach to a user, the device comprising
    a housing comprising a hardware processor;
    a wing extending from the housing and configured to conform to a surface of a user, the wing comprising an electrode configured to detect a physiological signal of the user, the electrode in electrical communication with the hardware processor;
    an adhesive layer coupled to the bottom surface of the wing, the adhesive layer configured to adhere the wearable device to the user;
    a substrate layer positioned over the adhesive layer, the substrate layer comprising a plurality of apertures extending from a bottom surface of the substrate layer to a top surface of the substrate layer, the apertures configured to transport moisture from the surface of the user; and
    wherein individual apertures overlie individual continuous portions of the adhesive layer.

2. The monitoring device of claim 1, wherein individual apertures extend in a direction substantially normal to the bottom surface and the top surface.

3. The monitoring device of claim 1, wherein individual apertures are substantially arranged in an array.

4. The monitoring device of claim 1, wherein the adhesive layer comprises channels.

5. The monitoring device of claim 4, wherein the channels are arranged in a radial pattern.

6. The monitoring device of claim 4, wherein the channels comprise a shape selected from the group consisting of diamond, oval, rectangle, circle, or trapezoid.

7. The monitoring device of claim 6, wherein the channels are diamond shaped.

8. The monitoring device of claim 4, wherein the channels are partially aligned with the height of the user such that moisture drainage increases when the user is in an upright position.

9. The monitoring device of claim 4, wherein the channels are aligned transverse to a direction of extension and contraction of an underlying muscle of the user.

10. The monitoring device of claim 1, further comprising a void positioned in a central portion of the substrate layer.

11. The monitoring device of claim 1, wherein the adhesive layer comprises a plurality of adhesive islands, individual adhesive islands connected by a web.

12. The monitoring device of claim 1, wherein the adhesive layer further comprises a wicking material.

13. A method of monitoring physiological signals, comprising:
attaching a monitoring device to a user, the monitoring device comprising:
a housing comprising a hardware processor,
a wing extending from the housing, the wing comprising an adhesive layer coupled to a bottom surface of the wing,
a substrate layer overlying the adhesive layer, the substrate layer comprising a plurality of apertures extending from a bottom surface of the substrate layer to a top surface of the substrate layer, the apertures configured to transport moisture from the surface of the user, and
wherein individual apertures overlie individual continuous portions of the adhesive layer; and
collecting physiological data from the user.

14. The method of claim 13, wherein individual apertures extend in a direction substantially normal to the bottom surface and the top surface.

15. The method of claim 13, wherein the adhesive layer comprises channels.

16. The method of claim 15, wherein the channels are arranged in a radial pattern.

17. The method of claim 13, further comprising a void positioned in a central portion of the substrate layer.

18. The method of claim 13, wherein the adhesive layer comprises adhesive islands connected by a web.

19. The method of claim 13, wherein the adhesive layer further comprises a wicking material.

20. The method of claim 13, further comprising transmitting the physiological data to a computing system.

* * * * *